(12) United States Patent
Bouille et al.

(10) Patent No.: US 11,371,059 B2
(45) Date of Patent: Jun. 28, 2022

(54) VIRAL PARTICLE FOR THE TRANSFER OF RNAS, ESPECIALLY INTO CELLS INVOLVED IN IMMUNE RESPONSE

(71) Applicant: FLASH THERAPEUTICS, Toulouse (FR)

(72) Inventors: Pascale Bouille, Vincennes (FR); Christine Duthoit, Portet-sur-Garonne (FR); Lucille Lamouroux, Pinsaguel (FR)

(73) Assignee: FLASH THERAPEUTICS, Toulouse (FR)

( * ) Notice: Subject to any disclaimer, the term of this patent is extended or adjusted under 35 U.S.C. 154(b) by 300 days.

(21) Appl. No.: 16/301,354

(22) PCT Filed: May 12, 2017

(86) PCT No.: PCT/FR2017/051165
§ 371 (c)(1),
(2) Date: Nov. 13, 2018

(87) PCT Pub. No.: WO2017/194903
PCT Pub. Date: Nov. 16, 2017

(65) Prior Publication Data
US 2019/0203228 A1    Jul. 4, 2019

(30) Foreign Application Priority Data

May 13, 2016   (FR) ..................................... 1654333
Mar. 31, 2017  (FR) ..................................... 1752819

(51) Int. Cl.
| | | |
|---|---|---|
| *A61K 39/00* | (2006.01) | |
| *A61K 39/21* | (2006.01) | |
| *C07K 14/005* | (2006.01) | |
| *C12N 15/86* | (2006.01) | |
| *A61K 39/12* | (2006.01) | |
| *C12N 7/00* | (2006.01) | |
| *C07K 14/16* | (2006.01) | |

(52) U.S. Cl.
CPC .............. *C12N 15/86* (2013.01); *A61K 39/00* (2013.01); *C07K 14/005* (2013.01); *C07K 14/161* (2013.01); *C12N 7/00* (2013.01); *A61K 2039/53* (2013.01); *C07K 2319/735* (2013.01); *C07K 2319/85* (2013.01); *C12N 2740/16023* (2013.01); *C12N 2740/16043* (2013.01); *C12N 2740/16052* (2013.01); *C12N 2795/18122* (2013.01); *C12N 2800/24* (2013.01); *C12N 2800/50* (2013.01); *C12Y 207/00* (2013.01)

(58) Field of Classification Search
CPC .......... C12N 15/86; C12N 2740/16222; C07K 14/005; A61P 31/18; A61K 39/12
See application file for complete search history.

(56) References Cited

FOREIGN PATENT DOCUMENTS

| JP | 2015-504897 A | 2/2015 |
| WO | 2007/072056 A2 | 6/2007 |
| WO | 2016049258 A2 | 3/2016 |

OTHER PUBLICATIONS

Prel et al., "Highly efficient in vitro and in vivo delivery of functional RNAs using new versatile MS2-chimeric retrovirus-like particles", Molecular therapy—Methods & clinical development, 2015, 2:1-15.*
Carruthers et al., "Fat Grafting as a vehicl for the delivery of recombinant adenoassociated viral vectors to achieve gene modification of muscle flasps" (Annals of Plastic surgery, 2013, 70(6):726-731).*
Anne Prel et al: "Highly efficient in vitro and in vivo delivery of functional RNAs using new versatile M52-chimeric retrovirus-like particles", Molecular Therapy—Methods & Clinical Development, pp. 1-16, (Oct. 2015).
Michael R. Williams et al: A Retroviral CRISPR-Cas9 System for Cellular Autism-Associated Phenotype Discovery in Developing Neurons, Scientific Reports, pp. 1-12 (May 2016).
Katherine H. Carruthers et al, "Fat Grafting as a Vehicle for the Delivery of Recombinant Adenoassociated Viral Vectors to Achieve Gene Modification of Muscles Flaps", Annals of Plastic Surgery, pp. 726-731, vol. 70, No. 6 (Jun. 2013).
Pascale Bouille et al: "Transient Non-Viral RNA Delivery Mediated by a Lentiviral Particle", Molecular Therapy, p. 1, vol. 24, No. S1 (May 2016).

* cited by examiner

*Primary Examiner* — Barry A Chestnut
(74) *Attorney, Agent, or Firm* — Browdy and Neimark, PLLC

(57) ABSTRACT

The present invention relates to retroviral particle comprising a protein derived from the Gag polyprotein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the protein derived from the Gag polyprotein and/or into the integrase, and at least one of said sequences of interest of the encapsidated non-viral RNAs comprises a part coding at least one epitope and/or at least one molecular structure specifically recognizing an epitope.

21 Claims, 36 Drawing Sheets linear pcDNA.EF1.Fluorescent Gene. MS2 12X linear p8.74-ΔZF-MS2 Coat linear pENV linear pILV-EF1.Luciferase.WPRE linear pILV-EF1.Fluorescent Gene.WPRE linear pILV-EF1.Cre.WPRE linear pcDNA.EF1.PPRV.MAGEA3.IRES.GFP.WPRE.MS2 12X

FIG. 11A linear pcDNA.EF1long.PPRV.PS-AgMageA3.WPRE.MS2 12X

FIG. 11B linear pcDNA.EF1long.PPRV.PS-Aggp100.WPRE.MS2 12X

FIG. 11C linear pcDNA.EF1long.PPRV.PS-AgTyrosinase.WPRE.MS2 12X

FIG. 11D linear pILV.EF1.MAGEA3.IRES.GFP.WPRE linear pILV.EF1.PS-AgMAGE A3.WPRE linear pILV.EF1.PS-Aggp100.WPRE linear pILV.EF1.PS-AgTyrosinase linear pcDNA.EF1.PP7 2X Linear p8.74- Pol-PP7 Coat Linear p8.74- Pol-PP7 Coat CD8+ cells
from wild-type
BALB/c mice CD8+ cells from
BALB/c mice with a
Renca tumour Positive sorting of the CD8+ T lymphocytes derived from the splenocytes and CFSE labelling at D0

Results of the co-cultures of the CFSE-labelled CD8+ cells with the BMDCs at D5 (1DC:2T)

pcDNA.EF1.FluorescentReporter.PP7 2X

VIRAL PARTICLE FOR THE TRANSFER OF RNAS, ESPECIALLY INTO CELLS INVOLVED IN IMMUNE RESPONSE

The present invention relates to a retroviral system for the transfer of non-viral RNAs Into target cells and more particularly a retroviral particle capable of delivering multiple RNAs. The invention also relates to compositions comprising these retroviral particles, kits for producing the latter, the associated manufacturing methods as well as the uses of the particles and compositions.

Introduction of multiple RNAs into a target cell is a major challenge in research and development and in gene therapy.

The use of vectors derived from viruses has become a crucial method for the transfer of genes. Nowadays, viral vectors are classified into two main categories:
 integrative vectors, which integrate into the recipient genome, and
 non-integrative vectors, which usually form an extra-chromosomal genetic element.

The integrative vectors such as the gamma-retroviral vectors (RV) and lentiviral vectors (LV) are integrated stably. The non-integrative vectors, such as the adenoviral vectors (ADV) and adeno-associated vectors (AAV) are quickly eliminated from rapidly dividing cells. Certain factors influencing the choice of a particular vector comprise its encapsidation capacity, its range of target or host cells, its gene expression profile, its transduction effectiveness and its capacity to induce an immune response, which is particularly problematic if repeated transductions are required.

Certain applications require the use of non-integrative vectors such as in gene therapy or in many applications in vitro, ex vivo and in vivo. As examples, there may be mentioned:
 induction of the reprogramming of specialized cells into pluripotent cells, as well as induction of the differentiation of stem cells or pluripotent cells into specialized cells,
 expression of antigens or of proteins (toxic or non-toxic) simultaneously in a target cell,
 expression of genome engineering systems for example such as the CRE or TALEN protein or the CRISPR system, or of any other system requiring protein or RNA expression.

One way of introducing RNAs into a target cell employs viral vectors based on viruses belonging to the family Retroviridae (also denoted the family of Retroviruses or RNA viruses). In fact, during its replication cycle, a virus of the family Retroviridae has the capacity to convert its genome, constituted by RNA, into double-stranded DNA, which will be integrated into the genome of the target cell. Particular examples of this family of Retroviruses are the gamma-retroviruses and the lentiviruses.

The replication cycle of a retrovirus comprises a first recognition phase of the target (or host) cell via binding to a membrane receptor. This recognition phase leads, after membrane fusion, to entry of the retrovirus into the host cell. The retroviral RNA is then copied into double-stranded DNA by reverse transcriptase, encoded by the retrovirus, and then integrated into the genome of the host cell. This viral genome is then transcribed by the host cell like all the other genes of the cell. This genome codes all of the proteins and sequences allowing the manufacture of other viruses.

More particularly, three genes are common to all retroviruses: gag, pol and env.

Gag is a gene coding a polyprotein, the proteins derived from this polyprotein by cleavage being structural proteins involved in assembly of the viruses during replication. These structural proteins are more specifically the matrix protein (MA), the capsid protein (CA) and the nucleocapsid protein (NC).

Pol is a gene coding the enzymes integrase, reverse transcriptase and protease.

Env is a gene coding envelope glycoproteins.

These three genes therefore make it possible to copy retroviral RNA into double-stranded DNA, integrate this DNA into the genome of the host cell and then generate the structure of the neo-synthesized retroviruses: envelope, capsid and nucleocapsid proteins. However, for the neo-synthesized retroviruses to be complete, it is necessary to encapsidate two copies of the retroviral RNA in each of these structures. This encapsidation of two copies of the retroviral RNA in the structure is carried out by recognition, by the nucleocapsid protein, of an encapsidation sequence called Psi (for "Packaging Signal") carried by the copy of the retroviral RNA.

When a viral vector derived from a retrovirus is used for purposes of gene therapy, at least one part of the coding regions of gag, pol and/or env is dissociated between the encapsidation system and the expression system of the sequence of interest. The coding sequences gag and pol, for example, are carried by the encapsidation plasmid providing in trans the proteins that are necessary for producing viral vectors. The encapsidation sequence and the sequence of interest are carried by independent systems, in order to make the retrovirus non-replicative.

However, in certain cases, integration of the RNA sequence of interest into the genome of the host cell randomly may interrupt an open reading frame and block the expression of important genes. Moreover, for certain applications, such as cell reprogramming, genome editing or stem cell differentiation, it is recommended for the expression of a sequence of interest to be carried out transiently.

Application WO2007/072056 describes a viral vectorization system comprising env, gag, optionally gag/pol as well as an RNA sequence containing a heterologous encapsidation signal that is recognized by a corresponding RNA binding domain associated with gag or with gag/pol. This system is described in the application as being non-integrative and allowing a transient expression.

However, the effectiveness of such systems remains limited. In particular, for a target cell to express an RNA of interest carried by these systems, it is generally necessary to introduce several copies of this RNA of interest into the cell and consequently use high multiplicities of infection (MOIs). The MOI corresponds to the ratio of the number of vectorization systems introduced to the number of cells to be infected. A high MOI in fact makes it possible to introduce several copies of the RNA of interest into the cells, allowing one and the same cell to undergo several infections. Now, although it makes it possible to improve the expression level of the RNA of interest that is carried, the use of high MOIs also generates some degree of toxicity, because of the multiple infections that the cell undergoes.

This type of system for RNA transfer is also of interest for immunotherapy, and in particular anti-tumour immunotherapy.

Anti-tumour immunotherapy is a therapeutic strategy that is based on the immune system in order to eradicate the tumour cells. New approaches consist of genetically modifying the patient's cells in order to induce an immune response and improve targeting. For these new gene therapies to be usable in clinical practice, a method of gene transfer that is safe and effective is required. RNA transfection and the use of lentiviral vectors, respectively, have emerged as suitable technologies for transferring either a specific receptor of the T lymphocytes into lymphocytes or an antigen into dendritic cells.

The molecular identification of specific antigens of human tumour cells is a key element in the development of immunotherapy specific to targeted antigens:

One approach, described as passive immunotherapy, consists of amplifying specific T cells of antigens ex vivo and reimplanting them in the patients (TCR & CAR T cells). Gene transfer is used here for introducing chimeric receptors of synthetic antigens (CARs) or new T cell receptors (TCRs) into these T cells before reimplanting them by adoptive transfer for the treatment of cancers. Here, lentiviral vectors are widely used, and very encouraging results have been obtained at the clinical stage.

The other approach, described as active immunotherapy, is vaccination. The dendritic cells (DCs) are natural antigen-presenting agents. The dendritic cells are at the centre of many anti-tumour therapeutic strategies owing to their capacity for stimulating naive T cells. In fact, the dendritic cells are the "detectors" of the environment and transmit the information gathered to the T and B cells of the immune system. These cells are therefore essential targets for generating anti-tumour therapeutic immunity and accordingly are described as professional antigen-presenting cells (APCs). The purpose of vaccination based on dendritic cells is both to induce an in vivo response of the effector T cells in order to reduce the tumoral mass specifically as well as to install a memory response.

These two therapeutic approaches involve two distinctive features for obtaining an anti-tumour immune response that is effective and reproducible. Firstly, expression of exogenous sequences such as the antigens in the target cells must be controlled in order to obtain an immune response without inducing toxicity. The co-expression of several antigens at the same moment in time is a good opportunity to increase the anti-tumour response and avoid the escape of tumour cells.

The APCs have an essential role in the immune system and constitute a determining element in an immunotherapy strategy. The APCs have the task of presenting the antigenic peptides to the cells of the immune system. If the antigen or antigens are immunogenic, the immune system will be specifically activated in order to eliminate the cells expressing it or them. This response will therefore be directed against the APCs but also against any cell that will express the antigen, which is the case for the tumour cells. Any antigen-presenting cell (APC) brought into contact with a foreign antigen will process it in order to combine it with the molecules of the MHC (Major Histocompatibility Complex) that will allow presentation of antigenic peptides at its surface. This ensemble will be able to generate an activation of the lymphocytes with which the APCs will come into contact in the secondary lymphoid organs. A given tumour generally expresses several different antigens, against which it is crucial to educate the cells of the immune system in order to make them effective against the tumour. These tumoral antigens may also be expressed at different levels depending on the stages of development of a tumour. Manipulation of the response to several antigens may therefore prove crucial for the efficacy of the treatment with the modified immune cells.

The second point is the expression, in the target cells, of immuno-modulating agents that trigger maturation or activation of the immune cells thus modified. These multiple co-expressions within the immune cells will make it possible to mimic the innate and adaptive immune responses. Thus, these methods will on the one hand supply cells specifically expressing antigens and on the other hand induce their maturation or differentiation, which is essential for a complete and effective immune response. This means that the most effective therapy will result from the administration of multiple genes in order to improve the therapeutic results, by combining the specificity of the immune response against several tumor antigens with stimulating responses, in a controlled, time-dependent manner. Delivering both antigens and immunomodulators in the target cells or in the body at one time should provide a clinical advantage.

These two approaches, based on T cells and on dendritic cells (APCs) respectively, are more particularly targeted by the invention.

There is therefore still a need for viral vector systems that are more efficient less toxic and more specifically adapted to immunotherapy.

The work of the inventors has made it possible to produce a vector system capable of delivering several RNAs of interest into one and the same cell in a single infection.

The present invention therefore relates to a retroviral particle comprising a protein derived from the Gag polyprotein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the protein derived from the Gag polyprotein and/or into the integrase, and at least one of said sequences of interest of the encapsidated non-viral RNAs comprises a part coding at least one epitope and/or at least one molecular structure specifically recognizing an epitope.

The retroviral particle according to the invention makes it possible to introduce at least two non-viral RNAs, preferably 3, into a cell by a single infection. The introduction of said particles into the cells may be carried out by an in vivo, in vitro or ex vivo method.

By "protein derived from the Gag polyprotein" is meant any protein resulting from cleavage of the Gag polyprotein. More particularly, it is a nucleocapsid protein, a matrix protein (for example, in retroviral particles derived from murine viruses of the MoMuLV type) or from the p12 protein, specific to the gammaretroviruses.

By "envelope protein" is meant any envelope protein, including a pseudotyping envelope protein. By way of example, there may be mentioned the Ampho envelope protein, the ecotropic envelope protein, the envelope protein of the Moloney murine leukaemia virus (MoMuLV), the envelope protein of the feline immunodeficiency virus (FIV), the envelope protein of the Harvey murine sarcoma virus (HaMuSV), the envelope protein of the murine mammary tumour virus (MuMTV), the envelope protein of the Rous sarcoma virus (RSV), the envelope protein of the measles virus (MV), the envelope protein of the Gibbon ape leukaemia virus (GALV), the protein of the feline endogenous virus (RD114) or the envelope protein of the vesicular stomatitis virus (VSV-G). More particularly, the envelope protein is the Ampho envelope protein, the ecotropic envelope protein, the envelope protein of the Moloney murine leukaemia virus (MoMuLV), the envelope protein of the feline immunodeficiency virus (FIV), the envelope protein of the Harvey murine sarcoma virus (HaMuSV), the envelope protein of the murine mammary tumour virus (MuMTV), the envelope protein of the Rous sarcoma virus (RSV), the envelope protein of the measles virus (MV), the envelope protein of the Gibbon ape leukaemia virus (GALV) or the envelope protein of the vesicular stomatitis virus (VSV-G). The envelope protein may thus be modified to target certain cellular types or certain applications (use of surface receptors as envelope protein).

It is also possible to modify the envelope protein with an antibody, a glycolipid and/or a particular ligand in order to target a receptor and/or a particular cellular type.

Preferably, the envelope protein is the VSV-G protein.

By "integrase" is meant the enzymatic protein encoded by the pol gene, which allows integration of the retroviral DNA into the DNA of the cell infected by the retrovirus during replication of said retrovirus.

By "encapsidation sequence" is meant an RNA motif (sequence and three-dimensional structure) recognized specifically by a binding domain. Preferably, the encapsidation sequence is a stem-loop motif. Even more preferably, the encapsidation sequence of the retroviral particle is the stem-loop motif of the RNA of the MS2 bacteriophage or PP7 phage for example such as that resulting from the sequence ctagaaaacatgaggatcacccatgtctgcag (SEQ ID No.1) or ctagaaaggagcagacgatatggcgtcgctccctgcag (SEQ ID No.2) respectively. The stem-loop motif and more particularly the stem-loop motif of the RNA of the MS2 bacteriophage or that of the RNA of the PP7 phage may be used alone or repeated several times, preferably from 2 to 25 times, more preferably from 2 to 18 times, for example from 6 to 18 times.

By "binding domain" is meant all or part of a protein binding specifically to the encapsidation sequence bound to the RNA sequence of interest. More particularly, it is a mutant or non-mutant protein defined by a three-dimensional structure, binding specifically to the encapsidation sequence. Preferably, the binding domain is a heterologous domain. More preferably, the binding domain is the Coat protein of the MS2 bacteriophage, of the PP7 phage or of the Qβ phage, the prophage HK022 Nun protein, the U1A protein or the hPum protein.

More preferably, the binding domain is the Coat protein of the MS2 bacteriophage or of the PP7 phage.

Even more preferably, when the binding domain is the Coat protein of the PP7 phage, the sequence of which is deficient for self-assembly, owing to a deletion of amino acids 67 to 75 (PCPΔFG) (Chao et al. 2008). Preferably, the sequence of the Coat protein of the PP7 phage is codon-optimized for human cells, i.e. the DNA bases are selected to code amino acids preferably present in the human species.

By "each sequence" is meant that the encapsidation sequences may be identical or different, depending on whether these encapsidation sequences are recognized by an identical or different binding domain. In fact, the retroviral particle according to the invention may comprise one or more binding domains. When several binding domains are introduced, they may be introduced into the Gag polyprotein and/or into the integrase.

The binding domain allows not only recognition of the encapsidation sequence but also encapsidation of the RNAs bearing the encapsidation sequence in the particle (or in the present case, of a non-viral RNA bound to an encapsidation sequence).

By "encapsidation" is meant packaging of RNA in the viral capsid of a viral particle. It should be noted that in the present invention, encapsidation of the non-viral RNAs takes place by recognition of a non-viral encapsidation signal, in particular other than Psi.

By "sequence of interest" is meant a sequence coding or having a function that is of interest for the user. More particularly, the sequence of interest carried by each of the two encapsidated non-viral RNAs may be identical or different.

Using the particles according to the invention, it is possible to transfer identical or different non-viral RNAs into target cells.

As the encapsidated RNAs are non-viral, these RNAs do not have the recognition sites of the proteins encoded by the pol gene.

In fact, these non-viral RNAs do not participate in the early stages of the replication cycle of the retroviruses, namely:
 copying of the single-stranded viral RNA into double-stranded DNA by reverse transcriptase;
 maturation of the double-stranded viral DNA by recognition of the LTR ends by the integrase and maturation of the cytoplasmic pre-integration complex into a nuclear pre-integration complex.

These viral proteins (reverse transcriptase, integrase) encoded by the pol gene are therefore optional in the particle and the pol gene may therefore be either present, or deleted partially or completely. Preferably, the pol gene is either present, or partially deleted.

It should be noted that the retroviral particles according to the invention comprise genetic material that is both viral and non-viral:
 the gag gene, which may be viral or chimeric. More particularly, the gag gene is chimeric when the binding domain(s) is/are introduced into the latter.
 Optionally, the pol gene, which may be viral or chimeric. As the pol gene codes several enzymes, the sequences relating to these enzymes may be deleted completely or partially, present and non-functional, or present and functional. More particularly, the pol gene is chimeric when the binding domain(s) is/are introduced into the integrase.
 At least two non-viral RNAs, each non-viral RNA bearing a sequence of interest and an encapsidation sequence. More particularly, by "non-viral RNA" is meant an RNA lacking any retroviral sequence (which may also be denoted "non-retroviral RNA").

More specifically, the retroviral particles according to the invention make it possible to introduce, into target cells, RNAs capable of inducing:
 the transfer of one or more endogenous or exogenous coding sequences of interest from the target cell,
 the transfer of one or more non-coding RNAs such as RNAs capable of inducing an effect on gene expression, for example by means of shRNA, miRNA, sgRNA, LncRNA or circRNA.
 the transfer of cellular RNAs, of the messenger RNA type or others (miRNA etc.), subgenomic replicons of RNA viruses (HCV, etc.) or of complete genomes of RNA viruses,
 the simultaneous expression of endogenous and exogenous coding or non-coding sequences of the target cell.

More particularly, the viral particles according to the invention make it possible to introduce, into target cells, nucleic acids capable of inducing:
 the expression of one or more epitope(s) and in particular of one or more antigen(s) in cells involved in the immune response (dendritic cells or other antigen-presenting cells);

the activation of the cells transduced to trigger their maturation or their activation or that of cells with which they will be able to interact and counteract, for example the mechanisms of immunosuppression induced by varied and complex mechanisms. Such activation may be carried out by immuno-modulating agents. This type of approach may create a micro-environment favourable to the triggering of an immune response against the tumour cells.

It should be noted that this method may be applied to other types of systems for inducing an immune response.

By "epitope" is meant a structure that can be recognized specifically by an antibody or a lymphocyte receptor.

Advantageously, the sequence of interest codes several epitopes, in particular for an antigen.

By "antigen" is meant a substance that is foreign to the organism and is capable of triggering an immune response with the aim of eliminating it. They may be natural or synthetic. An antigen is generally a natural or synthetic macromolecule, generally proteins, polysaccharides and lipid derivatives thereof. It is the recognition of the antigen by the immunocompetent cells, directly or via the antigen-presenting cells (APCs), that activates specific immunity. One and the same antigen may comprise several epitopes (which may be identical or different) and thus induce a varied immune response. Recognition of the antigen by the lymphocytes depends on the nature of the epitope. The B lymphocytes bind directly to the conformational epitopes through to the immunoglobulins of their membrane. The T lymphocytes recognize the sequential epitopes, corresponding to an amino acid sequence, presented by the antigen-presenting cells.

Preferably, the epitope or the antigen derives from a pathogen, in particular from a virus, a bacterium, a parasite, a tumour cell, etc.

The epitope or the antigen may be deduced from the biomarkers identified as expressed in large quantity on the tumour cells or from viruses or toxins. Its size may be variable. In general, screening is carried out for selecting the best epitope or antigen. The sequence of the deoxyribonucleic acids and ribonucleic acids may be deduced from the protein sequence of the epitope or the antigen.

The epitope is preferably selected from the peptides. More preferably, the epitope is a peptide epitope comprising from 1 to 50 amino acids (AA), preferably less than 30 AA, preferably from 3 to 12 amino acids.

The antigen is preferably selected from peptides, proteins, and glycoproteins. In fact, as the cellular machinery of the cell (host) is able to translate the encapsidated RNA, it can also carry out one or more additional steps of post-translational modifications such as glycosylation. In fact, when production of the antigen takes place in dendritic cells, the antigen may be matured like the biomarker that allowed it to be obtained.

Since the particle according to the invention that allows the introduction of RNA has a size of up to 10 kb, it is possible to introduce antigen sequences of appreciable size into it. However, the size of the antigen sequence is variable. Generally, the larger a molecule, the more it is immunogenic.

By "antigenic sequence" is meant a DNA sequence coding an epitope or an antigen.

Advantageously, the epitope or antigen is immunogenic, i.e. it can initiate an immune response.

By "immunogenic" is meant the potential of an antigen to induce an immune response. A substance may be antigenic without being immunogenic. This potential depends on the species, the degree of similarity between the antigen and the molecules of the host, the physicochemical characteristics of the antigen (size, shape, rigidity) and the dose of antigen received.

Preferably, the epitope is selected from the list constituted by molecules that are identified as recognized by the variable part of an antibody or of a membrane receptor of the T lymphocytes (TCR). The latter are identified and selected according to their immunogenic potential.

Preferably, the antigen is a tumoral antigen, i.e. a molecule specifically present on the surface of the tumour cells, but absent or of low abundance on the surrounding normal cells. More preferably, the antigen is selected from the group constituted by the antigens of the "cancer testis" group (e.g. MAGE-A12, MAGE-A3, MAGE-A10, MAGE-A2, MAGE-A1, CT7/MAGE-C1, CT10, SSX4, BRDT, NY-ESO1, SSX2, Xage1b, MAGE-A4 etc.) which are expressed specifically by the tumoral tissue apart from an ectopic expression by the germ cells; the differentiation antigens, which are expressed in a given tissue both by normal cells and by the corresponding tumour cells; the antigens expressed only in the tumour cells, which may correspond to mutated antigens (Alpha-actinin-4, NY-FC, P53, elongation factor 2, enzyme malic, EGF-R, Kras, Casp8, ACYN4, ALK-EML14 etc.); the neoantigens generated as a result of chromosomal transiocation (Bcr-Abl); the antigens expressed by normal cells that may be overexpressed by the tumour (WT1, ACE, Muc1, Survivin 2B, Telomerase catalytic protein, Her2/neu, EGF-R, EGF, TGFalpha, cyclophilin B etc.); the antigens derived from pathogens, in particular viruses (papillomavirus and uterine cervical cancers or cancers of the upper respiratory and digestive tracts, hepatitis B and C viruses and liver cancers); and the antigens derived from bacteria (*Helicobacter pylori* and stomach cancer) or from parasites (schistosomes and bladder cancer), in particular in humans. In particular, the tumoral antigens associated with melanomas have been classified in three categories depending on whether they are tissue-specific (MART-1, tyrosinases TRP-1 and TRP-2, gp-100), tumour-specific, for those that are also expressed by a great variety of cancers (MAGE-1, NY-ESO-1), or they are mutated unique tumoral antigens (β-catenin, CDC27).

A retroviral particle according to the invention comprising an encapsidated non-viral RNA of which the sequence of interest comprises a part coding code at least one epitope is particularly advantageous for transducing antigen-presenting cells, in particular the dendritic cells.

By "molecular structure specifically recognizing an epitope" or "paratope" Is meant a structure capable of establishing a specific interaction with an epitope, and in particular an antigen. Generally it is an immunoreceptor constituted by the variable part of an antibody or of a membrane receptor of the lymphocytes. Preferably, it is an immunoreceptor of the TCR (T cell receptor) or CAR (chimeric receptor) type present on the surface of a T lymphocyte.

Preferably, the molecular structure specifically recognizing an epitope is selected from the group consisting of the T lymphocyte receptors (TCR), native, modified or chimeric; the B lymphocyte receptors, membrane (BCR) or secreted (immunoglobulins); and the receptors of other cells of the immune system involved in the immune response, such as the NK or NKT lymphocytes.

A retroviral particle according to the invention comprising an encapsidated non-viral RNA the sequence of interest of which comprises a part coding at least one molecular structure specifically recognizing an antigen is particularly advantageous for transducing lymphocytes.

Advantageously, the retroviral particle according to the invention comprises a nucleocapsid protein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the nucleocapsid protein and/or into the integrase.

By "nucleocapsid protein" is meant the structural protein NC encoded by the gag gene. When the binding domain is introduced into the nucleocapsid protein, this protein is a chimeric protein, derived from a chimeric gag gene.

When the binding domain is introduced into the integrase, the integrase is a chimeric protein, derived from a chimeric pol gene.

By "chimeric protein" is meant a recombinant protein comprising several different fused protein sequences.

According to a first embodiment, in the retroviral particle according to the invention, the binding domain is introduced into the nucleocapsid protein and the at least two encapsidated non-viral RNAs differ in their RNA sequence.

This first embodiment allows early, transient expression of the RNAs of interest, without an associated integration event in the genome of the target cells.

In fact, on contacting a particle according to this first embodiment with a target cell, the membrane of the retroviral particle and that of the target cell will fuse and allow release of the particle's contents into the target cell. The RNAs are then released into the cytoplasm and the cellular machinery makes it possible to translate these RNAs into protein(s) directly, i.e. without additional steps such as reverse transcription, translocation into the nucleus or integration into the genome of the target cell.

More particularly, the at least two non-viral RNAs have the same encapsidation sequence. In this case, the at least two encapsidated non-viral RNAs differ in their RNA sequence of interest, i.e. the RNA sequences of interest contained in the two encapsidated non-viral RNAs are different. By "different" is meant sequences of interest that are not identical or have a difference that does not result from a spontaneous mutation or one not intentionally selected by the manipulator.

Alternatively, the at least two non-viral RNAs have two different encapsidation sequences. These at least two encapsidation sequences are then recognized by at least two different binding domains, at least one of these domains being introduced into the nucleocapsid protein. In this case the at least two encapsidated non-viral RNAs may comprise identical or different sequences of interest.

It is possible to encapsidate at least two non-viral RNAs, preferably three non-viral RNAs.

According to a particular embodiment of the first embodiment, a second binding domain is introduced into the nucleocapsid protein of the retroviral particle according to the invention.

By way of example, the second binding domain may be the "Coat" protein of the MS2 bacteriophage when the first binding domain is the "Coat" protein of the PP7 phage or the second binding domain may be the "Coat" protein of the PP7 phage when the first binding domain is the "Coat" protein of the MS2 bacteriophage.

In this case, at least two encapsidated non-viral RNAs bear different encapsidation sequences, each encapsidation sequence corresponding respectively to the first and the second binding domain introduced into the nucleocapsid protein.

More particularly, when three non-viral RNAs are encapsidated:
at least two of the encapsidated non-viral RNAs have the same encapsidation sequence corresponding to the first binding domain and only differ by their RNA sequence of interest,
the third encapsidated non-viral RNA may bear an identical or different encapsidation sequence. When the encapsidation sequence is different, it may correspond to a second binding domain introduced into the nucleocapsid protein.

Other binding domains may also be introduced into the nucleocapsid protein.

Besides the binding domain or domains introduced into the nucleocapsid protein, it is also possible to introduce a binding domain into the integrase.

The integrase is then a chimeric protein, derived from a chimeric pol gene.

Preferably, when the binding domain is introduced into the integrase, the sequence of the integrase is mutated at the level of the C-terminal domain in order to insert the sequence of the binding domain. Even more preferably, the sequence of the integrase is mutated at the level of the C-terminal domain so as to introduce that of the "Coat" protein of the MS2 bacteriophage or of the PP7 phage.

In this case, the at least two encapsidated non-viral RNAs may bear different encapsidation sequences, each encapsidation sequence corresponding to the binding domains introduced into the nucleocapsid protein and into the integrase, respectively.

More particularly, when three non-viral RNAs are encapsidated:
at least two of the encapsidated non-viral RNAs have the same encapsidation sequence corresponding to the first binding domain and only differ by their RNA sequence of interest,
the third encapsidated non-viral RNA bears a different encapsidation sequence, corresponding to a second binding domain introduced into the integrase.

Other binding domains may also be introduced into the integrase.

Advantageously, the retroviral particle according to the invention is a lentiviral particle.

Preferably, in such a lentiviral particle:
the binding domain is the "Coat" protein of the MS2 bacteriophage,
the encapsidation sequence of the non-viral RNAs is a stem-loop sequence of MS2,
the nucleocapsid protein is the nucleocapsid protein (NC) of HIV belonging to the Gag polyprotein, chimeric, the sequence of NC being mutated at the level of the second zinc finger in order to insert the "Coat" protein sequence of the MS2 bacteriophage.

Advantageously:
The envelope protein is the VSV-G protein coding the envelope protein of the vesicular stomatitis virus.
The encapsidation sequence comprises from 2 to 25 repetitions of the MS2 stem-loop sequence, preferably from 6 to 18 repetitions of the stem-loop sequence, even more preferably from 10 to 14, for example 12 repetitions. Preferably, the stem-loop sequence is as follows:

(SEQ ID No. 1)
ctagaaaacatgaggatcacccatgtctgcag.

Or, preferably, in such a lentiviral particle:
the binding domain is the "Coat" protein of the PP7 phage,
the encapsidation sequence of the non-viral RNAs is a PP7 stem-loop sequence,
the nucleocapsid protein is the nucleocapsid protein (NC) of HIV belonging to the Gag polyprotein, chimeric, the sequence of NC being mutated at the level of the second zinc finger in order to insert the "Coat" protein sequence of the PP7 phage.

Advantageously:
The envelope protein is the VSV-G protein coding the envelope protein of the vesicular stomatitis virus.
The encapsidation sequence comprises from 2 to 25 repetitions of the PP7 stem-loop sequence, preferably from 2 to 18 repetitions of the stem-loop sequence, even more preferably from 2 to 12, for example 6 repetitions. Preferably, the stem-loop sequence is as follows:

(SEQ ID No. 2)
ctagaaaggagcagacgatatggcgtcgctccctgcag.

Advantageously, SEQ ID No.2 may be optimized to promote folding of the stem-loop. In particular, it was found that it could be advantageous to insert SEQ ID No.2 and SEQ ID No.3 (ctagaaaccagcagagcatatgggctcgctggctgcag) successively and alternately.

Optionally, the second binding domain introduced into the integrase may be the Coat protein of the PP7 phage if the first binding domain is the Coat protein of the MS2 bacteriophage, or the second binding domain introduced into the integrase may be the Coat protein of the MS2 bacteriophage if the first binding domain is the Coat protein of the PP7 phage.

According to a second embodiment, the invention relates to a retroviral particle comprising a protein derived from the Gag polyprotein, preferably a nucleocapsid protein, an envelope protein, an integrase and at least two encapsidated non-viral RNAs, the encapsidated non-viral RNAs each comprising an RNA sequence of interest bound to an encapsidation sequence, each encapsidation sequence being recognized by a binding domain introduced into the integrase, and optionally by a binding domain introduced into a protein derived from the Gag polyprotein, preferably a nucleocapsid protein.

This second embodiment allows transient expression of the RNA of interest, without an associated integration event in the genome of the target cells.

Preferably, in this second embodiment, the sequence of the integrase is mutated at the level of the C-terminal domain in order to insert the sequence of the binding domain.

Advantageously, the binding domain is a heterologous domain. More particularly, the binding domain is the Coat protein of the MS2 bacteriophage, PP7 phage or Qβ phage, the prophage HK022 Nun protein, the U1A protein or the hPum protein.

Preferably, the sequence of the integrase is mutated at the level of the C-terminal domain so as to introduce that of the "Coat" protein of the MS2 bacteriophage or PP7 phage.

The at least two non-viral RNAs may or may not have the same encapsidation sequence.

Moreover, the at least two encapsidated non-viral RNAs may or may not have the same RNA sequence of interest.

Preferably, the at least two encapsidated non-viral RNAs differ in their RNA sequence of interest, i.e. the RNA sequences of interest contained in the two encapsidated non-viral RNAs are different.

More particularly, the at least two non-viral RNAs have the same encapsidation sequence, the latter being recognized by the binding domain introduced into the integrase.

It is possible to encapsidate at least two non-viral RNAs, preferably three non-viral RNAs.

According to a particular embodiment of the second embodiment, a second binding domain is introduced into the integrase of the retroviral particle according to the invention.

By way of example, the second binding domain may be the "Coat" protein of the MS2 bacteriophage when the first binding domain is the "Coat" protein of the PP7 phage or the second binding domain may be the "Coat" protein of the PP7 phage when the first binding domain is the "Coat" protein of the MS2 bacteriophage.

In this case, at least two encapsidated non-viral RNAs bear different encapsidation sequences, each encapsidation sequence corresponding respectively to the first and the second binding domain introduced into the integrase.

More particularly, when three non-viral RNAs are encapsidated:
at least two of the encapsidated non-viral RNAs have the same encapsidation sequence corresponding to the first binding domain, and these two non-viral RNAs may optionally differ in their RNA sequence of interest,
the third encapsidated non-viral RNA may bear an identical or different encapsidation sequence. When the encapsidation sequence is different, it may correspond to a second binding domain introduced into the integrase.

Other binding domains may also be introduced into the integrase.

Besides the binding domain or domains introduced into the integrase, it is also possible to introduce a binding domain into the nucleocapsid protein.

The nucleocapsid protein is then a chimeric protein, derived from a chimeric gag gene.

In this case, the at least two encapsidated non-viral RNAs may bear different encapsidation sequences, each encapsidation sequence corresponding to the binding domains introduced into the integrase and into the nucleocapsid protein, respectively.

More particularly, when three non-viral RNAs are encapsidated:
at least two of the encapsidated non-viral RNAs have the same encapsidation sequence corresponding to the first binding domain introduced into the integrase, and these non-viral RNAs may optionally differ in their RNA sequence of interest,
the third encapsidated non-viral RNA bears a different encapsidation sequence, corresponding to a second binding domain introduced into the nucleocapsid protein.

Other binding domains may also be introduced into the nucleocapsid protein.

The invention therefore relates to a retroviral particle comprising a nucleocapsid protein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the nucleocapsid protein and/or into the integrase.

Optionally, the sequences of interest of the at least two encapsidated non-viral RNAs may be identical.

Alternatively and preferably, the at least two encapsidated non-viral RNAs in the retroviral particle differ in their RNA sequence.

In this case, it is advantageous for the sequence of interest of the other encapsidated non-viral RNAs to code either for a second epitope or antigen, or for an immunomodulating protein.

In the case when the sequence of interest of the other encapsidated non-viral RNAs codes a second epitope or antigen, it is thus possible to express several epitopes and/or antigens simultaneously and trigger a combined and coordinated immune response. By way of example in the field of tumour immunotherapy, the tumour cells become the target of several independent immune responses.

There are numerous immunomodulating agents, i.e. molecules that may be used for controlling and orienting the immune system. The introduction of these immunomodulating agents by the particles according to the invention may therefore concern all the cells of the immune system (lymphocytes, monocytes) for which it is desired to modulate the specific response, activation or differentiation. In the case of the dendritic cells, these agents carry out two main functions.

In the immature state, the dendritic cells capture the antigen at the level of the targeted or infected tissues and then migrate to the nearest secondary lymphoid organ while differentiating.

In the mature state, the dendritic cells present the antigen to the T lymphocytes in order to activate them specifically.

This specific activation of the dendritic cells leads to the production of cytokines that are essential for setting up and maintaining the immune response. These cytokines make it possible to link the innate system to the adaptive system by a very complex mechanism. That is why activation of the cells in vitro or ex vivo is generally brought about by adding cytokines or factors to the culture medium.

The micro-environment, but also various immunomodulating agents, may induce or contribute to activation of the dendritic cells. For example, the PAMPs (Pathogen Associated Molecular Patterns), the TLRs (Toll-like Receptors), DAMP (Damage associated Molecular pattern Molecules) inflammation molecules may lead to activation of the dendritic cells. Many molecules are capable of activating dendritic cells. The MCM (Monocyte-Conditioned Medium), cytokines (TNFα, IL-1β, PGL6), prostaglandin E2, CD40L or ligands of the TLRs. All of the proteins capable of acting on the activation pathway of the dendritic cells are potentially capable of having a modulating effect on their maturation. In the same way, immunomodulating agents of the T or B lymphocytes may be powerful regulators of the production and activity of these cells and thus stimulate the interactions between the various actors of the immune response and therefore improve the latter.

By "immunomodulating protein" is meant an immunomodulating agent that is in the form of a protein.

This embodiment is particularly advantageous when the antigen-presenting cells and in particular the dendritic cells, or lymphocytes are transduced to express these immunomodulating agents directly and amplify the immune response.

Thus, induction of maturation of the antigen-presenting cells, and in particular of the dendritic cells, concomitant with the expression of an antigen is a particularly promising strategy for inducing an immune response. The objective is to prime the immune system to respond best to the target antigen(s). This priming strategy with the aim of activating the immune system is likely to lead to a reinforcement of the immune response.

Preferably, the immunomodulating protein is selected from the cytokines such as TNFα, IL-1β, PGL6, the interleukins such as IL-2, IL-4, IL-12, IL-15, agents such as GM-CSF, CD28, ICOS ("Inducible Costimulator"), OX40, CD80, ICOSL or OX40L, and proteins for regulating the activation pathways described such as ligands of the TLRs or of the NLRs (Nod-like receptors) such as imiquimod or the CpGs.

Advantageously, the retroviral particle comprises a third encapsidated non-viral RNA.

The third encapsidated non-viral RNA may have a sequence of interest identical to at least one of the sequences of interest of the first two encapsidated non-viral RNAs or differ from each of the sequences of interest of the first two encapsidated non-viral RNAs.

In particular, the retroviral particle may comprise more than three encapsidated non-viral RNAs.

Advantageously, in the case when the particle according to the invention comprises a nucleocapsid protein, the binding domain may be introduced into the nucleocapsid protein, and a second binding domain may be introduced into the nucleocapsid and/or into the integrase.

Alternatively, in the retroviral particle according to the invention, the binding domain may be introduced into the integrase, and a second binding domain may be introduced into the nucleocapsid and/or into the integrase.

Advantageously, the retroviral particle according to the invention is a lentiviral particle.

When the retroviral particle is a lentiviral particle, it is possible to express RNAs of interest transiently, without an associated integration event in the genome of the target cells, in particular of the quiescent cells.

In fact, apart from its role in the integration reaction itself, the integrase (IN) participates in various stages of the replication cycle of the retroviruses such as morphogenesis of the viral particle, reverse transcription and nuclear import of the pre-integration complex (PIC).

More particularly, in the lentiviruses, the integrase contains nuclear localization sequences (NLS) allowing its localization in the nucleus thanks to the PIC. Consequently, when encapsidation of the non-viral RNAs is carried out by a binding domain borne by an integrase of a lentivirus, the encapsidated non-viral RNAs will be transported into the nucleus of the target cell. In fact, on contacting a lentiviral particle according to this second embodiment with a target cell, the membrane of the particle and that of the target cell will fuse and allow release of the contents of the capsid into the target cell. The RNAs are then taken charge of by the integrase which, via the PIC, will allow import of the RNAs into the nucleus. This taking charge is particularly advantageous for certain applications, such as expression in quiescent cells. In the case of retroviral particles, other than the lentiviruses, the integrase does not contain these NLSs and is therefore found to be located in the cytoplasm. It is, however, possible to add, into this type of integrase, NLS sequences in order to induce nuclear localization of the integrase, and therefore of the RNAs taken charge of by this integrase.

This taking charge is also particularly useful for a CRISPR system, which makes use of guide RNAs that will hybridize specifically to the genome of the target cell. Once hybridized, these guide RNAs guide an endonuclease (Cas9), which will allow modification of a specific locus of the target cell genome.

For immunotherapy, the fact that the transduction is carried out in particular by lentiviral particles allows a transient expression of the RNAs transduced.

The particle according to the invention is consequently capable of delivering multiple RNAs, optionally genetically distinct, without an integration event in the genome of the host cells in order to express on the one hand multiple different tumoral antigen sequences for example, and on the other hand immunomodulating proteins capable of triggering activation of the cells transduced in the immune response mechanism.

More particularly, in such a lentiviral particle:
the binding domain is the "Coat" protein of the MS2 bacteriophage,
the encapsidation sequence of the non-viral RNAs is a stem-loop sequence of MS2,
the integrase is an enzymatic chimeric protein the sequence of which is mutated at the level of the C-terminal domain in order to insert the "Coat" protein sequence of the MS2 bacteriophage.

Or, more particularly, in such a lentiviral particle:
the binding domain is the "Coat" protein of the PP7 phage,
the encapsidation sequence of the non-viral RNAs is a PP7 stem-loop sequence,
the integrase is an enzymatic chimeric protein the sequence of which is mutated at the level of the C-terminal domain in order to insert the "Coat" protein sequence of the PP7 phage.

Optionally, the second binding domain introduced into the nucleocapsid may be the Coat protein of the PP7 phage if the first binding domain is the Coat protein of the MS2 bacteriophage or the second binding domain introduced into the integrase may be the Coat protein of the MS2 bacteriophage if the first binding domain is the Coat protein of the PP7 phage.

In fact, the integrase (IN) is composed of 3 distinct functional domains, each indispensable for ensuring a complete integration reaction. The N-terminal domain contains a zinc finger type motif that stabilizes the folded structure of the IN and increases the catalytic activity of the enzyme. The central domain of the IN contains the DDE amino acid motif, to which the catalytic activity of the enzyme is attributed. This central domain is also involved in the recognition of the nucleotide sequence conserved at each end of the retroviral DNA. The C-terminal domain is the least conserved in the retrovirus family. It has DNA binding activity and is indispensable for the reactions of maturation of the 3' ends for strand transfer. Apart from its role in the integration reaction itself, IN participates in various stages of the replication cycle of the retroviruses such as morphogenesis of the viral particle, reverse transcription and nuclear import of the pre-integration complex.

As described by Petit et al. (1999; J. Virol. P5079-5088), insertion of an exogenous sequence at C-terminal of the IN does not disturb the steps of production and transduction of target cells whereas a same insertion at N-terminal does not allow detection of a transduction event.

The retroviral particle was therefore modified to contain the "Coat" protein of the MS2 bacteriophage fused with the protein of the integrase (FIG. 1) or the "Coat" protein of the PP7 phage (FIG. 37). The p8.74 encapsidation plasmid, which bears the pol gene coding the integrase protein, is modified in order to insert the sequence coding the Coat protein at C-terminal of the integrase by assembly PCR. The p8.74 plasmid is linearized by PCR and then the Coat sequence, amplified beforehand by PCR, is cloned at the C-terminal level of the integrase, either directly end-to-end or with the addition of a linker.

Advantageously:
The envelope protein is the VSV-G protein coding the envelope protein of the vesicular stomatitis virus.
The encapsidation sequence comprises from 2 to 25 repetitions of the stem-loop sequence of MS2 and/or of PP7, depending on the binding domain introduced, preferably from 2 to 18 repetitions, more preferably from 2 to 18 repetitions, such as from 6 to 18 repetitions of the stem-loop sequence, even more preferably for the stem-loop sequence of MS2, from 10 to 14, for example 12 repetitions.
Preferably, the stem-loop sequence is as follows: ctagaaaacatgaggatcacccatgtctgcag (SEQ ID No.1) when the binding domain is the Coat protein of MS2 and/or the stem-loop sequence is as follows: ctagaaaggagcagacgatatggcgtcgctccctgcag (SEQ ID No.2) and/or the stem-loop sequence SEQ ID No.2 alternating with the stem-loop sequence SEQ ID No.3 when the binding domain is the Coat protein of PP7.

Several examples of lentiviral particle according to the invention are described below, and some are described in more detail in the examples given hereunder
an RLP or MS2RLP or MS2 (NC)-RLP 12× particle is a lentiviral particle formed by encapsidation of RNAs bearing the stem-loop motif of the MS2 bacteriophage, repeated 12 times, by insertion of the Coat protein of the MS2 bacteriophage into the nucleocapsid,
an MS2 (NC)-RLP 2× particle is a lentiviral particle formed by encapsidation of RNAs bearing the stem-loop motif of the MS2 bacteriophage, repeated 2 times, by insertion of the Coat protein of the MS2 bacteriophage into the nucleocapsid,
an MS2 (NC)-RLP 6× particle is a lentiviral particle formed by encapsidation of RNAs bearing the stem-loop motif of the MS2 bacteriophage, repeated 6 times, by insertion of the Coat protein of the MS2 bacteriophage into the nucleocapsid,
an MS2 (IN)-RLP 2× particle is a lentiviral particle formed by encapsidation of RNAs bearing the stem-loop motif of the MS2 bacteriophage, repeated 2 times, by insertion of the Coat protein of the MS2 bacteriophage into the integrase,
an MS2 (IN)-RLP 6× particle is a lentiviral particle formed by encapsidation of RNAs bearing the stem-loop motif of the MS2 bacteriophage, repeated 6 times, by insertion of the Coat protein of the MS2 bacteriophage into the integrase,
an MS2 (IN)-RLP 12× particle is a lentiviral particle formed by encapsidation of RNAs bearing the stem-loop motif of the MS2 bacteriophage, repeated 12 times, by insertion of the Coat protein of the MS2 bacteriophage into the integrase,
a PP7RLP or PP7 (NC)-RLP 2× particle is a lentiviral particle formed by encapsidation of RNAs bearing the stem-loop motif of the PP7 phage, repeated 2 times, by insertion of the Coat protein of the PP7 phage into the nucleocapsid,
a PP7 (NC)-RLP 6× particle is a lentiviral particle formed by encapsidation of RNAs bearing the stem-loop motif of the PP7 phage, repeated 6 times, by insertion of the Coat protein of the PP7 phage into the nucleocapsid,
a PP7 (NC)-RLP 12× particle is a lentiviral particle formed by encapsidation of RNAs bearing the stem-loop motif of the PP7 phage, repeated 12 times, by insertion of the Coat protein of the PP7 phage into the nucleocapsid, a PP7 (IN)-RLP 2× or PP7 (IN)-RLP particle is a lentiviral particle formed by encapsidation of RNAs bearing the stem-loop motif of the PP7 phage, repeated 2 times, by insertion of the Coat protein of the PP7 phage into the integrase, a PP7 (IN)-RLP 6× particle is a lentiviral particle formed by encapsidation of RNAs bearing the stem-loop motif of the PP7 phage, repeated 6 times, by insertion of the Coat protein of the PP7 phage into the integrase, a PP7 (IN)-RLP 12× particle is a lentiviral particle formed by encapsidation of RNAs bearing the stem-loop motif of the PP7 phage, repeated 12 times, by insertion of the Coat protein of the PP7 phage into the integrase, an MS2/PP7RLP or MS2/PP7(NC)-RLP 12× 2× particle is a lentiviral particle formed by encapsidation of RNAs bearing the stem-loop motif of the MS2 bacteriophage, repeated 12 times, by insertion of the Coat protein of the MS2 bacteriophage into the nucleocapsid, or bearing the stem-loop motif of the PP7 phage, repeated 2 times, by insertion of the Coat protein of the PP7 phage into the nucleocapsid.

Preferably, the lentiviral particle formed by encapsidation of RNAs bears a stem-loop motif of the MS2 bacteriophage or of the PP7 phage, repeated from 2 to 25 times, more preferably 2, 6 or 12 times.

Even more preferably, the particle according to the invention is selected from MS2 (NC)-RLP 12×, PP7 (NC)-RLP 6×, PP7 (NC)-RLP 2×, MS2 (IN)-RLP 12×, PP7 (IN)-RLP 6× and PP7 (IN)-RLP 2×.

The invention also relates to compositions comprising particles according to the invention.

More particularly, the compositions according to the invention are concentrated compositions. Advantageously, the compositions are also purified. These compositions may be concentrated and purified by the method described in application WO2013/014537.

Typically, the compositions according to the invention comprise less than 30% of DNA contaminants and less than 45% of protein contaminants with respect to the crude supernatant. More particularly, the compositions according to the invention comprise less than 30% of DNA contaminants and less than 2% of protein contaminants with respect to the crude supernatant.

By "crude supernatant" is meant the supernatant cell culture(s), comprising retroviral particles according to the invention, after clarifying. Such a clarifying step is more particularly described below in the methods for manufacturing the particles according to the invention. When the recovery of the supernatant is carried out several times, the crude supernatant then corresponds to all of the supernatants collected, combined (or "pooled") and then clarified.

Optionally, the compositions according to the invention comprise less than 1% of DNA contaminants and less than 1% of protein contaminants with respect to the crude supernatant.

The invention also relates to kits for producing particles according to the invention and to the manufacturing methods for these kits.

More particularly, the invention relates to a kit for producing particles according to the invention, comprising:
(i) an expression plasmid comprising at least one sequence of interest, for which an encapsidation sequence is inserted upstream or downstream of said sequence, (ii) an encapsidation plasmid coding a protein derived from the Gag polyprotein and/or a chimeric integrase, comprising a binding domain allowing recognition of an encapsidation sequence, and
(iii) an envelope plasmid coding an envelope protein.

Such a kit may also comprise instructions for use of the plasmids contained in the kit.

More specifically, when the kit is for producing particles according to the first embodiment, this kit comprises:
(i) an expression plasmid comprising at least two different non-viral RNA sequences, each RNA sequence comprising a sequence of interest for which an encapsidation sequence is inserted upstream or downstream of said sequence of interest, or alternatively a first and a second expression plasmid each comprising a sequence of interest, upstream or downstream of which an encapsidation sequence is inserted,
(ii) an encapsidation plasmid coding a chimeric nucleocapsid protein comprising a binding domain allowing recognition of the encapsidation sequence, and
(iii) an envelope plasmid coding an envelope protein.

The at least two non-viral RNA sequences are different because the sequences of interest are different and/or the encapsidation sequences are different.

As a plasmid is a DNA structure, it is well known that by "expression plasmid comprising at least two non-viral RNA sequences" is meant an expression plasmid coding at least two non-viral RNA sequences.

In fact, the expression plasmids in the kits contain all the DNA sequences necessary for obtaining at least one non-viral RNA by transcription. The expression plasmid contains at least one promoter, followed by a DNA sequence of interest (cDNA or DNA that will be transcribed into a non-viral RNA) and an encapsidation sequence (a DNA coding example for MS2 or PP7 repeat motifs) and optionally an RNA stabilizing sequence.

Preferably, the kit for producing the particles according to the first embodiment comprises:
(i) an expression plasmid comprising at least two sequences of interest, for which an encapsidation sequence is inserted upstream or downstream of each of these sequences, or alternatively a first and a second expression plasmid each comprising a sequence of interest, upstream or downstream of which an encapsidation sequence is inserted, the sequences of interest being different and the encapsidation sequences being identical,
(ii) an encapsidation plasmid coding a chimeric nucleocapsid protein comprising a binding domain allowing recognition of the encapsidation sequence, and
(iii) an envelope plasmid coding an envelope protein.

Advantageously, the kit produces lentiviral particles.

Preferably:

In the expression plasmid, the encapsidation sequence comprises from 2 to 25 repetitions of the stem-loop sequence of MS2, preferably from 6 to 18 repetitions of the stem-loop sequence, even more preferably from 10 to 14, for example 12 repetitions. Advantageously, the stem-loop sequence is as follows: ctagaaaacatgaggatcacccatgtctgcag (SEQ ID No.1).

In the encapsidation plasmid, the nucleocapsid protein is the nucleocapsid protein (NC) of HIV belonging to the Gag polyprotein, said NC is mutated at the level of the second zinc finger in order to insert the sequence of the "Coat" protein of the MS2 bacteriophage.

In the envelope plasmid, the envelope protein is the VSV-G protein coding the envelope protein of the vesicular stomatitis virus.

Or, preferably:

In the expression plasmid, the encapsidation sequence comprises from 2 to 25 repetitions stem-loop sequence of PP7, preferably from 2 to 18 repetitions of the stem-loop sequence, even more preferably from 2 to 12, for example 6 repetitions. Advantageously, the stem-loop sequence is as follows: ctagaaaggagcagacgatatggcgtcgctccctgcag (SEQ ID No.2) and/or the stem-loop sequence SEQ ID No.2 alternating with the stem-loop sequence SEQ ID No.3.

In the encapsidation plasmid, the nucleocapsid protein is the nucleocapsid protein (NC) of HIV belonging to the Gag polyprotein, said NC is mutated at the level of the second zinc finger in order to insert the sequence of the "Coat" protein of the PP7 phage.

In the envelope plasmid, the envelope protein is the VSV-G protein coding the envelope protein of the vesicular stomatitis virus.

Optionally, the kit comprises a second encapsidation plasmid coding a chimeric integrase comprising a binding domain allowing recognition of an encapsidation sequence. The second binding domain may be identical to or different from the binding domain of the chimeric nucleocapsid protein.

By way of examples of various binding domains:
the binding domain introduced into the nucleocapsid may be the Coat protein of MS2 and the binding domain introduced into the integrase may be the Coat protein of PP7, or
the binding domain introduced into the nucleocapsid may be the Coat protein of PP7 and the binding domain introduced into the integrase may be the Coat protein of MS2.

Several binding domains may be introduced into each of the chimeric proteins.

Alternatively, when the kit is for producing particles according to the second embodiment, this kit comprises:
(i) an expression plasmid comprising at least one sequence of interest, for which an encapsidation sequence is inserted upstream or downstream of this sequence,
(ii) an encapsidation plasmid coding a chimeric integrase comprising a binding domain allowing recognition of the encapsidation sequence, and,
(iii) an envelope plasmid coding an envelope protein.

Advantageously, the production kits according to the invention may further comprise a second encapsidation plasmid coding:
a protein derived from the wild-type Gag polyprotein, when the first encapsidation plasmid codes a protein derived from the chimeric Gag polyprotein, and/or
a wild-type integrase, when the first encapsidation plasmid codes a chimeric integrase.

Manufacturing methods for the kits according to the invention are also proposed. Typically, a method for manufacturing a kit according to the invention comprises:
(i) preparing an expression plasmid comprising at least one sequence of interest, for which an encapsidation sequence is inserted upstream or downstream of this sequence
(ii) preparing an encapsidation plasmid coding a protein derived from the Gag polyprotein and/or a chimeric integrase, comprising a binding domain allowing recognition of an encapsidation sequence, and (iii) preparing an envelope plasmid coding an envelope protein.

More specifically, when the method relates to a kit for producing the particles according to the first embodiment, it comprises:
(i) preparing an expression plasmid comprising at least two different non-viral RNA sequences, each RNA sequence comprising a sequence of interest for which an encapsidation sequence is inserted upstream or downstream of this sequence of interest, or alternatively a first and a second expression plasmid each comprising a sequence of interest, upstream or downstream of which an encapsidation sequence is inserted,
(ii) preparing an encapsidation plasmid coding a chimeric nucleocapsid protein comprising a binding domain allowing recognition of the encapsidation sequence, and,
(iii) preparing an envelope plasmid coding an envelope protein.

The at least two non-viral RNA sequences are different because the sequences of interest are different and/or the encapsidation sequences are different.

Preferably, this method comprises:
(i) preparing an expression plasmid comprising at least two sequences of interest, for which an encapsidation sequence is inserted upstream or downstream of each of these sequences, or alternatively a first and a second expression plasmid each comprising a sequence of interest, upstream or downstream of which an encapsidation sequence is inserted, the sequences of interest being different and the encapsidation sequences being identical,
(ii) preparing an encapsidation plasmid coding a chimeric nucleocapsid protein comprising a binding domain allowing recognition of the encapsidation sequence, and
(iii) preparing an envelope plasmid coding an envelope protein.

Alternatively, when the method relates to a kit for producing the particles according to the second embodiment, this method comprises:
(i) preparing an expression plasmid comprising at least one sequence of interest, for which an encapsidation sequence is inserted upstream or downstream of this sequence,
(ii) preparing an encapsidation plasmid coding a chimeric integrase comprising a binding domain allowing recognition of the encapsidation sequence, and,
(iii) preparing an envelope plasmid coding an envelope protein.

The invention also relates to methods for manufacturing the particles according to the invention.

Such a method comprises a step of co-transfection of cells with:
(i) an expression plasmid comprising at least one sequence of interest, for which an encapsidation sequence is inserted upstream or downstream of this sequence,
(ii) an encapsidation plasmid coding a protein derived from the Gag polyprotein and/or a chimeric integrase comprising a binding domain allowing recognition of an encapsidation sequence, and,
(iii) an envelope plasmid coding an envelope protein.

and recovery of the supernatant of the transfected cells comprising the particles.

The cells utilized in the manufacturing methods for particles according to the invention are producer cells, i.e. cells which, once transfected with the plasmids bearing the genetic material necessary for formation of the retroviral particles, allow formation of said particles. By way of example of producer cells, HEK293T may be mentioned.

By "step of co-transfection" is meant a step of transfection during which transfection is carried out by bringing the producer cells into contact with all of the plasmids of the method for manufacturing the particles.

More specifically, when the aim of the manufacturing method is to produce particles according to the first embodiment, it comprises a step of co-transfection of cells with:
  (i) an expression plasmid comprising at least two different non-viral RNA sequences, each RNA sequence comprising a sequence of interest for which an encapsidation sequence is inserted upstream or downstream of this sequence of interest, or alternatively a first and a second expression plasmid each comprising a sequence of interest, upstream or downstream of which an encapsidation sequence is inserted,
  (ii) an encapsidation plasmid coding a chimeric nucleocapsid protein comprising a binding domain allowing recognition of the encapsidation sequence, and,
  (iii) an envelope plasmid coding an envelope protein,
and recovery of the supernatant of the transfected cells comprising the particles.

The at least two non-viral RNA sequences are different because the sequences of interest are different and/or the encapsidation sequences are different.

Preferably, this method of manufacturing particles comprises a step of co-transfection of cells with:
  (i) an expression plasmid comprising at least two sequences of interest, for which an encapsidation sequence is inserted upstream or downstream of each of these sequences, or alternatively a first and a second expression plasmid each comprising a sequence of interest, upstream or downstream of which an encapsidation sequence is inserted, the sequences of interest being different and the encapsidation sequences being identical,
  (ii) an encapsidation plasmid coding a chimeric nucleocapsid protein comprising a binding domain allowing recognition of the encapsidation sequence, and,
  (iii) an envelope plasmid coding an envelope protein,
and recovery of the supernatant of the transfected cells comprising the particles.

Alternatively, when the aim of the manufacturing method is to produce particles according to the second embodiment, this method comprises a step of co-transfection of cells with:
  (i) an expression plasmid comprising at least one sequence of interest, for which an encapsidation sequence is inserted upstream or downstream of this sequence,
  (ii) an encapsidation plasmid coding a chimeric integrase comprising a binding domain allowing recognition of the encapsidation sequence, and,
  (iii) an envelope plasmid coding an envelope protein,
and recovery of the supernatant of the transfected cells comprising the particles.

Preferably, all of the methods for manufacturing particles according to the invention are carried out by the methods described in application WO2013/014537.

More particularly, these manufacturing methods for particles are carried out on producer cells cultured in a medium without serum, and no induction with sodium butyrate is carried out.

Advantageously, the supernatant is collected several times, for example between 3 and 6 times, at specific time intervals, such as time intervals of the order of the half-life of the retroviral particles. Typically, recovery of the supernatant is carried out 4 to 5 times, at time intervals of the order of 6 to 18 h, preferably from 8 to 16 h, such as 8 h, 12 h and/or 16 h. Preferably, this collection is carried out after changing the culture medium of the cells, this changing preferably being carried out at 24 h post-transfection.

The manufacturing methods for the particles according to the invention also comprise a step in which the supernatant is clarified.

Preferably, the supernatant is clarified by centrifugation.

Even more preferably, these manufacturing methods for the particles according to the invention further comprise a step in which the supernatant is concentrated and/or purified.

Preferably, concentration and purification are carried out by frontal ultrafiltration on centrifugation units.

Advantageously, the supernatant undergoes one or more additional purification steps. These purification steps are preferably carried out by tangential ultrafiltration and/or diafiltration. Even more preferably, the supernatant undergoes a step of tangential ultrafiltration followed by a step of diafiltration.

Tangential ultrafiltration is advantageously carried out with polysulphone hollow-fibre cartridges.

Optionally, the composition may then undergo a step of ion exchange chromatography, in particular anion exchange chromatography. The eluate from this chromatography step is recovered and then concentrated again by frontal ultrafiltration on central centrifugation units. A composition resulting from such a method comprises less than 1% of DNA contaminants and less than 1% of protein contaminants with respect to the crude supernatant.

In the manufacturing method according to the invention, the co-transfection step may in addition be carried out with a second encapsidation plasmid coding:
  a protein derived from the wild-type Gag polyprotein, when the first encapsidation plasmid codes a protein derived from the chimeric Gag polyprotein, and/or
  a wild-type integrase, when the first encapsidation plasmid codes a chimeric integrase.

Advantageously, the ratio of the second encapsidation plasmid to the first encapsidation plasmid is in the range from [10:90] to [60:40], preferably in the range from [20:80] to [50:50].

Advantages connected with the use of a second encapsidation plasmid and more particularly with the ratios defined above are described more fully in Example 8.

The invention also relates to compositions that can be obtained by any one of the manufacturing methods for the particles according to the invention.

Typically, these compositions comprise less than 30% of DNA contaminants and less than 45% of protein contaminants with respect to the crude supernatant. More particularly, the compositions according to the invention comprise less than 30% of DNA contaminants and less than 2% of protein contaminants with respect to the crude supernatant.

Optionally, the compositions according to the invention comprise less than 1% of DNA contaminants and less than 1% of protein contaminants with respect to the crude supernatant.

Finally, the invention relates to the use of a particle according to the invention, or of a composition according to the invention for the transduction of cells, and in particular cells involved in the immune response.

Use of the particles and compositions according to the invention is particularly advantageous for the transduction of primary cells and immortalized lines, in order to modify them transiently. The cells may be mammalian cells or cells of other eukaryotes. In particular, the transduction of these cells may be carried out in vivo, in vitro or ex vivo.

The cells involved in the immune response are in particular the antigen-presenting cells (APCs) and the cells of the immune system. More particularly they are monocytes (dendritic cells, macrophages), T or B lymphocytes, Natural Killers and haematopoietic stem cells.

These particles or compositions may be described as "vaccines" and have the aim of inducing effector T cells specific to cancer or to viruses for reducing the size of tumours or eradicating viral development as well as for inducing memory T cells that will be able to prevent loss of control of the tumour or virus.

Introduction of multiple heterogeneous nucleic acids into a target cell is a major challenge in research & development and in therapy for applications in vitro, ex vivo and in vivo.

The invention will be better understood in light of the following examples given by way of illustration, with reference to the figures, which show respectively:

FIG. 11A is a schematic diagram of the construction of the expression cassette derived from the expression plasmid bearing, as RNA sequence of interest, a complete antigen sequence coding the MAGE A3 antigen, this expression plasmid being used for the production of MS2RLP lentiviral particles according to the invention;

FIG. 11B is a schematic diagram of the construction of the expression cassette derived from the expression plasmid bearing, as RNA sequence of interest, a partial antigen sequence coding the MAGE A3 antigen (PS-MageA3 or PS-MAGEA3), this expression plasmid being used for the production of MS2RLP lentiviral particles according to the invention;

FIG. 11C is a schematic diagram of the construction of the expression cassette derived from the expression plasmid bearing, as RNA sequence of interest, a partial antigen sequence coding the gp100 antigen (PS-gp100 or PS-GP100), this expression plasmid being used for the production of MS2RLP lentiviral particles according to the invention;

FIG. 11D is a schematic diagram of the construction of the expression cassette derived from the expression plasmid bearing, as RNA sequence of interest, a partial antigen sequence coding tyrosinase (PS-Tyr or PS-TYR), this expression plasmid being used for the production of MS2RLP lentiviral particles according to the invention;

Figure 19:
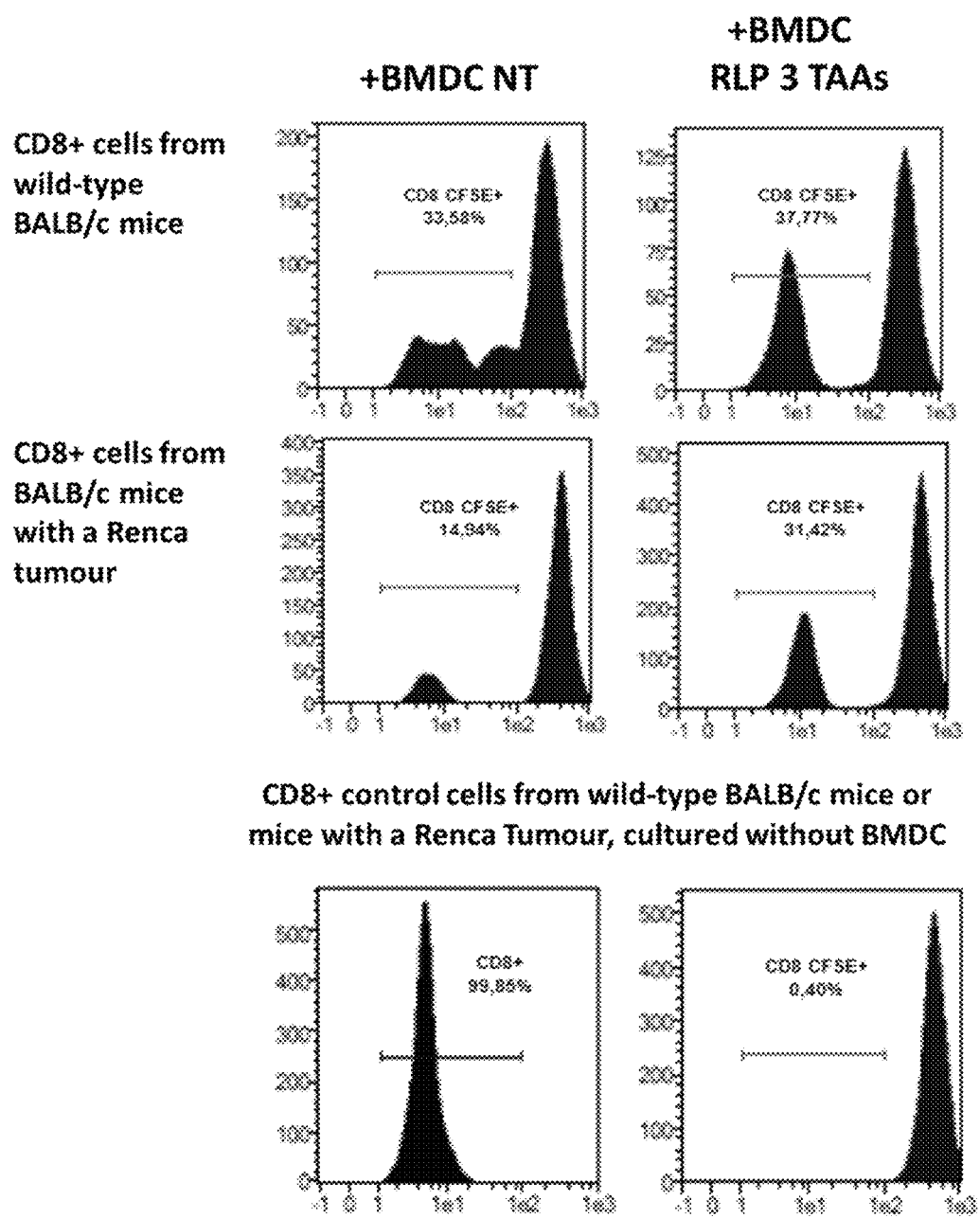
Figure 20:
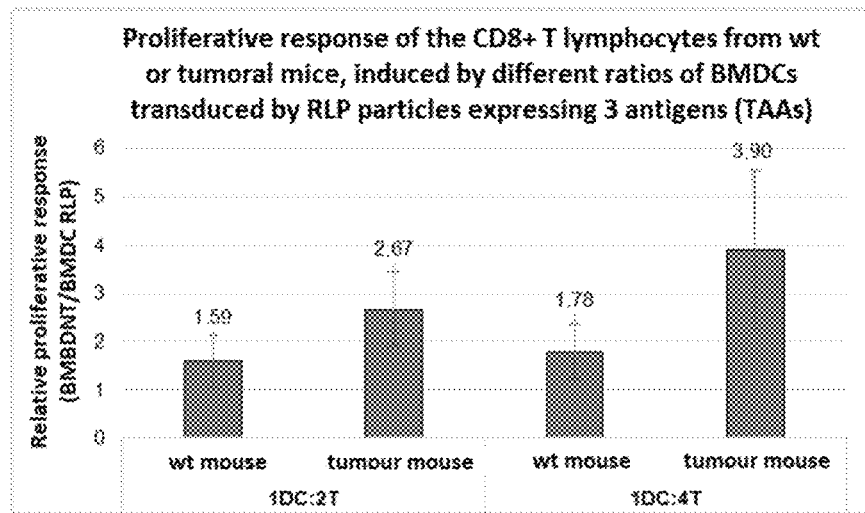
Figure 21:
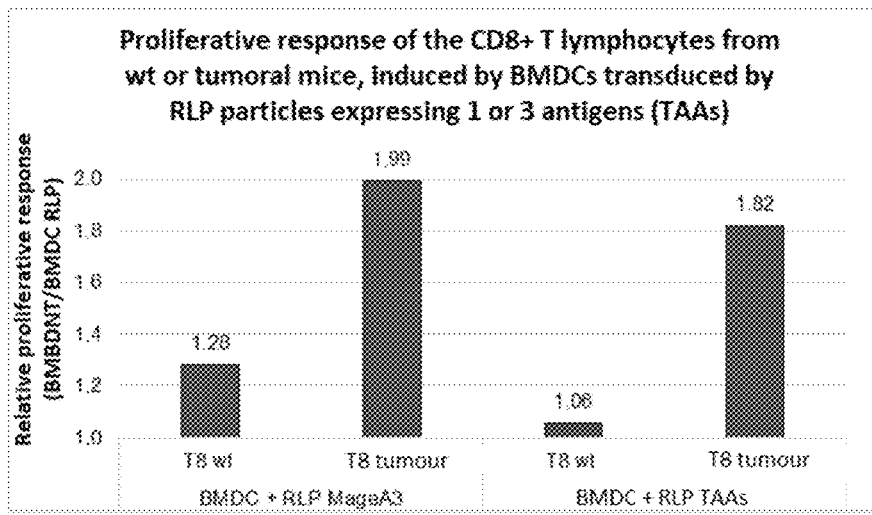
Figure 22:
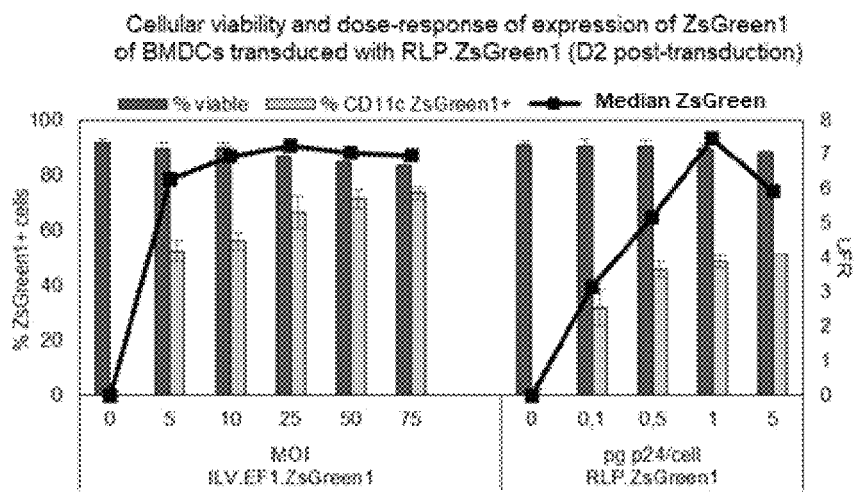
Figure 23:
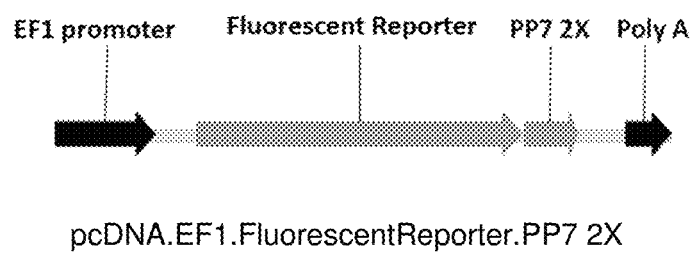
Figure 24:
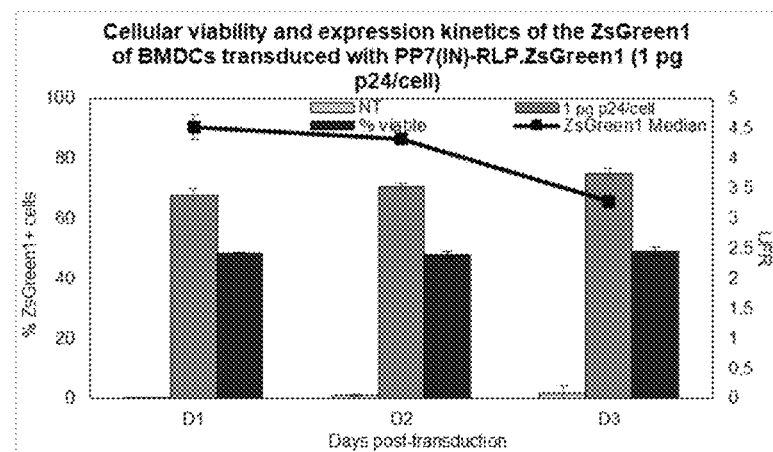
Figure 25:
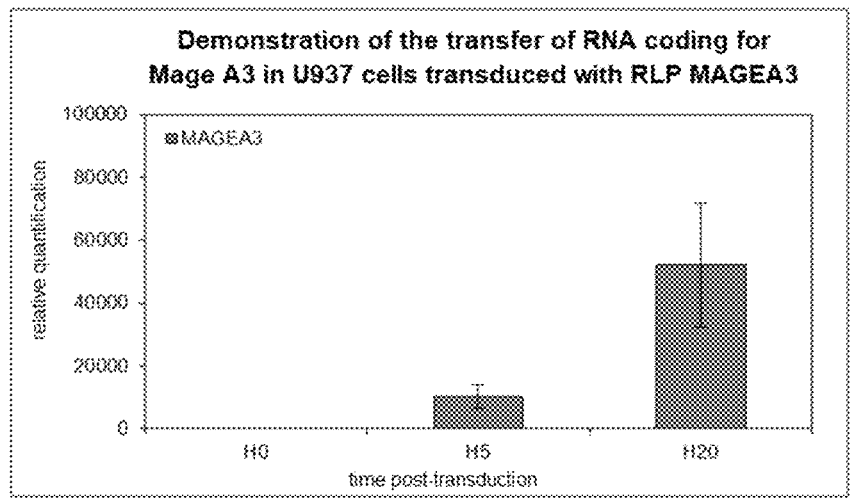
Figure 26:
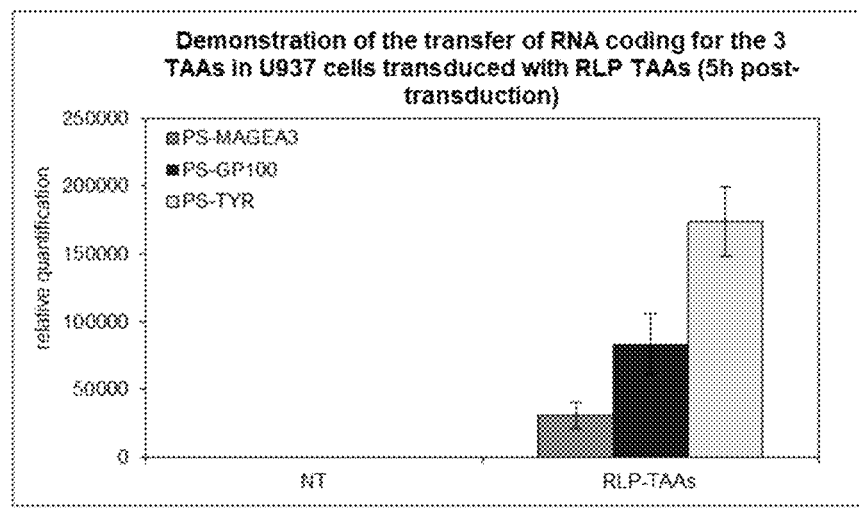
Figure 27:
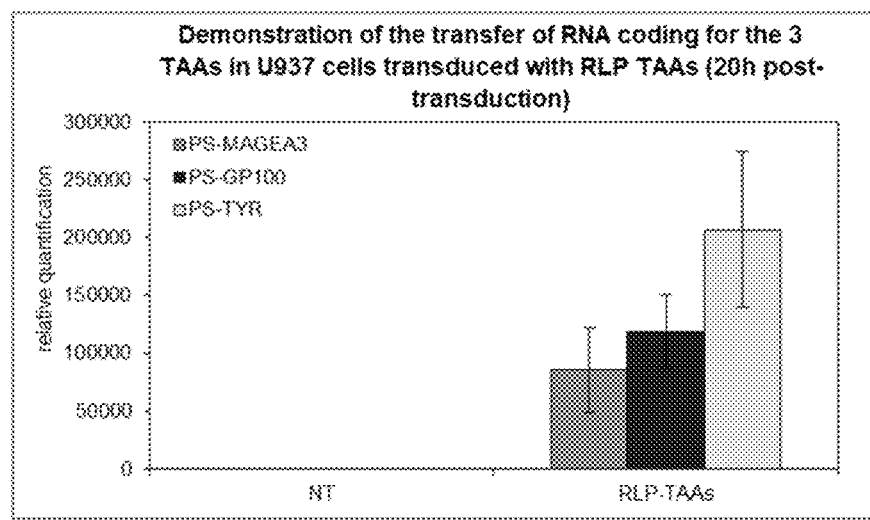
Figure 28:
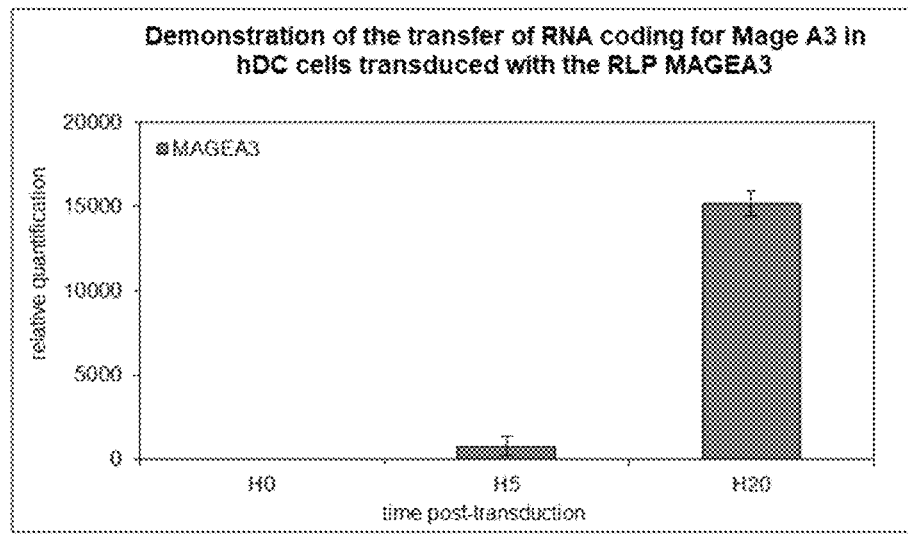
Figure 29:
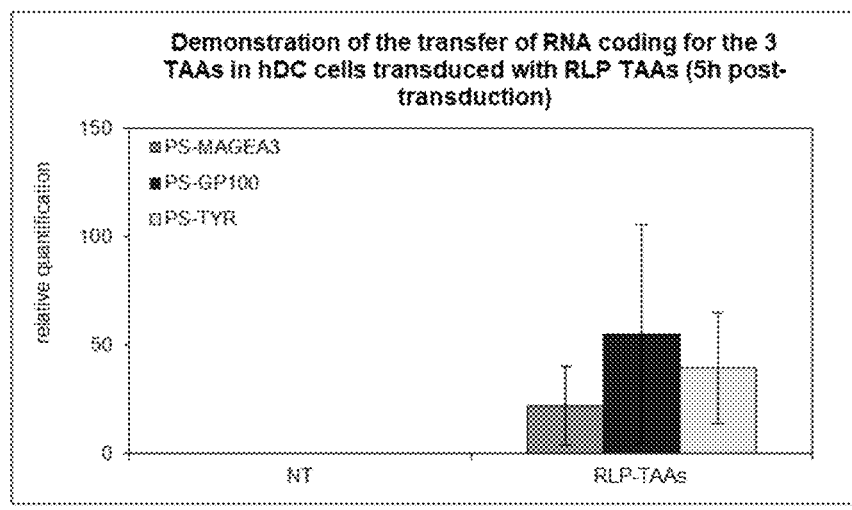
Figure 30:
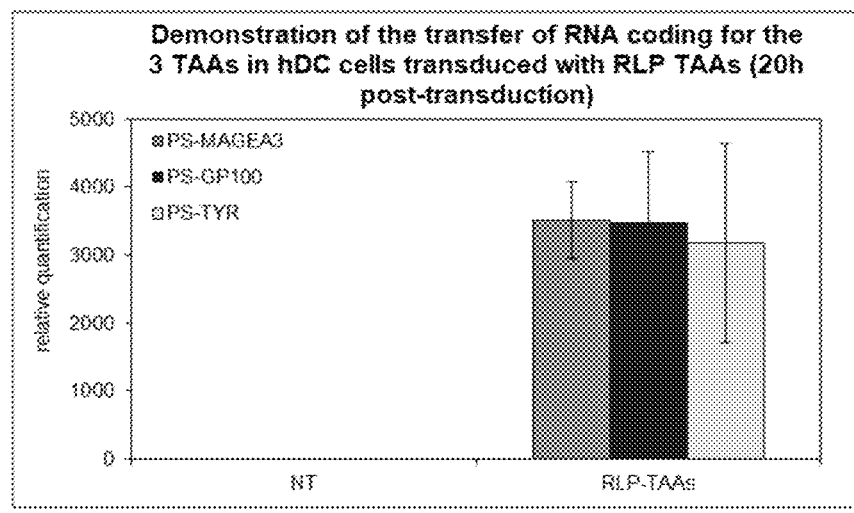
Figure 31:
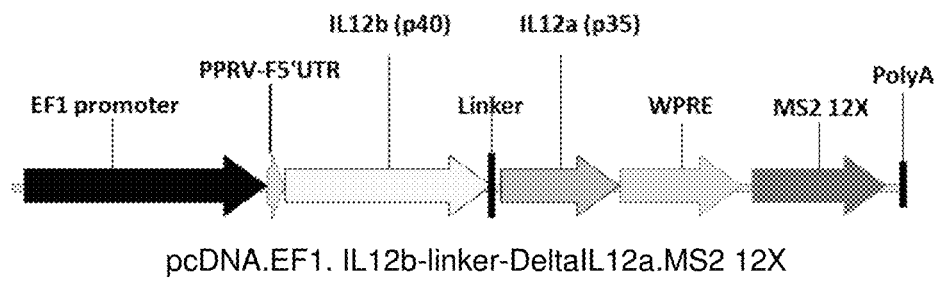
Figure 32:
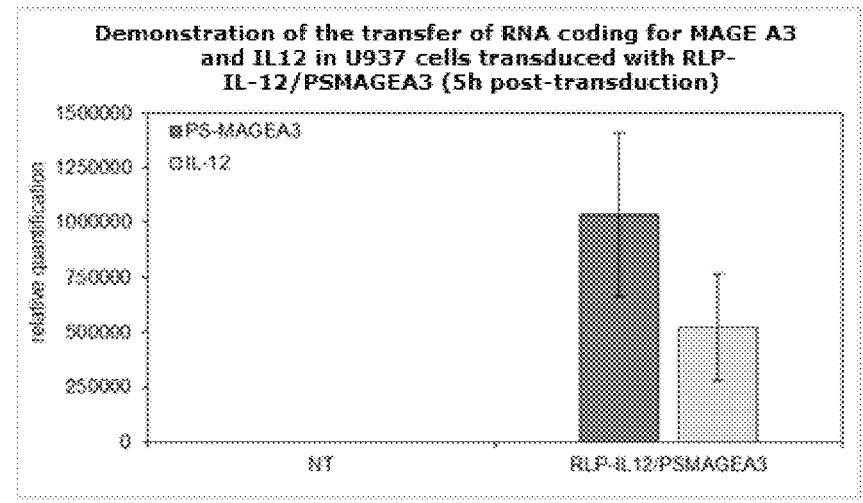
Figure 33:
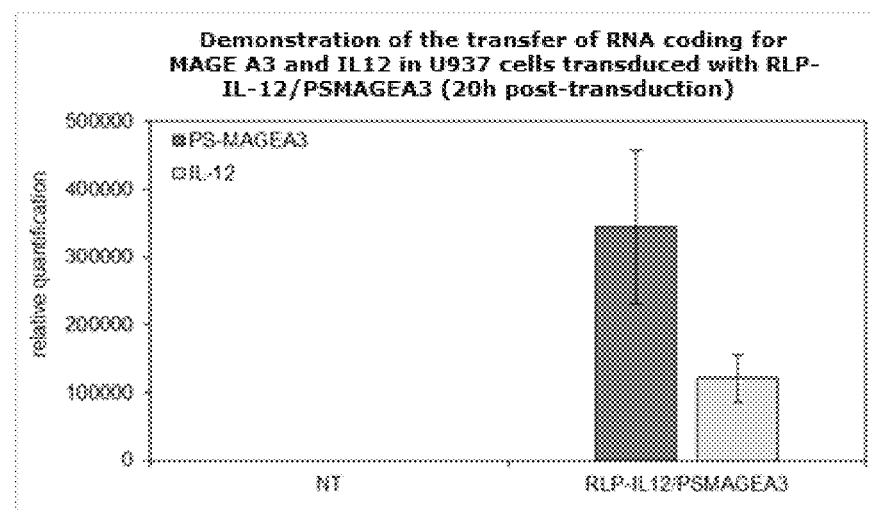
Figure 34:
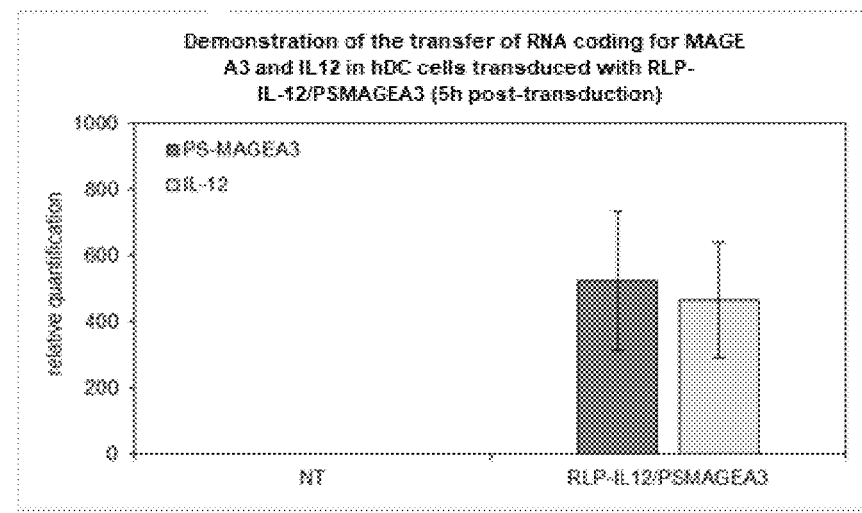
Figure 35:
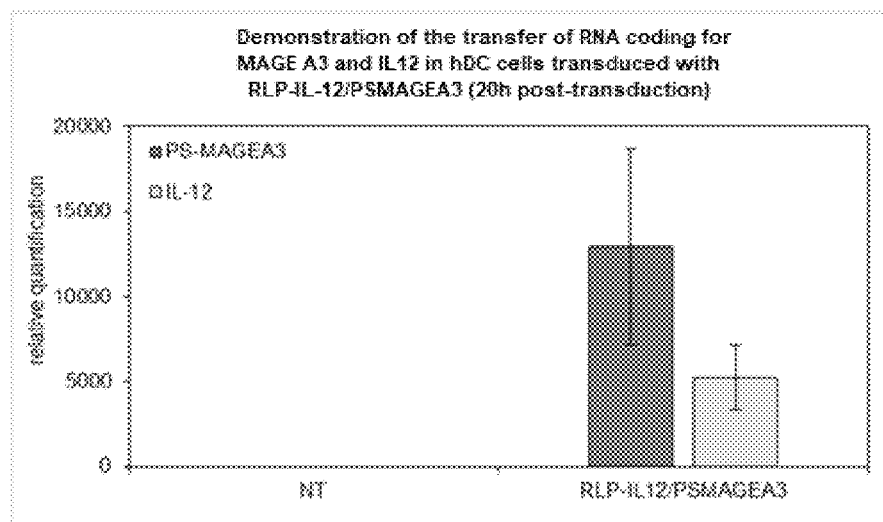
Figure 36:
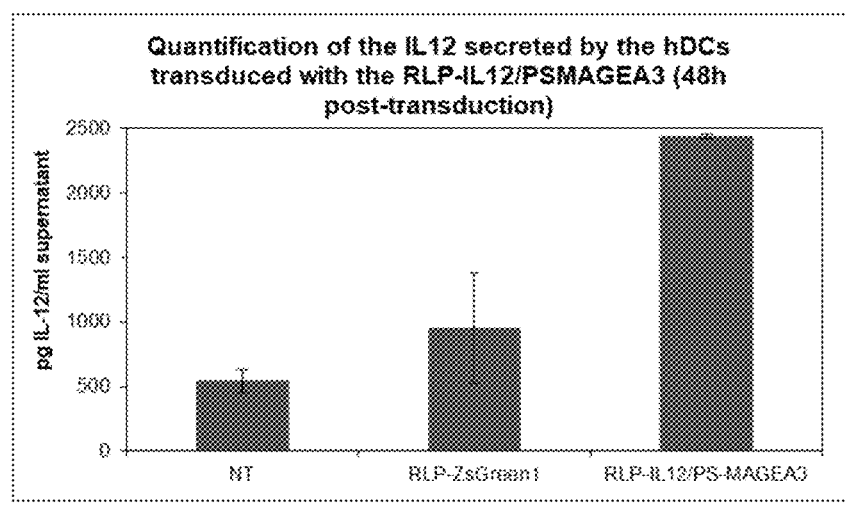
Figure 37:
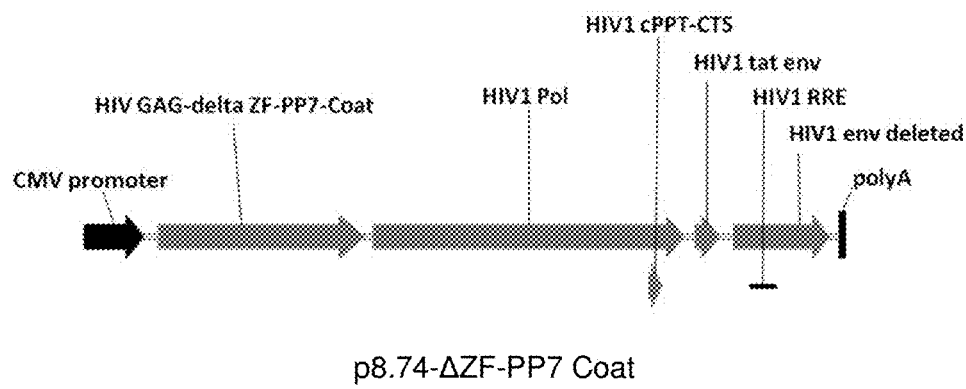
Figure 38:
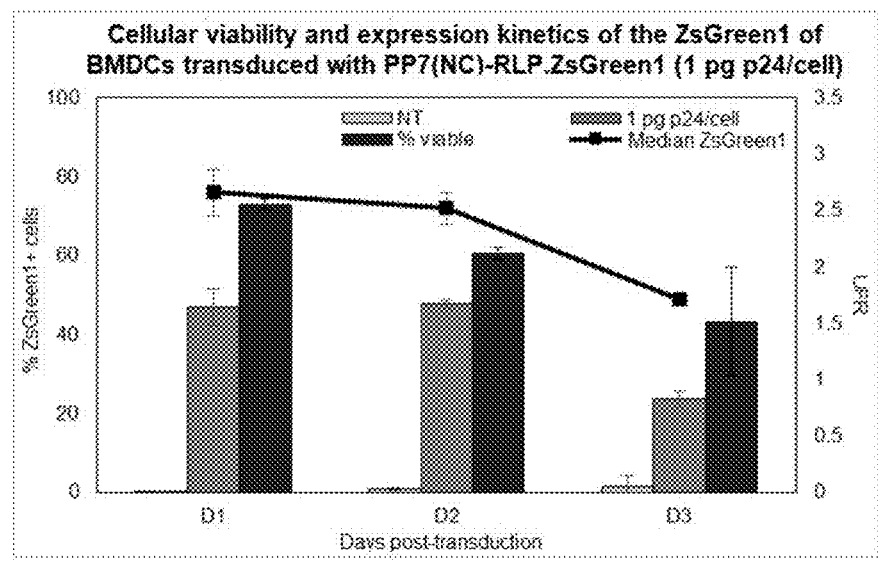
Figure 39:
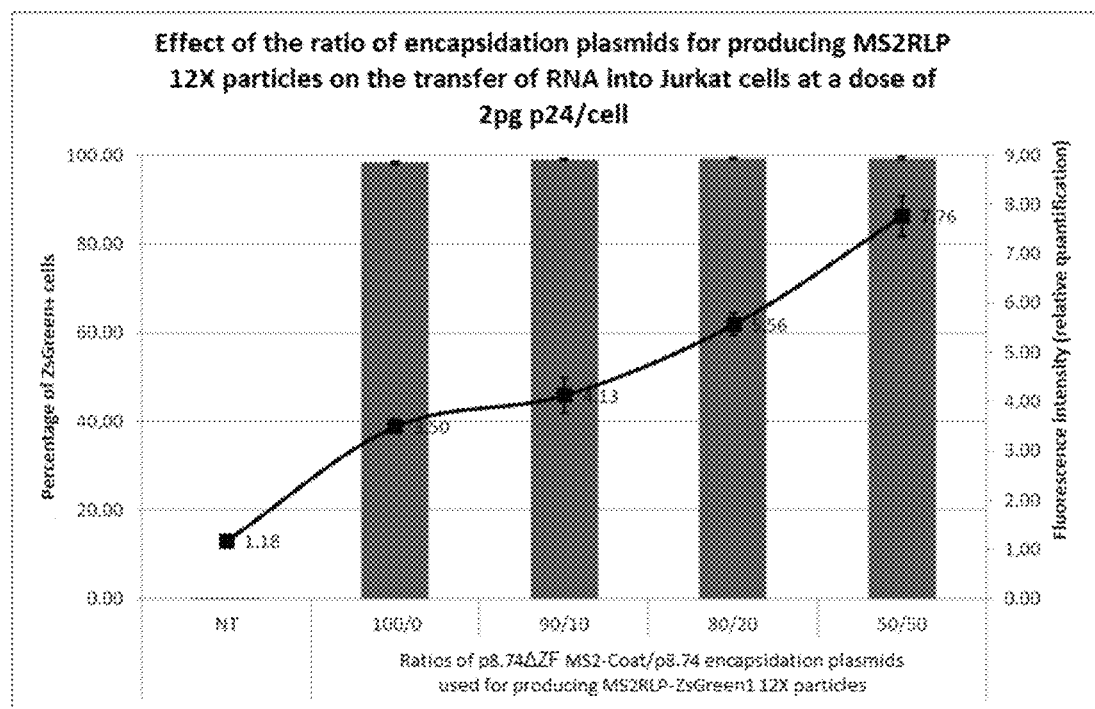
Figure 40:
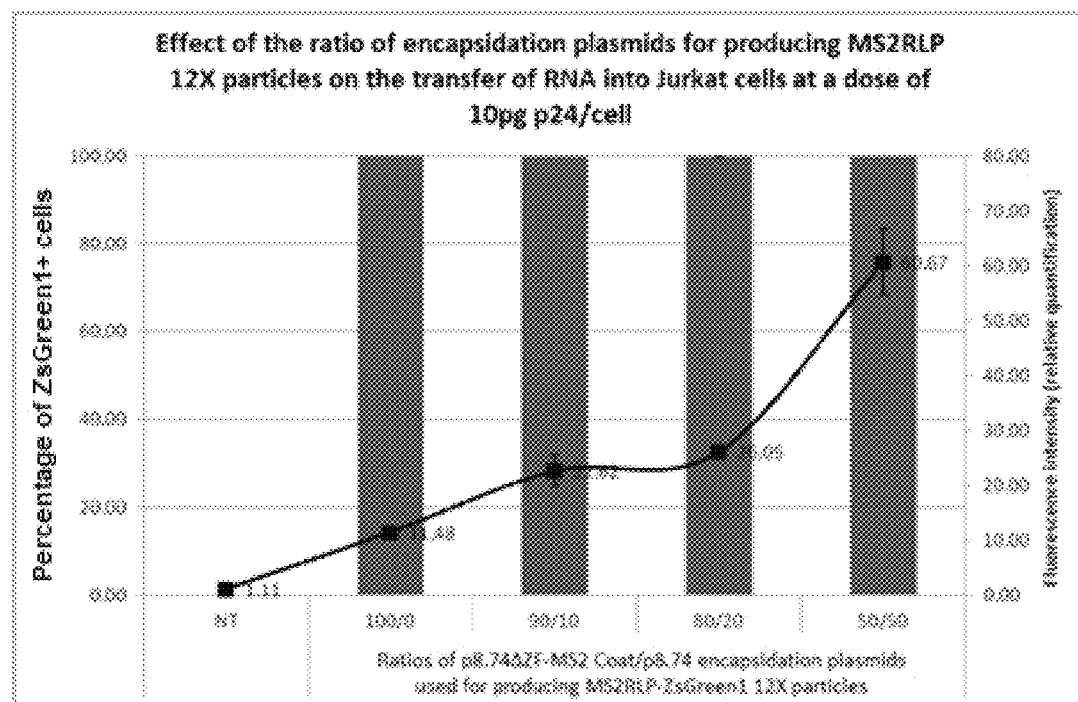
Figure 41A:
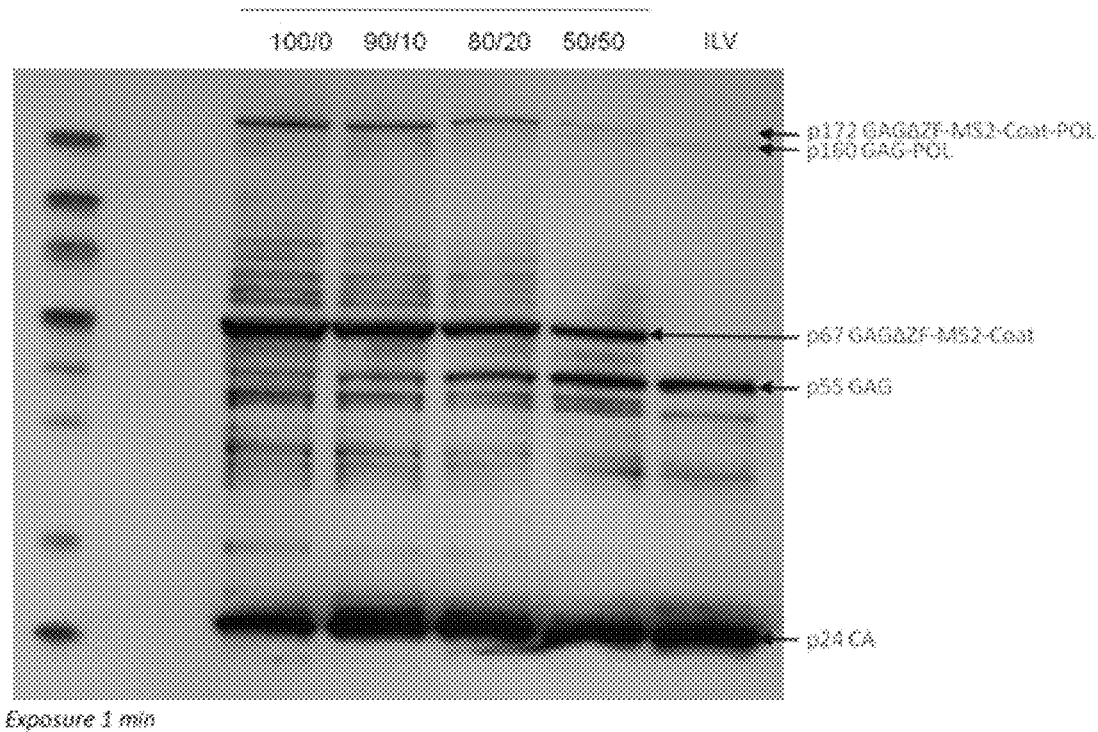
Figure 41B:
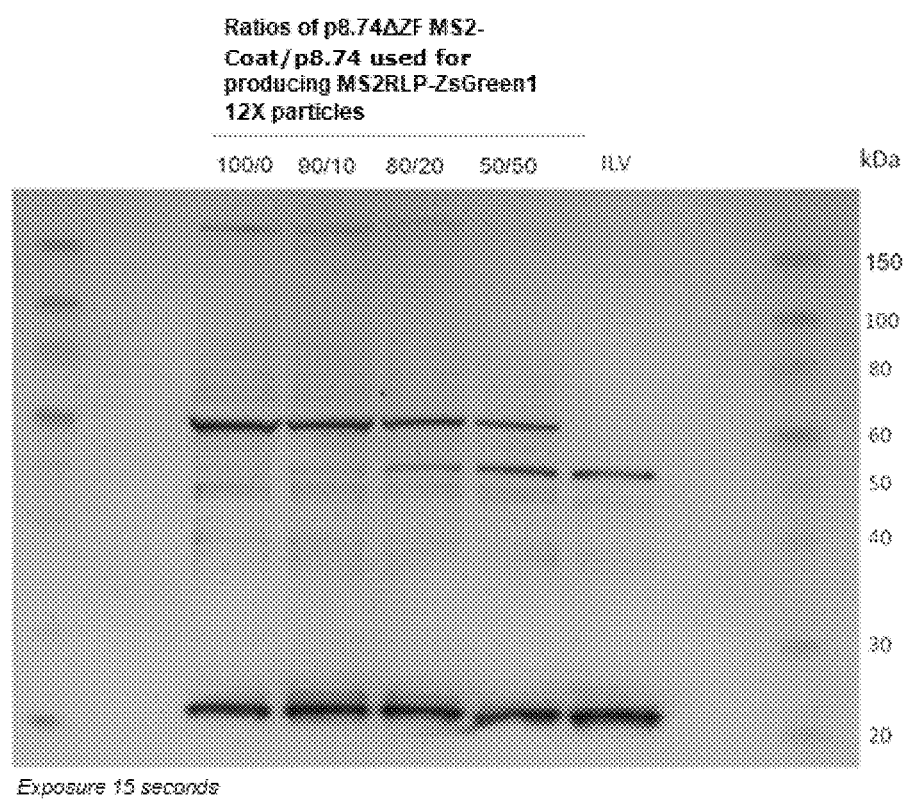
Figure 42:
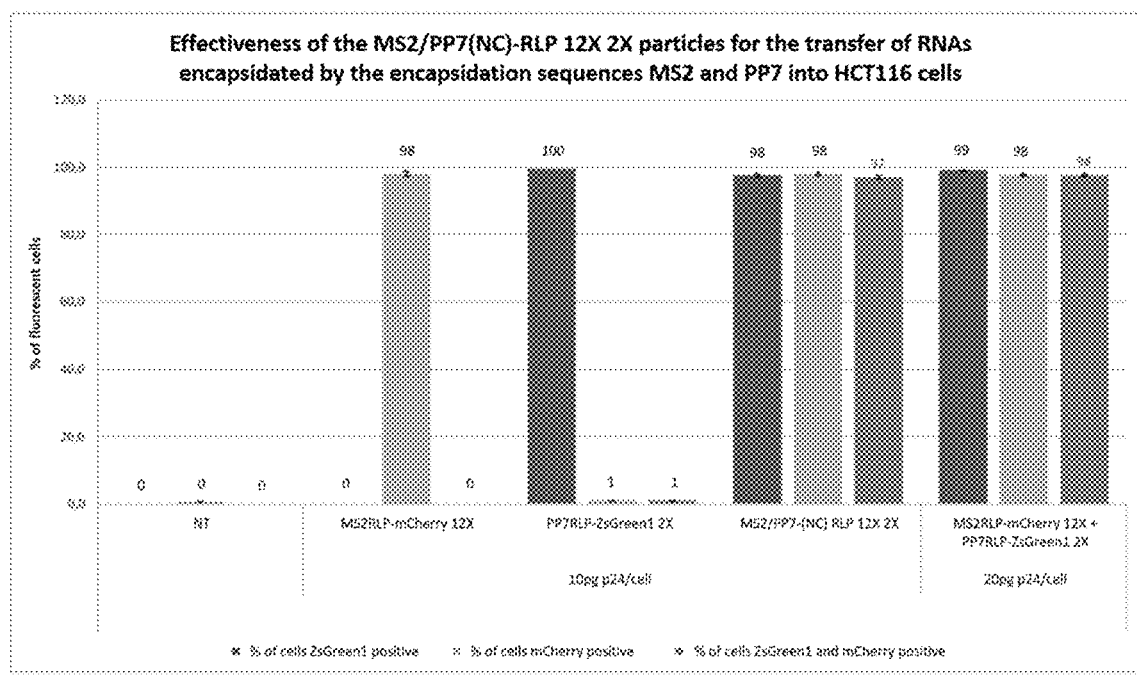

FIG. 19 shows the expression profiles of the murine CD8 marker and of CFSE obtained with CFSE-labelled CD8+ cells cultured alone for 5 days (control, at the bottom), as well as those obtained with CD8+ cells derived from spleens of BABUc mice, wild-type (at the top) or that have developed a tumour (in the middle), labelled with CFSE, then co-cultured for 5 days with BMDCs, non-transduced (on the left) or transduced (on the right) with the RLP-PS-MAGEA3/Gp100/Tyr particles; the results are expressed as percentage of cells that have proliferated;

FIG. 20 is a diagram illustrating the relative proliferative response of the CFSE-labelled CD8+ cells co-cultured with BMDCs, non-transduced or transduced with the RLP-PS-MAGEA3/Gp100/Tyr particles; the results of co-cultures at ratios of 1DC:2T and 1DC:4T are shown; the results are given as the ratio of the percentage of cells proliferating in response to contact with the BMDCs transduced with the RLP-PS-MAGEA3/Gp100/Tyr particles to the percentage of the cells responding non-specifically to the non-transduced BMDCs. (n=3 experiments);

FIG. 21 is a diagram illustrating the results of an experiment comparing the relative proliferative responses of CD8+ cells co-cultured at a ratio of 1DC:2T with BMDCs transduced by RLP.MAGE A3.IRES.GFP particles or transduced by the RLP-PS-MAGEA3/Gp100/Tyr particles;

FIG. 22 is a diagram illustrating the cellular viability and the dose-response of expression of ZsGreen1 of BMDCs transduced with RLP.ZsGreen1;

FIG. 23 shows the schematic diagram of the expression cassette derived from an expression plasmid bearing a fluorescent reporter as the RNA sequence of interest, used for the production of PP7 (NC)-RLP and PP7 (IN)-RLP lentiviral particles according to the invention;

FIG. 24 is a diagram illustrating the cellular viability and the expression kinetics of ZsGreen1 of BMDCs transduced with PP7 (IN)-RLP.ZsGreen1 at a dose of 1 pg p24/cell;

FIG. 25 is a diagram illustrating the demonstration of the transfer of RNA coding MAGEA3 into U937 cells transduced with RLP MAGEA3, at 5 h post-transduction and at 20 h post-transduction;

FIG. 26 is a diagram illustrating the demonstration of the transfer of RNA coding the 3 TAAs (PS-MAGEA3, PS-GP100, PS-TYR), into U937 cells transduced with the RLP TAAs (tumour-associated antigens or tumoral antigens) (PS-MAGEA3, PS-GP100, PS-TYR), at 5 h post-transduction;

FIG. 27 is a diagram illustrating the demonstration of the transfer of RNA coding the 3 TAAs (PS-MAGEA3, PS-GP100, PS-TYR), into U937 cells transduced with the RLP TAAs (PS-MAGEA3, PS-GP100, PS-TYR), at 20 h post-transduction;

FIG. 28 is a diagram illustrating the demonstration of the transfer of RNA coding MAGEA3 into hDC cells transduced with RLP MAGEA3, at 5 h post-transduction and at 20 h post-transduction;

FIG. 29 is a diagram illustrating the demonstration of the transfer of RNA coding the 3 TAAs (PS-MAGEA3, PS-GP100, PS-TYR) into hDC cells transduced with the RLP TAAs (PS-MAGEA3, PS-GP100, PS-TYR), at 5 h post-transduction;

FIG. 30 is a diagram illustrating the demonstration of the transfer of RNA coding the 3 TAAs (PS-MAGEA3, PS-GP100, PS-TYR) into hDC cells transduced with the RLP TAAs (PS-MAGEA3, PS-GP100, PS-TYR), at 20 h post-transduction;

FIG. 31 shows the schematic diagram of the expression cassette derived from the expression plasmid bearing, as RNA sequence of interest, the immunomodulating protein IL12, formed by the two subunits IL12b (p40) and IL12a (p35), used for the production of MS2RLP lentiviral particles according to the invention;

FIG. 32 is a diagram illustrating the demonstration of the transfer of RNA coding MAGEA3 and IL12 into U937 cells transduced with RLP-IL-12/PSMAGEA3, at 5 h post-transduction;

FIG. 33 is a diagram illustrating the demonstration of the transfer of RNA coding MAGEA3 and IL12 Into U937 cells transduced with RLP-IL-12/PSMAGEA3, at 20 h post-transduction;

FIG. 34 is a diagram illustrating the demonstration of the transfer of RNA coding MAGEA3 and IL12 into hDC cells transduced with RLP-IL-12/PSMAGEA3, at 5 h post-transduction;

FIG. 35 is a diagram illustrating the demonstration of the transfer of RNA coding MAGEA3 and IL12 into hDC cells transduced with RLP-IT-12/PSMAGEA3, at 20 h post-transduction;

FIG. 36 is a diagram illustrating the quantification of the immunomodulating protein IL12, secreted by the hDCs transduced with RLP-IL12/MAGEA3 (48 h post-transduction);

FIG. 37 shows a schematic diagram of the construction of the expression cassette derived from the p8.74 lentiviral encapsidation plasmid in which a binding domain PP7 Coat has been introduced into the nucleocapsid sequence, this encapsidation plasmid being used for the production of PP7RLP lentiviral particles according to the invention;

FIG. 38 is a diagram illustrating the cellular viability and the expression kinetics of ZsGreen1 of BMDCs transduced with RLP-PP7(NC).ZsGreen1 at a dose of 1 pg p24/cell;

FIG. 39 is a diagram illustrating the effect of the wild-type GAG-POL precursor for the production of MS2RLP 12× particles on the transfer of RNA into Jurkat cells at a dose of 2 pg p24/cell;

FIG. 40 is a diagram illustrating the effect of the wild-type GAG-POL precursor for the production of MS2RLP 12× particles on the transfer of RNA into Jurkat cells at a dose of 10 pg p24/cell;

FIG. 41 illustrates the analysis of the maturation of the MS2RLP viral particles by anti-p24 Western blot after 15 seconds (FIG. 41B) and 1 minute (FIG. 41A); and FIG. 42 is a diagram illustrating the effectiveness of the MS2/PP7-(NC) RLP 12× 2× particles for transferring RNAs encapsidated by the MS2 and PP7 encapsidation sequences into HCT116 cells.

In the following examples, all of the transduction assays are carried out with integrative lentiviral vectors (ILV) or with lentiviral particles bearing RNAs (RLP) carrying genetic material coding a fluorescent protein. As the RLP particles are non-integrating, the titre of the batches is determined as physical particles per millilitre (PP/ml) whereas for the integrative lentiviral vectors the titre is expressed conventionally in transduction units per millilitre (TU/ml). Thus, the multiplicity of infection (MOI) with the RLP particles is expressed in PP or pg of p24 protein per cell and the MOI with the ILV vectors is expressed in TU/ml. The transduction assays are carried out for each type of vectors, taking care to avoid saturating conditions, and favouring conditions making it possible to visualize a dose effect for each type of particles. It is important to remember that the two types of products RLP and ILV are serum-free products so as to minimize the production of toxic proteins in the supernatant by favouring sequential recovery of the virions. Once clarified, the supernatants are concentrated and purified by tangential ultrafiltration so as to obtain high purity.

EXAMPLE 1

Transduction of Cells of the Immune System by the Viral Particle According to the Invention and Comparison of the Transduction Effectiveness with Other Systems I. Preparation of the Viral Particle According to the Invention and of the Comparative Systems
1. Plasmid Construction
1.1 Plasmids for Producing MS2RLP Lentiviral Particles According to the Invention
  Expression plasmid for a sequence of interest: The expression plasmid bears a promoter-sequence of interest-polyA expression cassette with or without an intron sequence or RNA-stabilizing sequence. In order to transport the mRNAs into the lentiviral particles, 12 repetitions of the stem-loop motif of the MS2 RNA (ctagaaaacatgaggatcacccatgtctgcag, SEQ ID No.1) were inserted within an expression cassette downstream of the reporter gene. The promoter used may be the CMV or EF1 promoter but other promoters may be used. The sequence of interest may be a DNA coding a reporter protein such as native firefly luciferase, a green (ZsGreen1), red (mCherry) or blue (mtBFP) fluorescent protein (the expression cassette of which is as described in FIG. 1). The sequence of interest may be a cDNA coding a protein, for example an immunogenic protein or an immunomodulating protein. The sequence of interest may also be that of a cDNA, shRNA, miRNA, sgRNA, LncRNA or circRNA.

Encapsidation plasmid: The lentiviral particle was modified to contain the "Coat" protein sequence of the MS2 bacteriophage in the nucleocapsid protein, in place of the second Zn finger domain. The p8.74 encapsidation plasmid, bearing the genes coding the structural and functional proteins (Gag, Pol), used for producing the MS2RLP particles, is modified in accordance with the following strategy: this p8.74 plasmid is used for generating, by assembly PCR, a plasmid lacking the second zinc finger of the p8.74ΔZF nucleocapsid protein. The second zinc finger is substituted with the Coat protein of the MS2 phage by HpaI cloning, to generate the plasmid p8.74ΔZF-MS2-Coat (the expression cassette of which is as described in FIG. 2). The Pol coding sequence may be deleted or mutated in certain functional elements for example such as the sequence coding reverse transcriptase (RT) or integrase (IN) without altering the function of the MS2RLPs.

Envelope plasmid (pENV): This plasmid bears the gene coding an envelope protein, which may be for example the sequence of the VSV-G gene coding the envelope protein of the vesicular stomatitis virus (the expression cassette of which is as described in FIG. 3).

Figure 4A:
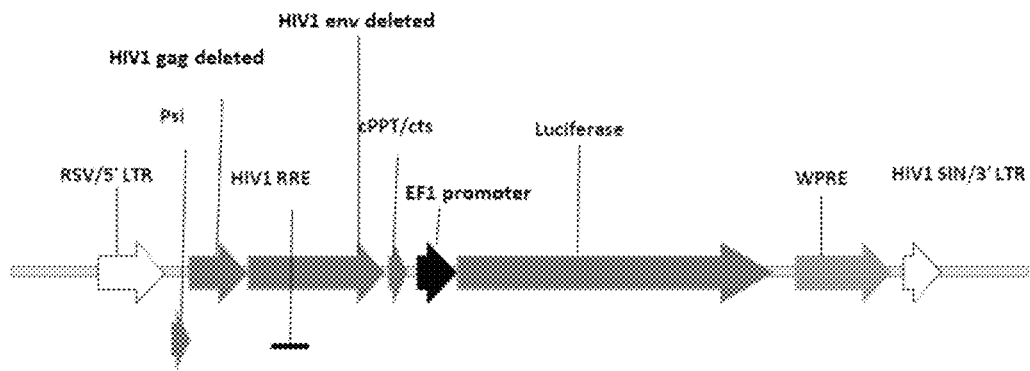
FIG. 4 shows three schematic diagrams of the construction of the expression cassette derived from the integrating lentiviral expression plasmid bearing, as sequence of interest, luciferase (FIG. 4A), a fluorescent gene (FIG. 4B) or Cre (FIG. 4C)
Figure 4B:
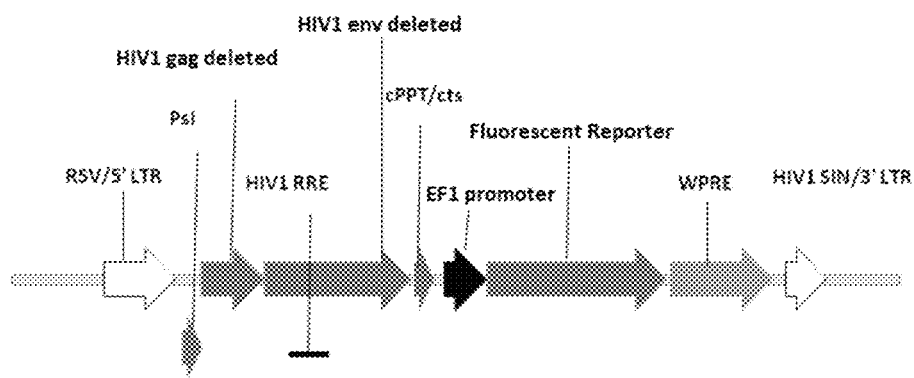
Figure 4C:
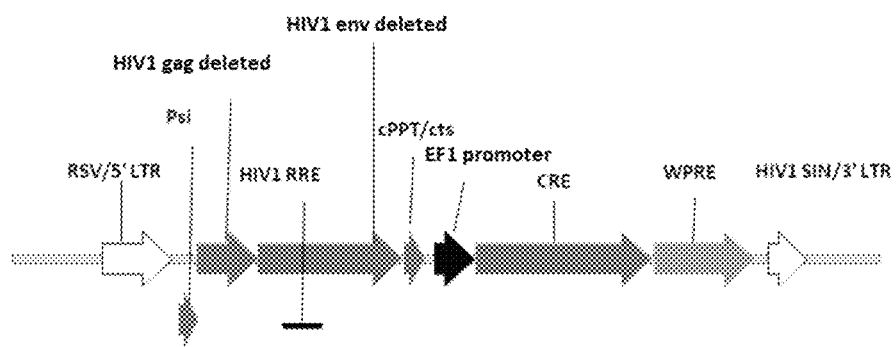

1.2 Plasmids for Producing Integrative Lentiviral Vectors ILV
Expression plasmid for a sequence of interest: The expression plasmid bears a promoter-sequence of interest expression cassette. The sequence of the gene of interest may be for example that of luciferase (FIG. 4A), of a fluorescent reporter (FIG. 4B) or of CRE recombinase (FIG. 4C). This plasmid may contain other elements such as the native sequence WPRE (Woodchuck Hepatitis Virus Post-transcriptional Regulatory Element) or the sequence cPPT/CTS. Viral pathogenicity is eliminated by substitution of regions of the viral genome required for retroviral replication by the transgene.

Encapsidation plasmid: The p8.74 encapsidation plasmid bearing the genes coding the structural and functional proteins (Gag, Pol) is used for producing the integrative lentiviral vectors (the expression cassette of which is as described in FIG. 5).

Envelope plasmid (pENV): This plasmid bears the gene coding an envelope protein, which may be for example the sequence of the VSVG gene coding the envelope protein of the vesicular stomatitis virus (the expression cassette of which is as described in FIG. 3).

2. Production of the Batches

After transfection of the plasmids on cells, the supernatants are harvested and used crude or concentrated/purified according to the method described in application WO 2013/014537.

2.1 Production of the Lentiviral Vectors and Lentiviral Particles

Production is carried out in a 10-stack CellSTACK (6360 cm$^2$, Corning) with HEK293T cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in humid atmosphere at 5% $CO_2$. For the experiment studying the effect of the serum, DMEM is supplemented with 10% of FCS. In particular, induction with sodium butyrate is not carried out. For each batch (MS2RLP and ILV), the transfection mixture is composed of the following three plasmids:

One of the expression plasmids described above, depending on whether a particle (MS2RLP) or a vector ILV is formed, p8.74ΔZF Coat (MS2RLP), p8.74 (ILV) and pENV bearing the envelope VSV-G.

The respective proportions of the plasmids are as follows: 40% of the expression plasmid, 30% of the p8.74 (or p8.74ΔZF) plasmid, 30% of the pENV plasmid.

24 hours after standard transfection with calcium phosphate, the culture supernatant is replaced with fresh unsupplemented DMEM medium. The cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

2.2 Concentration and Purification of the Lentiviral Vectors and Lentiviral Particles The vectors and particles are concentrated and purified according to one of the following two methods:

Method P1 is intended to carry out frontal ultrafiltration of the supernatant on central centrifugation units.

Method P2 is intended to carry out tangential ultrafiltration and then diafiltration of the supernatant. The crude supernatant is concentrated and purified by tangential ultrafiltration using polysulphone hollow-fibre cartridges. The supernatant is treated by diafiltration for 20 diavolumes in continuous mode against DMEM or TSSM buffer. After diafiltration, the retentate is recovered and then concentrated again by frontal ultrafiltration on central centrifugation units.

Production/concentration/purification of the batches for this example is carried out according to method P2.

3. Titration 3.1 Titration of the Functional Particles by qPCR

HCT116 cells (ATCC, CCL-247) are seeded in a 96-well plate in 100 μL of DMEM supplemented with 10% FCS, 100 pg/mL streptomycin, 100 U/mL penicillin and 2 mM L-Gln and then incubated for 24 h at 37° C./5% $CO_2$. Six serial dilutions are carried out for each vector as well as for an internal standard. The cells are transduced by these serial dilutions in the presence of Polybrene® 8 μg/mL (Sigma) and then incubated for three days at 37° C./5% $CO_2$. For each series of samples, one well of non-transduced cells is added as a control. The cells are then trypsinized and the titre (transduction unit/mL) is determined by qPCR after extracting the genomic DNA using the Nucleospin tissue gDNA extraction kit (Macherey-Nagel). The titre obtained (TU/mL) by qPCR is normalized by the internal standard, the titre of which was determined beforehand by FACS.

3.2 Quantification of the Physical Particles by ELISA P24 Assay

The p24 capsid protein is detected directly on the viral supernatant using, and following the recommendations of, the HIV-1 p24 ELISA kit (Perkin Elmer). The p24 protein captured is complexed with a biotinylated polyclonal antibody, and then detected with a streptavidin-HRP peroxidase conjugate. The resultant complex is detected by spectrophotometry after incubation with the ortho-phenylenediamine-HCl (OPD) substrate producing a yellow coloration that is directly proportional to the quantity of p24 protein captured. The absorbance of each well is quantified using the Synergy H1 Hybrid plate reader (Biotek) and calibrated against the absorbance of a standard range of p24 protein. The viral titre expressed in physical particles per ml is calculated from the concentration of p24 protein obtained, knowing that 1 pg of p24 protein corresponds to $10^4$ physical particles.

II. Transduction of Cells of the Immune System

1. Lymphocytes 1.1 Preparation of the Human Lymphocyte Cells

Whole human lymphocytes are prepared from whole human blood by isolating the peripheral mononuclear cells or PBMC (Peripheral Blood Mononuclear Cells) on a Ficoll gradient. The blood sample is taken at room temperature and diluted to ½ with PBS 1× pH 7.4 in a suitable tube (15 or 50 ml).

1 volume of Ficoll solution (GE Healthcare) is carefully deposited under 2 volumes of diluted blood. It is important to obtain 2 separate phases that are not mixed: A lower phase corresponding to the Ficoll and an upper phase corresponding to the diluted blood. The tube is centrifuged for 30 minutes at 400 g at room temperature. The brake of the centrifuge is stopped to avoid disturbing the different phases obtained after centrifugation.

The upper phase corresponds to the plasma, the lower phase corresponds to the Ficoll, and a ring forms between these two phases, which contains the population of interest (PBMCs).

The ring of PBMCs is carefully pipetted and transferred to a new tube. The PBMCs are then washed twice with at least 3 volumes of solution of PBS 1× pH 7.4. The cells are centrifuged for 10 minutes at 100 g at room temperature.

Once the supernatant has been removed, the PBMCs are resuspended in RPMI culture medium, 10% fetal calf serum, 2 mM L-glutamine, 1% penicillin/streptomycin and numbered.

The cells are resuspended at a concentration of $1.10^6$ cells per ml and are deposited on a plastic culture support for 2 h at 37° C./5% $CO_2$. This step allows the monocytes to adhere to the plastic, whereas the lymphocytes remain in suspension and may therefore be recovered in the culture supernatant before being seeded at $1.56×10^5$ cells per cm$^2$ ready for transduction.

1.2 Preparation of the Murine Lymphocyte Cells

The murine lymphocytes are prepared from spleen. The spleen is recovered from a mouse after euthanasia of the animal by cervical dislocation. The spleen is deposited in a well of a 6-well culture plate and swollen by injection of 1 ml of solution of collagenase D (Roche diagnostics) at 2 mg/ml with a syringe fitted with a 26 G ½ needle. The spleen is cut into small pieces in the well using a sterile scalpel in 1 ml of solution of collagenase D at 2 mg/ml. The 2 ml of solution containing the small pieces of spleen is transferred to a 15-ml tube and incubated for 30 minutes in a water bath at +37° C. Enzymatic digestion is stopped by adding 13 ml of cold MACS buffer (PBS 1× pH 7.4, 0.5% FCS, 2 mM EDTA) for a final volume of 15 ml. The cellular suspension is filtered on a 70-µm cellular sieve placed on a 50-ml tube. The volume is made up to 30 ml with cold MACS buffer. The cellular suspension is centrifuged for 10 minutes at 300 g, at +4° C.

Positive sorting for expression of the CD8 marker is then carried out. For this, the supernatant is removed by aspiration and the cellular pellet is taken up in 90 µl of cold MACS buffer and 10 µl of anti-CD8 beads (Miltenyi Biotec) for $10^7$ cells. The mixture is incubated for 15 minutes at +4° C. At the end of incubation, a volume of MACS buffer q.s. 15 ml is added to the suspension. The suspension is centrifuged for 10 minutes at 300 g, at +4° C. The supernatant is removed and the cellular pellet is taken up in the equivalent of 500 µl of cold MACS buffer for $10^8$ cells. The suspension is deposited on a column of the MS type (Miltenyi Biotec) fitted to a magnet and equilibrated beforehand with cold MACS buffer. The column is washed with 3×500 µl of cold MACS buffer. The negative fraction (about 2 ml) is made up to 5 ml with cold MACS buffer and then a cell count is carried out. The cellular suspension is centrifuged for 10 minutes at 300 g, at +4° C. and the cells are resuspended in a type TCT 6-well plate (Corning) at a rate of $1.10^6$ cells per ml in RPMI 1640 medium supplemented with 10% of fetal calf serum, 1% penicillin/streptomycin, 2 mM L-glutamine to be transduced.

After sorting, the different fractions obtained are analysed by flow cytometry (Miltenyl Biotec) with anti-CD8 antibody labelling for monitoring the purity of the populations sorted.

1.3 Transduction of the Lymphocytes (Human and Murine)

On the day of transduction, the lymphocytes are resuspended at a rate of $0.5×10^6$ cells per ml in a flat-bottomed 96-well plate, treated for cell culture, in a volume of 50 µl per well. A transduction medium containing 4 µg/ml final of Polybrene® and the various vectors with the chosen MOIs (namely 10, 20 or 30 pg p24 per cell in the case of RLP and MOI 10, 20, 25 or 50 in the case of ILV for the human T lymphocytes; 0.1, 0.5, 1, or 5 pg p24/cell in the case of RLP and MOI 5, 10, 25, 50 or 75 In the case of ILV for the murine CD8+T lymphocytes) is prepared and added to the cells in a volume of 50 µl, for a final volume of 100 µl per well. The plate is then centrifuged for 75 minutes at 1000 g, at 30° C. The transduction medium is left on the cells for 4 h after the centrifugation step, at 37° C., 5% $CO_2$. After this incubation, 80% of the transduction medium (80 µl) is withdrawn and 180 µl of RPMI medium, 10% fetal calf serum, 2 mM L-glutamine, 1% penicillin/streptomycin is added to each well. The cells are incubated at 37° C., 5% $CO_2$ until analysis.

2. Dendritic Cells 2.1 Preparation of the Human Dendritic Cells 2.1.1 Isolation of the Human Peripheral Mononuclear Cells (PBMCs) from Whole Human Blood The human dendritic cells are prepared from whole human blood by isolating the PBMCs on a Ficoll gradient. The blood sample is taken at room temperature and diluted to ½ with PBS 1× pH 7.4 in a suitable tube (15 or 50 ml).

1 volume of Ficoll solution (GE Healthcare) is carefully deposited under 2 volumes of diluted blood. It is important to obtain 2 separate phases that are not mixed: A lower phase corresponding to the Ficoll and an upper phase corresponding to the diluted blood. The tube is centrifuged for 30 minutes at 400 g at room temperature. The brake of the centrifuge is stopped to avoid disturbing the different phases obtained after centrifugation.

The upper phase corresponds to the plasma, the lower phase corresponds to the Ficoll, and a ring forms between these two phases, which contains the population of Interest (PBMCs).

The ring of PBMCs is carefully pipetted and transferred to a new tube. The PBMCs are then washed twice with at least 3 volumes of solution of PBS 1× pH 7.4. The cells are centrifuged for 10 minutes at 100 g at room temperature.

Once the supernatant has been removed, the PBMCs are resuspended in SFM culture medium, 2 mM L-glutamine, 1% penicillin/streptomycin and numbered.

The cells are resuspended at a concentration of $1.10^6$ cells per ml ($2.5×10^6$ cells per $cm^2$) and are deposited in a type TCT 48-well plate (Corning) for 2 h at 37° C./5% $CO_2$. This step allows the monocytes to adhere to the plastic, whereas the lymphocytes remain in suspension. After incubation for 2 h the plate is washed with PBS1× so that only the monocytes are kept in culture, which will be transduced.

2.1.2 Differentiation of the Population of Monocytes into Dendritic Cells

The dendritic cells are cultured in a type TCT 48-well plate (Corning) at a rate of $1.10^8$ cells per ml in SFM medium supplemented with 1% penicillin/streptomycin, 2 mM L-glutamine, 200 nM human IL4 and 50 mM human GM-CSF. These culture conditions make it possible to obtain dendritic cells of immature phenotype (iDC). The dendritic cells are left in culture for 5 days at 37° C./5% $CO_2$ with renewal of the culture medium on the third day.

To obtain mature dendritic cells (mDC), on the third day of culture the cells are put in a maturation medium containing 0.1 pg/ml of LPS.

2.2 Preparation of the Murine Dendritic Cells

The murine dendritic cells (DC) are prepared from bone marrow obtained from the hind limbs (BMDC culture). The long bones, the femurs and the tibias, are recovered from adult mice and transferred to a 50-ml tube containing RPMI 1640 medium supplemented with 1% penicillin/streptomycin. The marrow is removed from the bones using a syringe fitted with a 26 G ½ needle and containing RPMI 1640 medium supplemented with 1% penicillin/streptomycin. The cellular suspension is centrifuged for 5 minutes at 300 g, +4° C. The supernatant is removed and the pellet is taken up in 1 ml of RPMI 1640 medium supplemented with 1% penicillin/streptomycin+3 ml of Gey solution (155 mM $NH_4Cl$, 1 mM $KHCO_3$). The suspension is incubated for 5 minutes at room temperature in order to lyse red blood cells contained in the cellular suspension. After incubation, the volume is adjusted to 15 ml with RPMI 1640 medium supplemented with 10% of fetal calf serum, 1% penicillin/streptomycin, 2 mM L-glutamine to stop the reaction and the cellular suspension is centrifuged for 5 minutes at 300 g, +4° C. The supernatant is removed and the pellet is taken up in a volume of RPMI 1640 medium supplemented with 10% of fetal calf serum, 1% penicillin/streptomycin, 2 mM L-glutamine. This cellular suspension is filtered on a 70-µm cellular sieve placed on a 50-ml tube. The sieve is rinsed until a final volume of about 30 ml is obtained. The cells are counted and the cellular suspension is centrifuged for 5 minutes at 300 g. The supernatant is removed and the pellet is taken up in a volume of RPMI 1640 medium supplemented with 10% of fetal calf serum, 1% penicillin/streptomycin, 2 mM L-glutamine, 50 µM 2-MercaptoEthanol, 25 ng/ml murine IL4 and 25 ng/ml murine GM-CSF, giving a cell concentration of $1.10^6$ cells per ml. The dendritic cells are cultured in a type ULA 6-well plate (Corning) at a rate of $1.10^6$ cells per ml. The dendritic cells are left in culture for 5 days at 37° C./5% $CO_2$ with renewal of the culture medium every 2-3 days. On the third day, the BMDCs are put back in culture in a new 6-well ULA plate in order to separate them from the cells of the macrophage type, which still adhere to the plate used for culture.

2.3 Transduction of Human Dendritic Cells

On the day corresponding to isolation of the PBMCs, the cells are transduced by the ILV.EF1 ZsGreen1 vector at the chosen MOIs (1, 2 or 4 pg p24 per cell in the case of RLP and MOI 25, 50 or 75 in the case of ILV) in SFM culture medium, 2 mM L-glutamine, 1% penicillin/streptomycin with the following transfection agents: Polybrene® at 4 µg/mL (Sigma) and BX795 6 µM (Invivogen) and incubated at +37° C./5% $CO_2$. 4 h after transduction, the transduction medium is replaced with the differentiation medium specific to the dendritic cells (SFM, 2 mM L-glutamine, 1% penicillin/streptomycin, 200 nM human IL4 and 50 mM human GM-CSF). This medium allows culture of the immature dendritic cells (iDC). The cells are transduced 4 h post-seeding by the various vectors (RLP or ILV) for elaborating transduction on the EF1.ZsGreen1 cassette.

The cells transduced are analysed at different times (1, 2, 3 and 4 days post-transduction).

To obtain mature dendritic cells (mDC), the cells are put in a maturation medium containing 0.1 µg/ml of LPS on the third day of culture and they are analysed on day 4.

2.3.1 Transduction of Human Dendritic Cells by RLP.ZsGreen1

The dendritic cells transduced by the RLP.ZsGreen1 vector were the subject of development connected with characterization of the expression of fluorescence analysed by flow cytometry according to an increasing range of RLP particles from 1 µg p24 to 4 pg p24 per cell and at different analysis times (1, 2, 3 and 4 days post-transduction for the iDCs and 4 days post-transduction for the mDCs). A negative control of transduction is prepared with only the medium containing the transduction agents Polybrene® at 4 µg/mL (Sigma) and BX795 6 µM (Invivogen).

The dendritic cells are phenotyped by immunolabeling with anti-CD11c, anti-CD209 DC SIGN, anti-CD86 specific antibodies (Miltenyi Biotec) and characterized by flow cytometry.

2.3.2 Transduction of Human Dendritic Cells by ILV.EF1.ZsGreen1

The dendritic cells transduced by the ILV.EF1.ZsGreen1 vector were the subject of development connected with characterization of expression of fluorescence analysed by flow cytometry over an increasing range of ILV lentiviral particles from a multiplicity of infection MOI from 25 to 75 and at different analysis times (1, 2, 3 and 4 days post-transduction for the IDCs and 4 days post-transduction for the mDCs). A negative control of transduction is prepared with the medium containing only the transduction agents Polybrene® at 4 µg/mL (Sigma) and BX795 6 µM (Invivogen).

The dendritic cells are phenotyped by immunolabeling with anti-CD11c, anti-CD209 DC SIGN, anti-CD86 specific antibodies (Miltenyi Biotec) and characterized by flow cytometry.

2.4 Transduction of Murine Dendritic Cells (BMDCs)

6 days after the start of culture, the dendritic cells are recovered and centrifuged for 5 min at 300 g. The supernatant is removed and the cells are washed in 1 ml of RPMI 1640 supplemented with 10% of fetal calf serum, 1% penicillin/streptomycin, 2 mM L-glutamine, and centrifuged for 5 min at 300 g. The dendritic cells are seeded at $0.5 \times 10^6$ cells/ml in a 96-well or 24-well plate in RPMI 1640 supplemented with 10% of fetal calf serum, 1% penicillin/streptomycin, 2 mM L-glutamine, 50 µM 2-MercaptoEthanol, 25 ng/ml murine IL4 and 25 ng/ml murine GM-CSF. The cells are transduced 24 h post-seeding by the various vectors (RLP or ILV) for elaborating transduction owing to expression of ZsGreen1 fluorescence. The transductions are carried out in the presence of Polybrene® 4 µg/mL (Sigma), followed by spinoculation of the plate at 1000 g for 75 minutes at +30° C. The transduction medium is then left for 4 h at +37° C./5% $CO_2$.

After incubation, 80% of the transduction medium is removed by pipetting and replaced with an equivalent volume of RPMI 1640 supplemented with 10% of fetal calf serum, 1% penicillin/streptomycin, 2 mM L-glutamine, 50 µM 2-MercaptoEthanol, 25 nM Murine IL4 and 25 ng/ml preheated murine GM-CSF. The cells are then put back at 37° C./5% $CO_2$.

2.4.1 Transduction of Murine Dendritic Cells by RLP.ZsGreen1

The dendritic cells transduced by the RLP.ZsGreen1 vector were the subject of development connected with characterization of expression of fluorescence analysed by flow cytometry over an increasing range of RLP particles from 0.1 pg p24 to 5 pg p24 per cell and at different analysis times (1, 2, 3 and 4 days post-transduction). A negative control of transduction is prepared with only the medium containing the transduction agent Polybrene® at 4 µg/mL (Sigma).

The dendritic cells are phenotyped by immunolabeling with anti-CD11c, anti-CD86, anti-CD80 specific antibodies (Miltenyi Biotec) and characterized by flow cytometry.

2.4.2 Transduction of Murine Dendritic Cells by ILV.EF1.ZsGreen1

The dendritic cells transduced by the ILV.EF1.ZsGreen1 vector were the subject of development connected with characterization of expression of fluorescence analysed by flow cytometry over an increasing range of lentiviral particles ILV from a multiplicity of infection MOI from 5 to 75 and at different analysis times (1, 2, 3 and 4 days post-transduction). A negative control of transduction is prepared with only the medium containing the transduction agent Polybrene® at 4 µg/mL (Sigma).

The dendritic cells are phenotyped by immunolabeling with anti-CD11c, anti-CD86, anti-CD80 specific antibodies (Miltenyi Biotec) and characterized by flow cytometry.

3. Phenotyping and Characterization of the Cells 3.1 Immunolabeling of the Lymphocytes After sorting or at the different analysis times after transduction, the lymphocytes are recovered from the culture plates in which they are in suspension and the cells are transferred to the wells of a conical-bottom 96-well culture plate. The cells are washed with a solution of PBS 1× pH 7.4, 5% FCS and centrifuged at 300 g for 5 minutes. The supernatant is removed by inversion.

The lymphocytes are phenotyped by immunolabeling with the following specific antibodies conjugated with fluorochromes: anti-CD8, anti-CD4, anti-CD3 or anti-TCR (Miltenyi Biotec). For this, mixtures of solution of antibodies are prepared and 50 µl per well is deposited on the cells. The cells are incubated for 20 minutes at room temperature in the dark. 50 µl of PBS 1× pH 7.4, 5% FCS is added and the cells are centrifuged at 300 g for 5 minutes. The supernatant is removed by inversion. The cells are taken up in 100 µl of PBS 1× pH 7.4, 5% FCS. The cells are centrifuged at 300 g for 5 minutes. The supernatant is removed by inversion. The cells are taken up in 100 µl of PBS 1× pH 7.4, 5% FCS and analysed by flow cytometry.

3.2 Immunolabeling of Human Dendritic Cells

At each analysis time, the wells are scraped with a pipette cone or a scraper, depending on the format of the culture plate, and the cells are transferred to the wells of a conical-bottom 96-well culture plate. The cells are washed with a solution of PBS 1× pH 7.4, 5% FCS and centrifuged at 300 g for 5 minutes. The supernatant is removed by inversion.

The dendritic cells are phenotyped by immunolabeling with the following specific antibodies conjugated with fluorochromes: anti-CD11c, anti-CD209 DC SIGN, anti-CD86 (Miltenyi Biotec). For this, mixtures of solution of antibodies are prepared and 50 µl per well is deposited on the dendritic cells recovered. The cells are incubated for 20 minutes at room temperature in the dark. 50 µl of PBS 1× pH 7.4, 5% FCS is added and the cells are centrifuged at 300 g for 5 minutes. The supernatant is removed by inversion. The cells are taken up in 100 µl of PBS 1× pH 7.4, 5% FCS. The cells are centrifuged at 300 g for 5 minutes. The supernatant is removed by inversion. The cells are taken up in 100 µl of PBS 1× pH 7.4, 5% FCS and analysed by flow cytometry.

3.3 Immunolabeling of Murine Dendritic Cells

At each analysis time, the cells are transferred to the wells of a conical-bottom 96-well culture plate. The cells are washed with a solution of PBS 1× pH 7.4 and centrifuged at 300 g for 5 minutes. The supernatant is removed by inversion.

The viability of the dendritic cells is analysed by specific immunolabeling with the "Viobility™ 485/520" viability marker (Miltenyl Biotec). For this, 1 µl of Viobility™, in solution in DMSO, is applied for each well of cells, in 100 µl of PBS 1× pH7.4. The cells are incubated for 20 minutes at room temperature in the dark. The cells are centrifuged at 300 g for 5 minutes. The supernatant is removed by inversion. The cells are taken up in 100 µl of PBS 1× pH 7.4, 5% FCS and centrifuged again at 300 g for 5 minutes. The supernatant is removed by inversion. The cells are taken up in 100 µl of PBS 1× pH 7.4, 5% FCS to be labelled with specific antibodies as described below for phenotyping.

The dendritic cells are phenotyped by immunolabeling with the following specific antibodies conjugated with fluorochromes: anti-CD11c, anti-CD86, anti-CD80 (Miltenyl Biotec). For this, mixtures of solution of antibodies are prepared and 50 µl per well is deposited on the dendritic cells recovered. The cells are incubated for 20 minutes at room temperature in the dark. 50 µl of PBS 1× pH 7.4, 5% FCS is added and the cells are centrifuged at 300 g for 5 minutes. The supernatant is removed by inversion. The cells are taken up in 100 µl of PBS 1× pH 7.4, 5% FCS. The cells are centrifuged at 300 g for 5 minutes. The supernatant is removed by inversion. The cells are taken up in 100 µl of PBS 1× pH 7.4, 5% FCS and analysed by flow cytometry.

3.4 Flow Cytometry

The immunolabelled dendritic cells are analysed by flow cytometry (Miltenyi Biotec) and analysed. The samples were calibrated according to their size (SSC) and their granularity (FSC). The cells labelled with Viobility™ are dead or dying, therefore the viable cells are the negative cells (labelling by exclusion). The cells are characterized on the MacsQuantVYB (Miltenyi Biotec) and analysed with the MacsQuant software (Miltenyi Biotec).

Figure 6A:
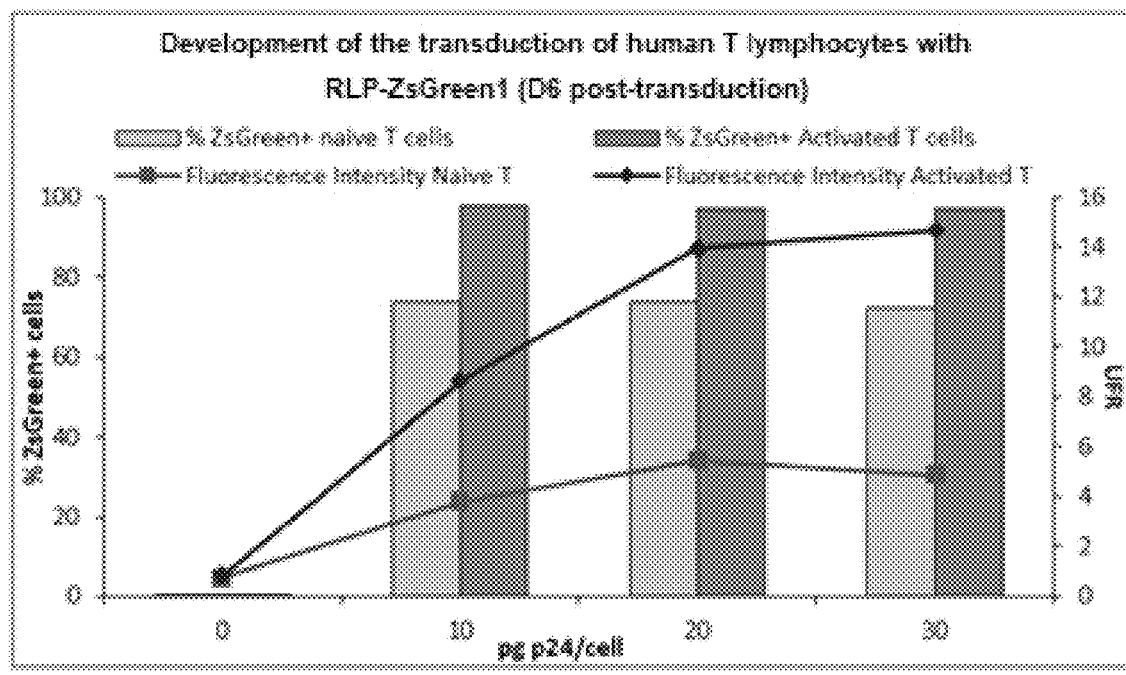
FIG. 6A is a diagram illustrating the effectiveness of the transduction of human lymphocytes with a particle according to the invention.
Figure 6B:
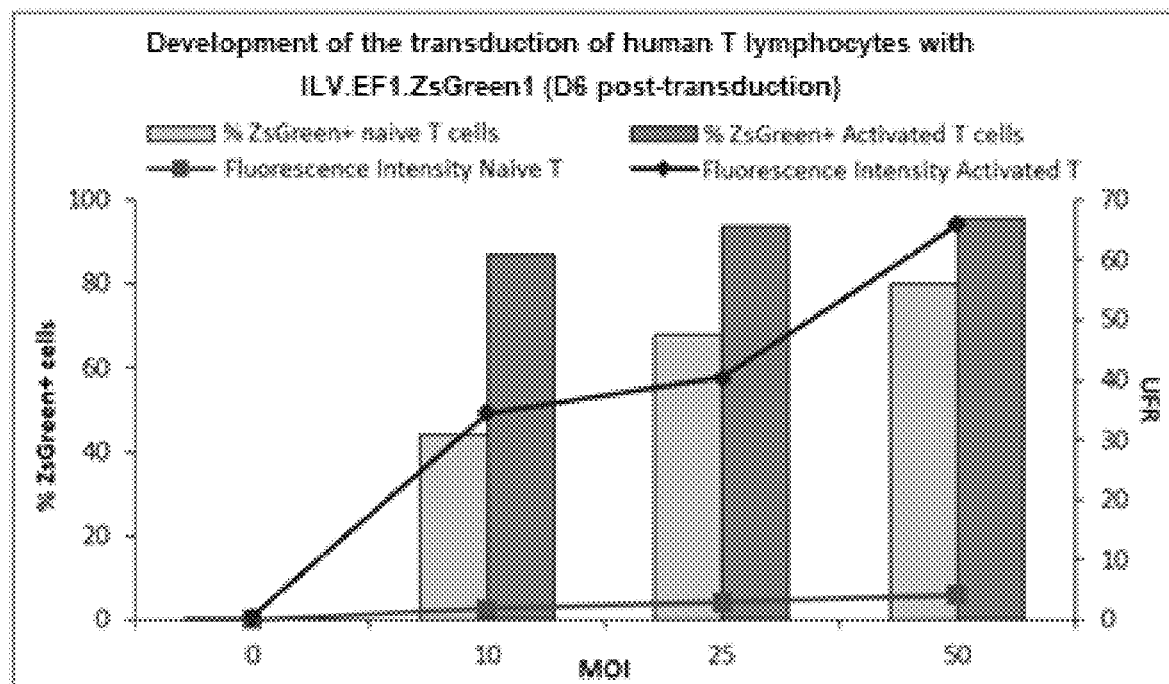
FIG. 6B is a diagram illustrating the effectiveness of the transduction of human lymphocytes with an integrating lentiviral vector (ILV)
Figure 7A:
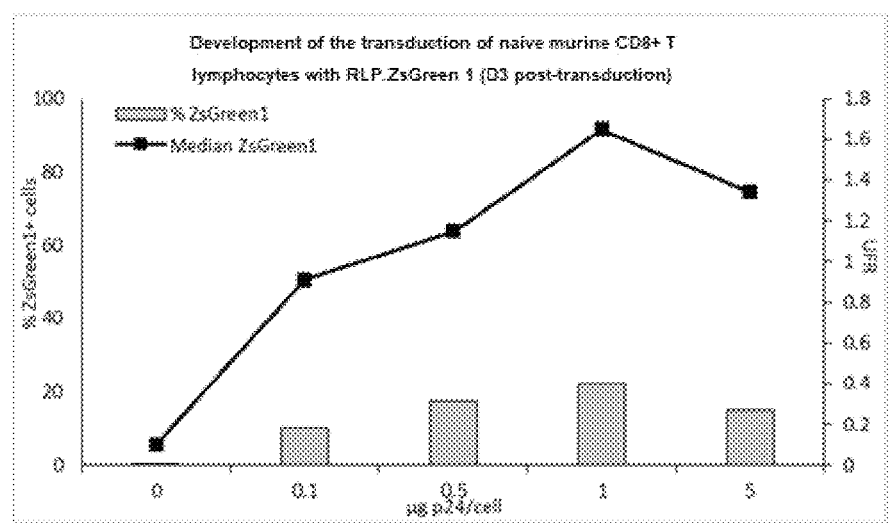
FIG. 7A is a diagram illustrating the effectiveness of the transduction of murine lymphocytes with a particle according to the invention.
Figure 7B:
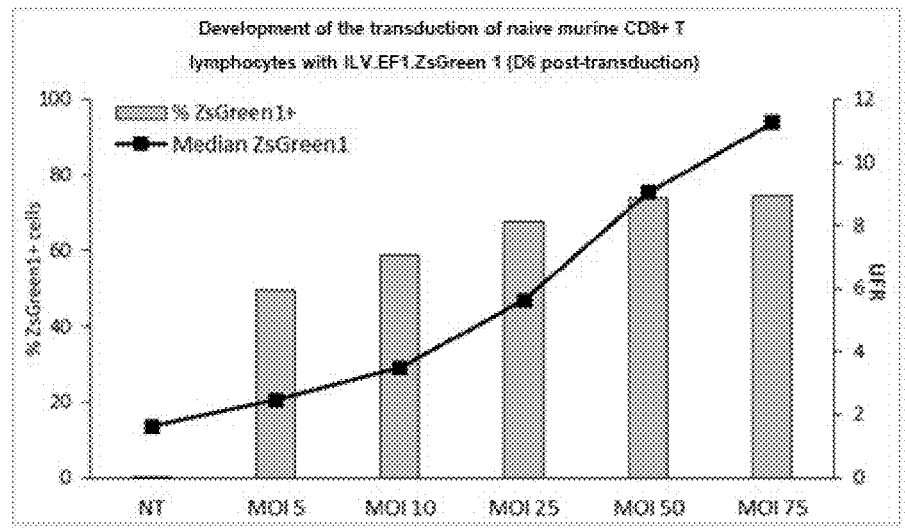
FIG. 7B is a diagram illustrating the effectiveness of the transduction of murine lymphocytes with an integrating lentiviral vector (ILV)

III. Results:

1. Comparison of the Transduction Effectiveness of Immune Cells by RLP and ILV 1.1 T Lymphocytes The transduction of T lymphocytes by the RLP particles or the ILV vectors shows greater effectiveness in humans (FIG. 6A and FIG. 6B) than in the mouse (FIG. 7A and FIG. 7B). In fact, naive human T lymphocytes are transduced with an effectiveness of 70% with RLP, which is comparable to what is obtained with ILV vectors. Likewise, more than 90% of positive cells are obtained after activation with RLP, as with ILV. However, murine T lymphocytes are still more difficult to transduce, with a result ranging from 20% for RLP to 70% with ILV under the conditions of multiplicity of infection tested. By increasing the multiplicity of infection (MOI), it would be possible to obtain higher effectiveness on murine T lymphocytes but with a risk of inducing cellular toxicity.

1.2 Dendritic Cells

The first transduction assays of dendritic cells (DC) were carried out on human cells prepared from peripheral blood from healthy human donors.

Figure 8A:
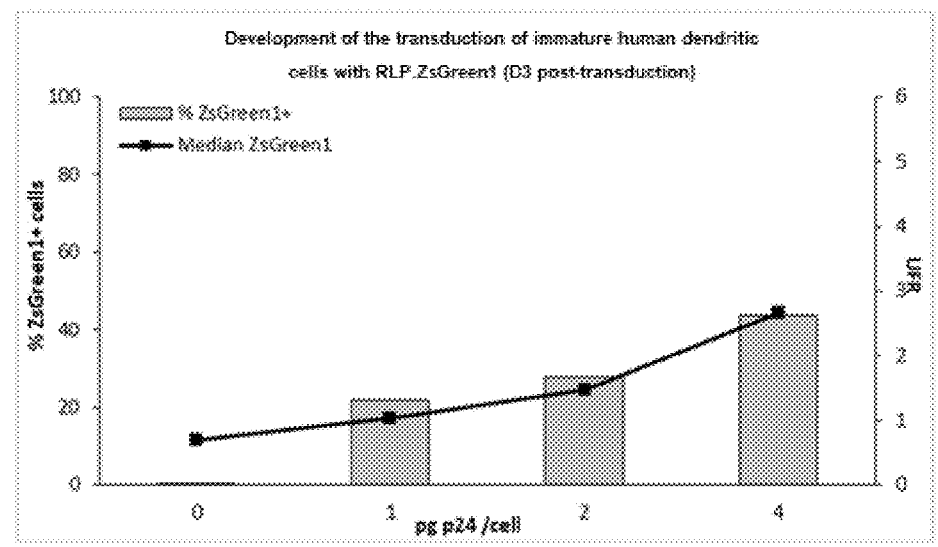
FIG. 8A is a diagram illustrating the effectiveness of the transduction of immature human dendritic cells with a particle according to the invention.
Figure 8B:
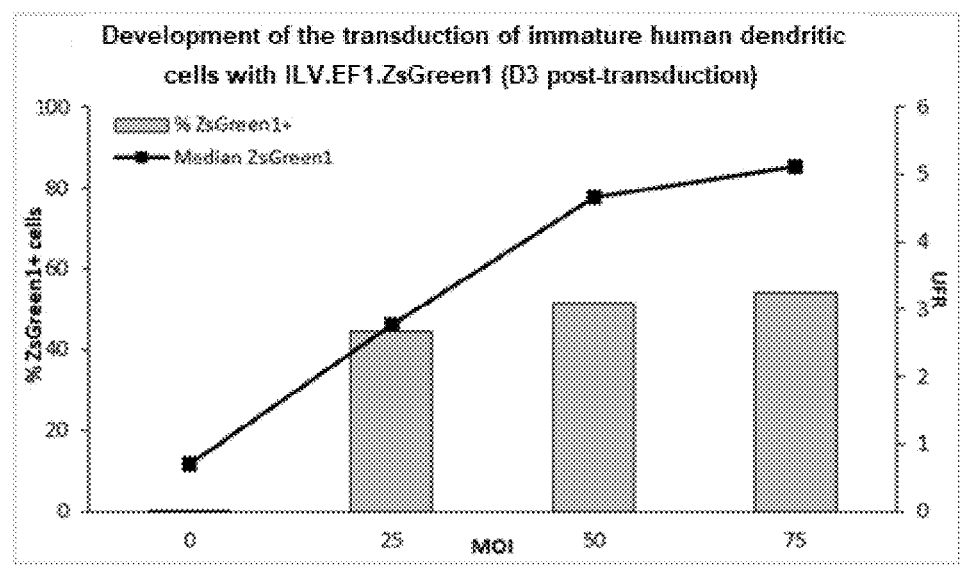
FIG. 8B is a diagram illustrating the effectiveness of the transduction of immature human dendritic cells with an integrating lentiviral vector (ILV)
Figure 8C:
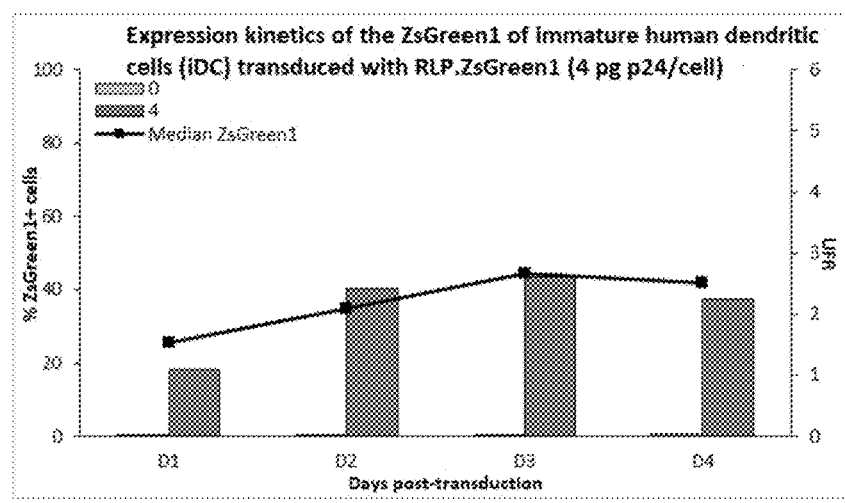
FIG. 8C illustrates the expression kinetics of ZsGreen in immature human dendritic cells transduced with a particle according to the invention.
Figure 8D:
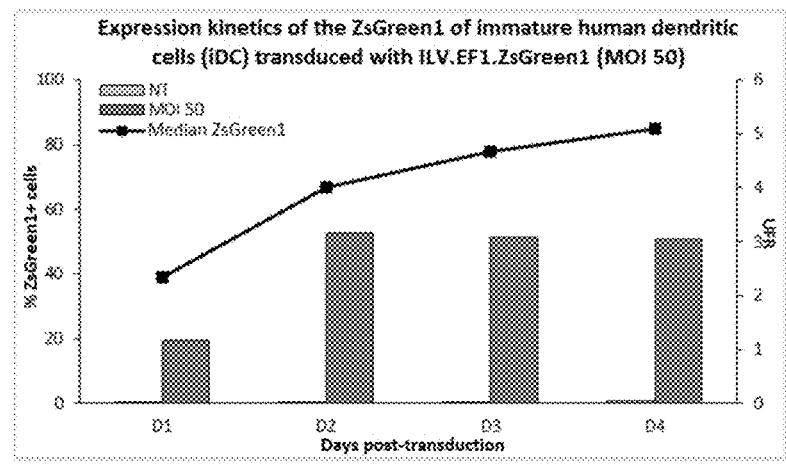
FIG. 8D illustrates the expression kinetics of ZsGreen in immature human dendritic cells transduced with an integrating lentiviral vector (ILV)
Figure 8E:
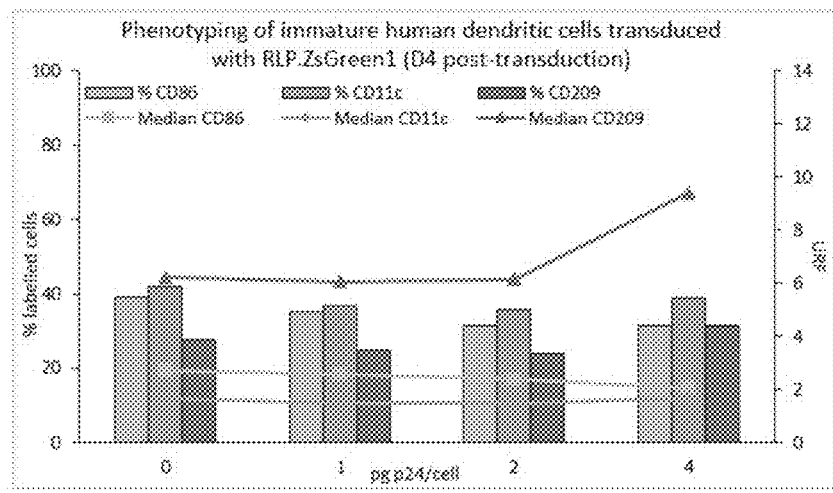
FIG. 8E is a diagram illustrating the phenotyping of immature human dendritic cells transduced with a particle according to the invention.
Figure 8F:
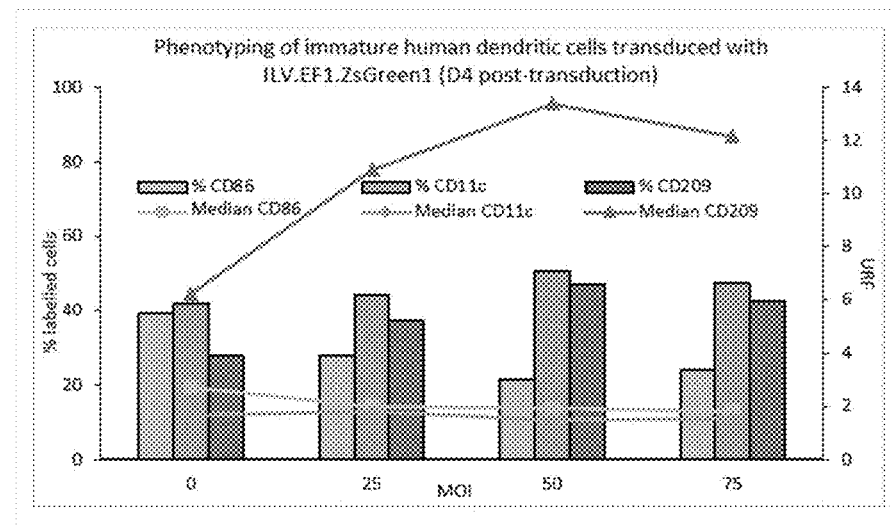
FIG. 8F is a diagram illustrating the phenotyping of immature human dendritic cells transduced with an integrating lentiviral vector (ILV)

Transduction of immature human dendritic cells (DC) by lentiviral particles bearing RNA (RLP) or integrative lentiviral vectors (ILV) shows comparable effectiveness. Expression remains stable for up to 4 days post-transduction (FIG. 8C). Transduction of human DCs by RLP particles at MOI of 4 pg p24/cell (FIG. 8A) leads to 40% of positive cells. This same effectiveness of 40% is obtained with ILV vectors at MOI 75 (FIG. 8B). Owing to integration, expression resulting from transduction by ILV vectors remains stable over time (FIG. 8D). Analysis of 4 biomarkers characteristic of human DCs on the DCs transduced shows that expression of these biomarkers is not significantly modified by transduction by RLP particles (FIG. 8E), demonstrating that transduction does not modify the phenotype of the target cells. The same result is obtained with the integrative lentiviral vectors with only a slight Increase in the CD209 marker (FIG. 8F). These results indicate that transduction by ILV vectors and RLP particles will not disturb the immature phenotype of the immature DCs and does not involve them in an activation or differentiation process or pathway.

Figure 9A:
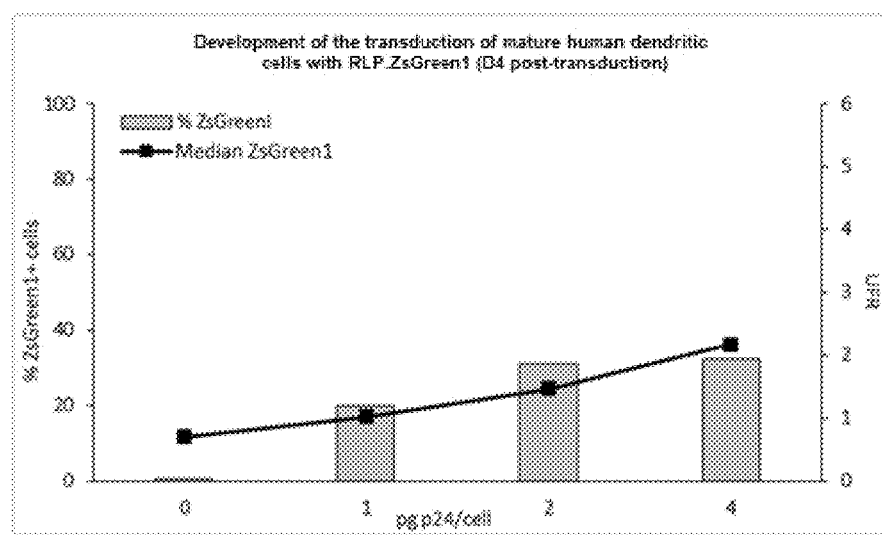
FIG. 9A is a diagram illustrating the effectiveness of the transduction of mature human dendritic cells with a particle according to the invention.
Figure 9B:
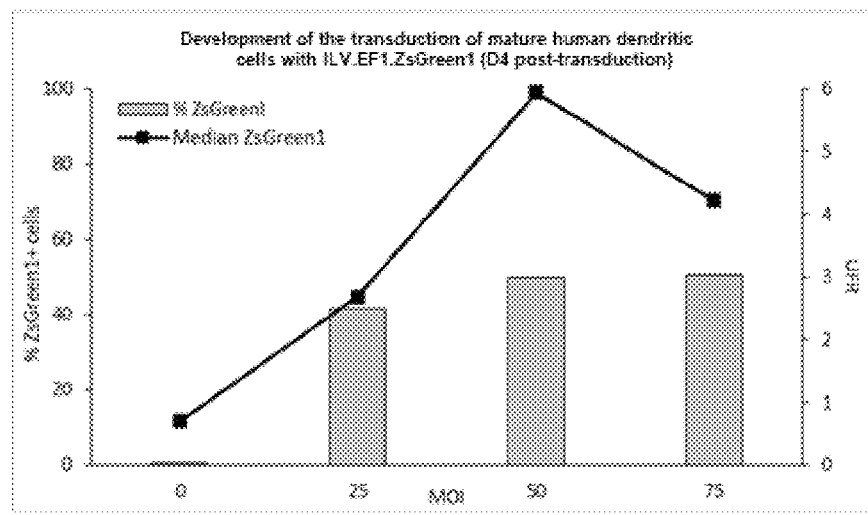
FIG. 9B is a diagram illustrating the effectiveness of the transduction of mature human dendritic cells with an integrating lentiviral vector (ILV)
Figure 9C:
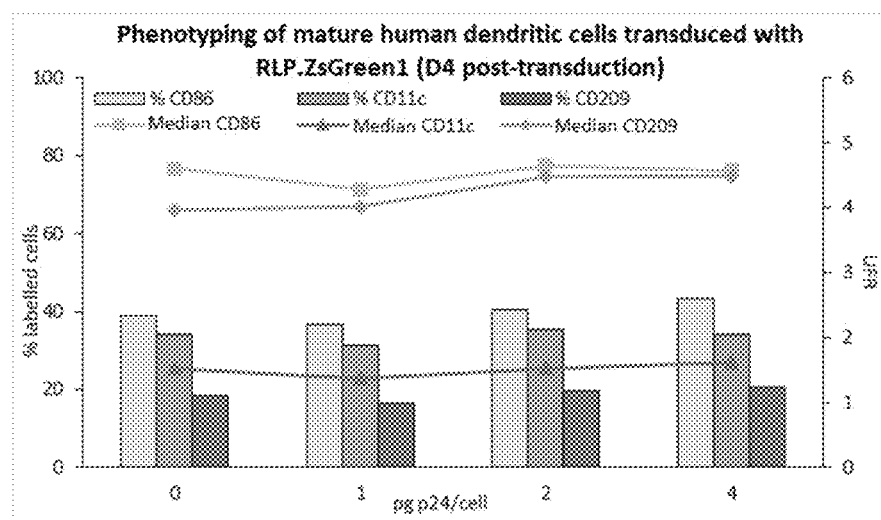
FIG. 9C is a diagram illustrating the phenotyping of mature human dendritic cells transduced with a particle according to the invention.
Figure 9D:
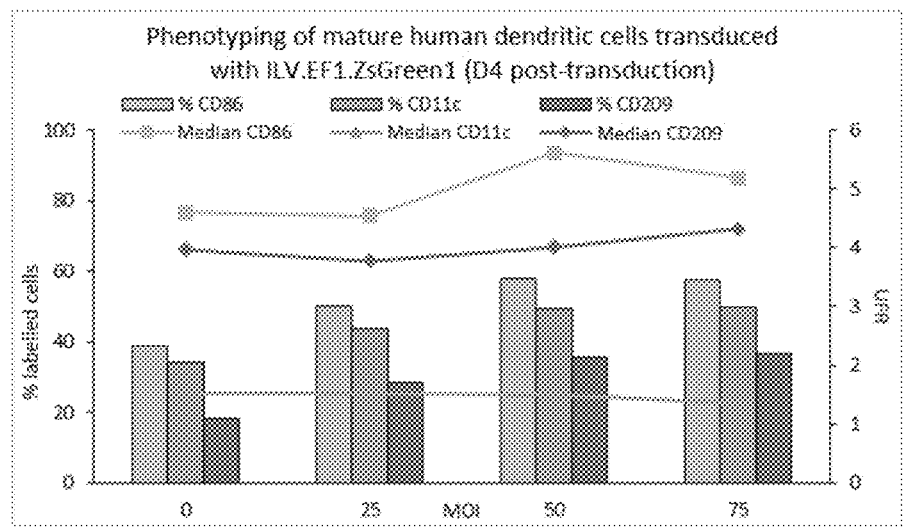
FIG. 9D is a diagram illustrating the phenotyping of mature human dendritic cells transduced with an integrating lentiviral vector (ILV)

In parallel, transduction assays were conducted on dendritic cells matured by adding LPS to the cultures. The results show an effectiveness of transduction of the mature DCs of 30% with the RLP particles at MOI of 4 pg p24/cell (FIG. 9A) and of 50% with the ILV vectors at MOI of 75 (FIG. 9B). As before, transduction by the RLP particles (FIG. 9C) and by the ILV vectors (FIG. 9D) does not significantly disturb expression of the biomarkers characteristic of the dendritic cells.

Figure 10A:
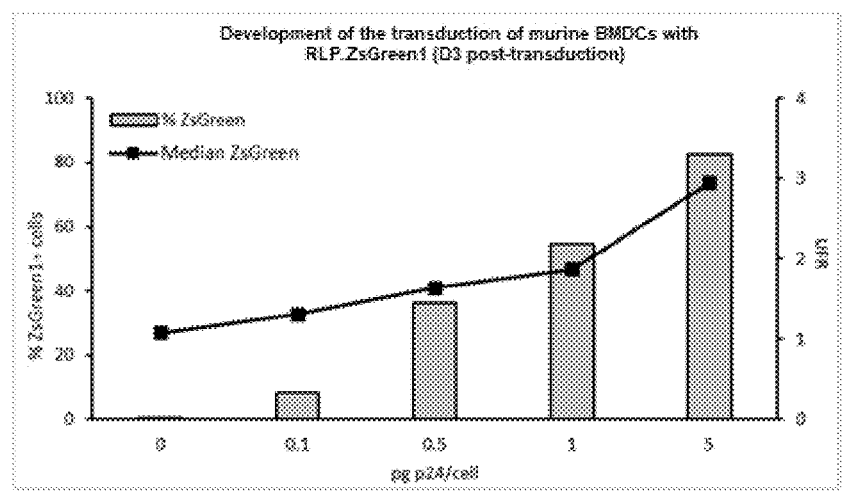
FIG. 10A is a diagram illustrating the effectiveness of the transduction of dendritic cells derived from mouse bone marrow (BMDC) with a particle according to the invention.
Figure 10B:
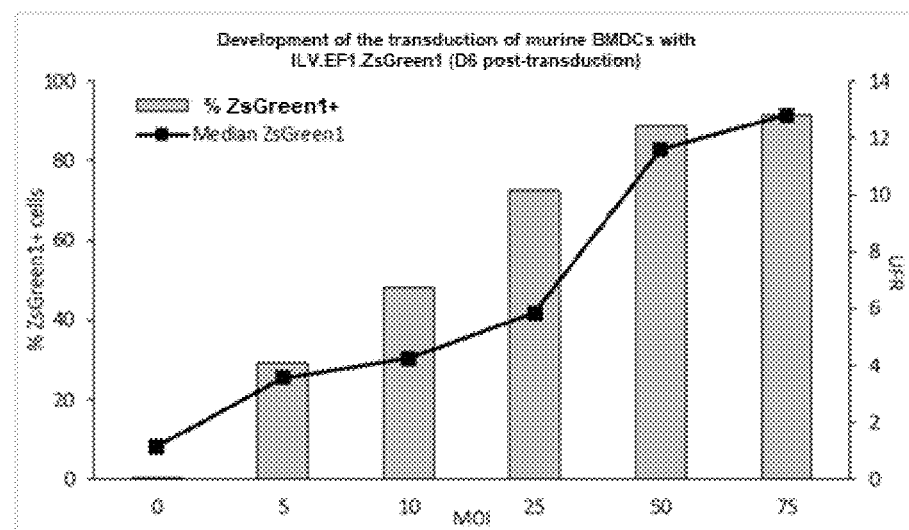
FIG. 10B is a diagram illustrating the effectiveness of the transduction of BMDC cells with an integrating lentiviral vector (ILV)
Figure 10C:
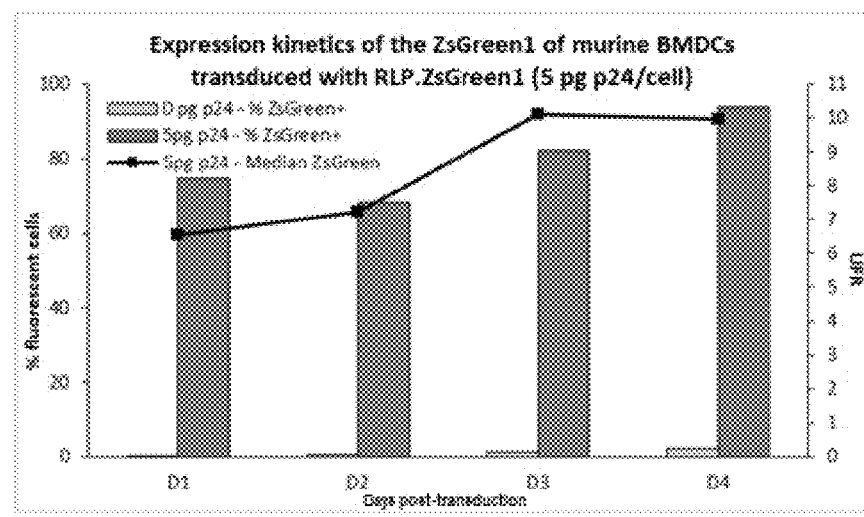
FIG. 10C illustrates the expression kinetics of ZsGreen in BMDC cells transduced with a particle according to the invention.
Figure 10D:
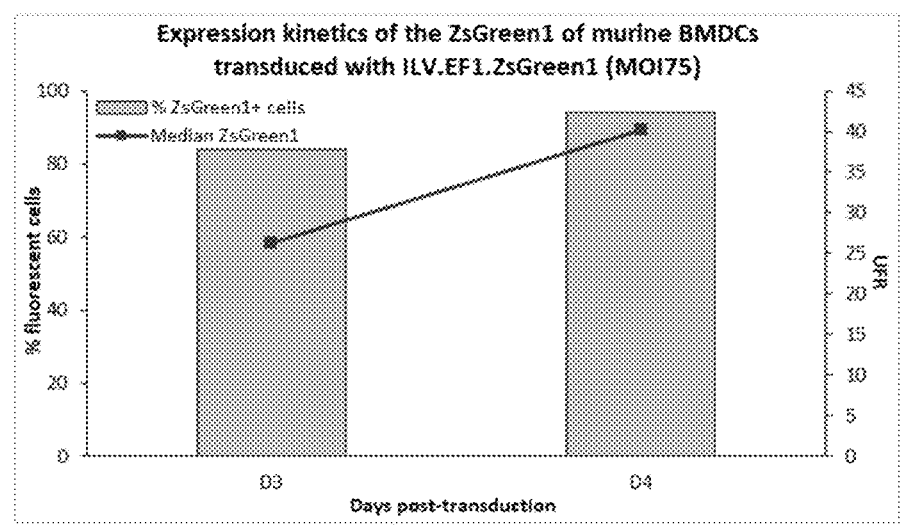
FIG. 10D illustrates the expression kinetics of ZsGreen in BMDC cells transduced with an integrating lentiviral vector (ILV)
Figure 10E:
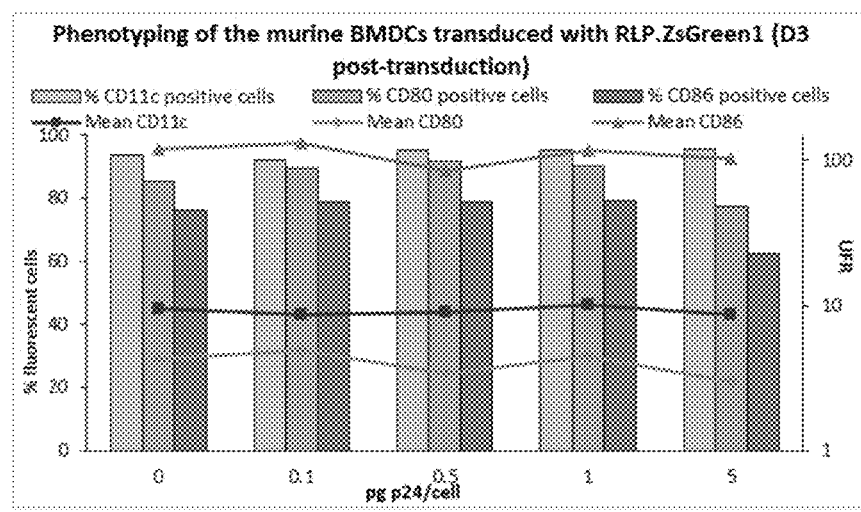
FIG. 10E is a diagram illustrating the phenotyping of BMDC cells transduced with a particle according to the invention.
Figure 10F:
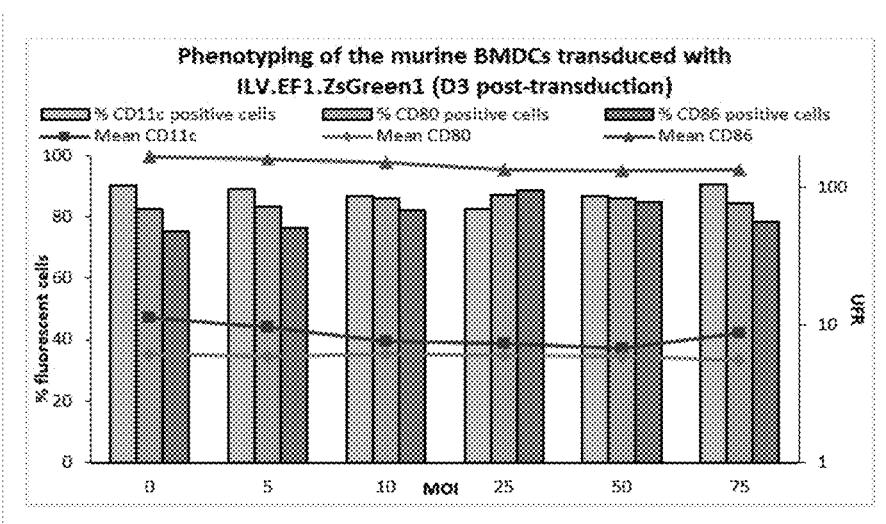
FIG. 10F is a diagram illustrating the phenotyping of BMDC cells transduced with an integrating lentiviral vector (ILV)

The same transduction assays were conducted on dendritic cells derived from mouse bone marrow (BMDCs). The results obtained show transduction of the BMDCs by the RLP particles of 80% at MOI of 5 pg p24/cell (FIG. 10A) and of 90% by the ILV vectors at MOI of 75 (FIG. 10B). In both cases, transduction by the RLP particles or by the ILV vectors shows a dose effect. The transduction kinetics of the BMDCs by the RLP particles shows that the fluorescence remains stable at 4 days post-transduction (FIG. 10C). The kinetics of fluorescence expression in the BMDCs transduced by the ILV vector was only viewed classically for an Integrating vector, starting from the third day (FIG. 10D). In parallel, expression of the specific biomarkers of the murine DCs is not modified after transduction, whether it is with the RLP particles (FIG. 10E) or the ILV vector (FIG. 10F).

2. Analysis of the Toxicity Induced by Increasing Doses of RLP and ILV in Murine Dendritic Cells (BMDCs)

Transduction assays were conducted on dendritic cells derived from mouse bone marrow (BMDCs) as described above, but including specific labelling of the dead cells in order to evaluate whether toxicity was induced by transduction at increasing doses of ILV or of RLP. The BMDCs transduced were analysed at D2 on the basis of the percentage of total viable cells as well as the percentage of cells expressing ZsGreen1 among the cells expressing the specific CD11c marker of the dendritic cells. The results obtained (FIG. 12) show that, 48 h after transduction, specific analysis of expression of ZsGreen1 in the BMDCs expressing CD11c shows transduction by the RLP particles of 50% of the CD11c+ BMDCs starting from MOI of 0.5 pg p24/cell and of 75% by the ILV vectors at MOI of 75. A dose effect is also observed in analysis of the fluorescence intensity expressed by these cells, with equivalent levels for the RLPs used at MOI 1 for the ILVs or 5 pg p24/cell for the RLPs. Finally, regardless of the dose of RLP particles applied to the BMDCs (0.1 to 5 pg p24/cell), no significant toxicity is observed (viability>80%). In both cases, transduction by the RLP particles or by the ILV vectors therefore demonstrates non-toxicity of the lentiviral particles on primary cells and in particular on APCs.

EXAMPLE 2

Effectiveness of Expression of Receptors or of Antigens in the Immune Cells

Figure 12A:
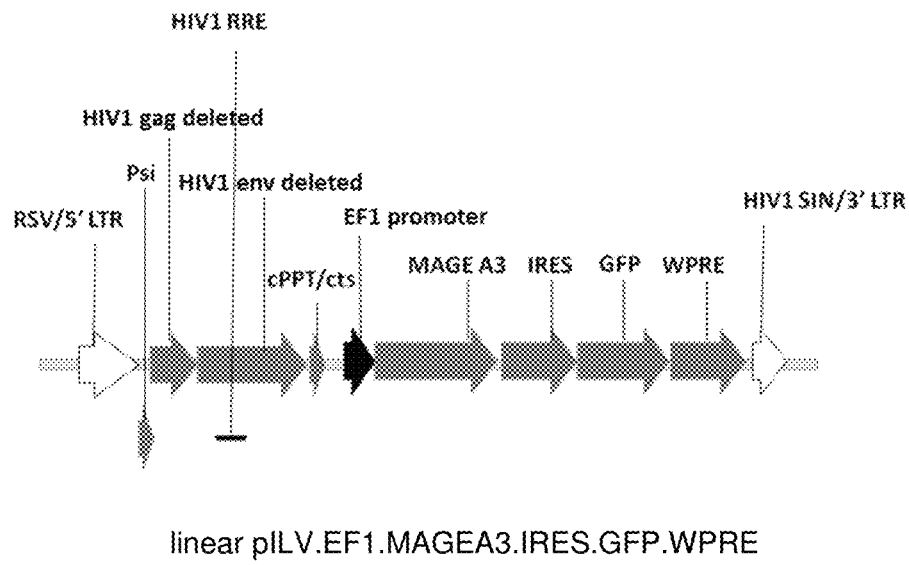
FIG. 12A is a schematic diagram of the construction of the expression cassette derived from the expression plasmid bearing, as RNA sequence of interest, a complete antigen sequence coding the MAGE A3 antigen, this expression plasmid being used for the production of integrative lentiviral vectors (ILV)
Figure 12B:
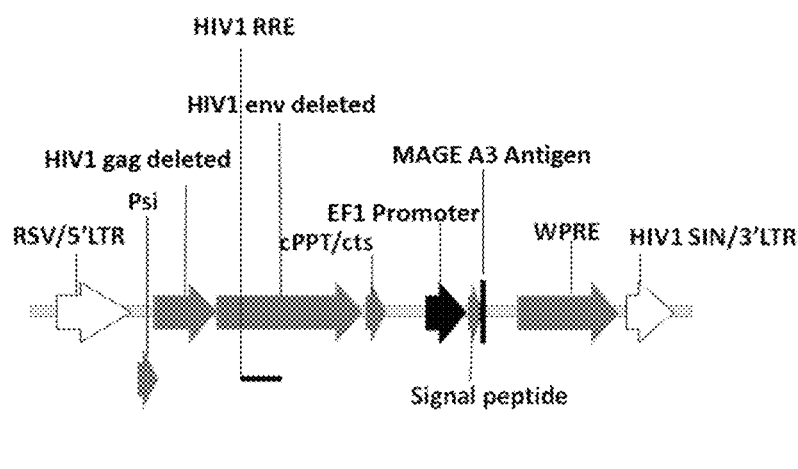
FIG. 12B is a schematic diagram of the construction of an expression plasmid bearing, as RNA sequence of interest, a partial antigen sequence coding the MAGE A3 antigen (PS-MageA3 or PS-MAGEA3), this expression plasmid being used for the production of integrative lentiviral vectors (ILV)

I. Preparation of the Viral Particle According to the Invention and of the Comparative Systems
  1. Plasmid Construction
  1.1 Plasmids for Producing MS2RLP Lentiviral Particles According to the Invention
    Expression plasmid for a sequence of interest: The expression plasmid bears a promoter-sequence of interest-polyA expression cassette with or without an intron sequence or RNA-stabilizing sequence. In order to transport the mRNAs into the lentiviral particles, 12 repetitions of the stem-loop motif of the MS2 RNA (ctagaaaacatgaggatcacccatgtctgcag, SEQ ID No.1) were inserted within an expression cassette downstream of the reporter gene. The promoter used may be the CMV or EF1 promoter but other promoters may be used. The sequence of interest may code an antigen or an epitope. The sequence of interest may be a cDNA coding a protein, for example an immunogenic protein or an immunomodulating protein. Many biomarkers were identified on the tumour cells and their complete sequence and/or partial sequences are used in immunotherapy. For example, the sequence used for expressing the MAGEA3 antigen may be complete (FIG. 11A) or partial (FIG. 11B). Other partial sequences of tumour biomarkers may be used, such as those of gp100 (FIG. 11C) or of tyrosinase (FIG. 11D). Many other examples of complete or partial sequences of tumour biomarkers may be used.
    Encapsidation plasmid: This plasmid is identical to that described in Example 1 (the expression cassette of which is as described in FIG. 2).
    Envelope plasmid (pENV): This plasmid is identical to that described in Example 1 (the expression cassette of which is as described in FIG. 3).
  1.2 Plasmids for Producing Integrative Lentiviral Vectors ILV
    Expression plasmid for a sequence of interest: The expression plasmid bears a promoter-sequence of interest expression cassette (the expression cassette of which is as described in FIG. 12). This plasmid may contain other elements such as the native sequence WPRE (Woodchuck Hepatitis Virus Post-transcriptional Regulatory Element) or the sequence cPPT/CTS. Viral pathogenicity is eliminated by substitution of regions of the viral genome required for retroviral replication by the transgene. As before, the sequence of interest may code a complete antigenic protein, an antigen or an epitope. Many biomarkers were identified on the tumour cells and their complete sequence and/or partial sequences are used in immunotherapy. For example, the sequences used for expressing MAGEA3 may be complete (FIG. 12A) or partial (FIG. 12B). Other partial sequences of tumour biomarkers may be used, such as those of gp100 (FIG. 12C) or of tyrosinase (FIG. 12D). Many other examples of complete or partial sequences of tumour biomarkers may be used.
    Encapsidation plasmid: This plasmid is identical to that described in Example 1 (the expression cassette of which is as described in FIG. 5).
    Envelope plasmid (pENV): This plasmid is identical to that described in Example 1 (the expression cassette of which is as described in FIG. 3).
  2. Production of the Batches and Titration
  Production of the batches and titration are carried out according to method P2, as described in Example 1, using one of the following expression plasmids:
    pcDNA-EF1.Fluorescent Gene.MS2 12× (the expression cassette of which is as described in FIG. 1).
    pILV-EF1.Fluorescent Gene.WPRE (the expression cassette of which is as described in FIG. 4B).
    pcDNA.EF1.PPRV.MAGEA3.IRES.GFP.WPRE.MS2 12× (the expression cassette of which is as described in FIG. 11A).
    pILV.EF1.MAGEA3.IRES.GFP.WPRE (the expression cassette of which is as described in FIG. 12A).
  Titration of the batches is carried out by a method identical to that described in Example 1.
II. Transduction of Murine Dendritic Cells (BMDCs)
  The murine dendritic cells are prepared by a method identical to that described in Example 1.
  1. Transduction of the murine dendritic cells with a single tumoral antigen, by an RLP-MAGE A3-IRES-GFP
  The dendritic cells transduced by the RLP.MAGE A3-IRES-GFP particle were the subject of development connected with characterization of expression of fluorescence analysed by flow cytometry over an increasing range of RLP particles from 0.1 pg p24 to 5 pg p24 and at different analysis times (1, 2, 3 and 4 days post-transduction). A negative control of transduction is prepared with the medium containing only the transduction agent Polybrene® at 4 µg/mL (Sigma).
  The dendritic cells are phenotyped by immunolabeling with anti-CD11c, anti-CD86, anti-CD80 specific antibodies (Miltenyl Biotec) and characterized by flow cytometry.
  2. Transduction of the Murine Dendritic Cells with a Single Tumoral Antigen, by an ILV-MAGE A3-IRES-GFP
  The dendritic cells transduced by the ILV-MAGE A3-IRES-GFP vector were the subject of development connected with characterization of expression of fluorescence analysed by flow cytometry over an increasing range of lentiviral particles ILV from a multiplicity of infection MOI from 5 to 75 and at different analysis times (1, 2, 3 and 4 days post-transduction). A negative control of transduction is prepared with the medium containing only the transduction agent Polybrene® at 4 µg/mL (Sigma).
  The dendritic cells are phenotyped by immunolabeling with anti-CD11c, anti-CD86, anti-CD80 specific antibodies (Miltenyi Biotec) and characterized by flow cytometry.

3. Phenotyping and Characterization of the Cells 3.1 Immunolabeling of Murine Dendritic Cells At each analysis time, the cells are transferred to the wells of a conical-bottom 96-well culture plate. The cells are washed with a solution of PBS 1× pH 7.4, 5% FCS and centrifuged at 300 g for 5 minutes. The supernatant is removed by inversion.

The dendritic cells are phenotyped by immunolabeling with the following specific antibodies conjugated with fluorochromes: anti-CD11c, anti-CD86, anti-CD80 (Miltenyl Biotec). For this, mixtures of solution of antibodies are prepared and 50 μl per well is deposited on the dendritic cells recovered. The cells are incubated for 20 minutes at room temperature in the dark. 50 μl of PBS 1× pH 7.4, 5% FCS is added and the cells are centrifuged at 300 g for 5 minutes. The supernatant is removed by inversion. The cells are taken up in 100 μl of PBS 1× pH 7.4, 5% FCS. The cells are centrifuged at 300 g for 5 minutes. The supernatant is removed by inversion. The cells are taken up in 100 μl of PBS 1× pH 7.4, 5% FCS and analysed by flow cytometry.

3.2 Flow Cytometry

The immunolabelled dendritic cells are analysed by flow cytometry (Miltenyi Biotec) and analysed. The samples were calibrated according to their size (SSC) and their granularity (FSC). The cells are characterized on the MacsQuantVYB (Miltenyi Biotec) and analysed with the MacsQuant software (Miltenyi Biotec).

III. Presentation of the Study Model

1. Renca Tumour Model

This model uses the tumour cells of murine (Balb/c) renal cancer of the Renca type. These murine cells are transduced beforehand with the ILV.EF1.MAGE A3.IRES.GFP vector (MOI 100) so as to express the MAGE A3 antigen, which is of human origin. The model then consists of reimplanting a predefined number of these cells ($1 \cdot 10^6$ cells) subcutaneously, in the flank of adult syngeneic Balb/c mice. A preliminary study made it possible to determine the number of cells to reimplant for generating a tumour that develops in all the animals, without reaching limit points (tumour>2 mm³, weight loss of the animals >20% of the weight on the day of implantation of the tumour) too quickly. The animals are obtained from a registered breeder (Janvier Europe or Charles River Labs) and the protocol elaborated for all of these experiments was submitted to and approved by a local ethics committee (CEEA-122 ethics committee).

2. Reimplantation of the Modified Dendritic Cells

The BMDCs are transduced as described in Example 1 (2.4) with particles of the RLP type (Example 1, paragraph 2.4.1) or ILV type (Example 1, paragraph 2.4.2) and are reimplanted on the day after transduction in the Balb/c mice, intradermally at the level of the inguinal lymph node located on the same side as the tumour reimplantation. Different quantities of cells may be reimplanted for evaluating their therapeutic power in this model.

3. Monitoring Tumour Development

All the animals are checked daily for their general condition. Three times a week, they are weighed and tumour development is measured manually using a caliper gauge. Tumour volume is given in mm³ according to the following formula: $V=a*(b^2/2)$ where a=the largest diameter and b=the smallest diameter. For ethical reasons, tumour development is limited to a volume of 2000 mm³, and animals reaching this limit or that have lost more than 20% of their initial weight (=on the day of reimplantation of the tumour cells) are sacrificed.

Figure 13A:
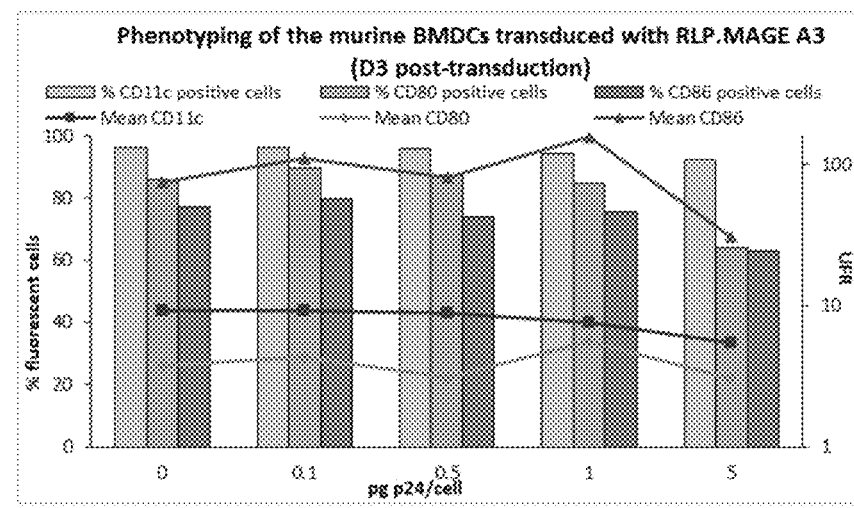
FIG. 13A is a diagram illustrating the phenotyping of BMDC cells transduced with a particle according to the invention comprising RNAs coding the MAGE A3 antigen.
Figure 13B:
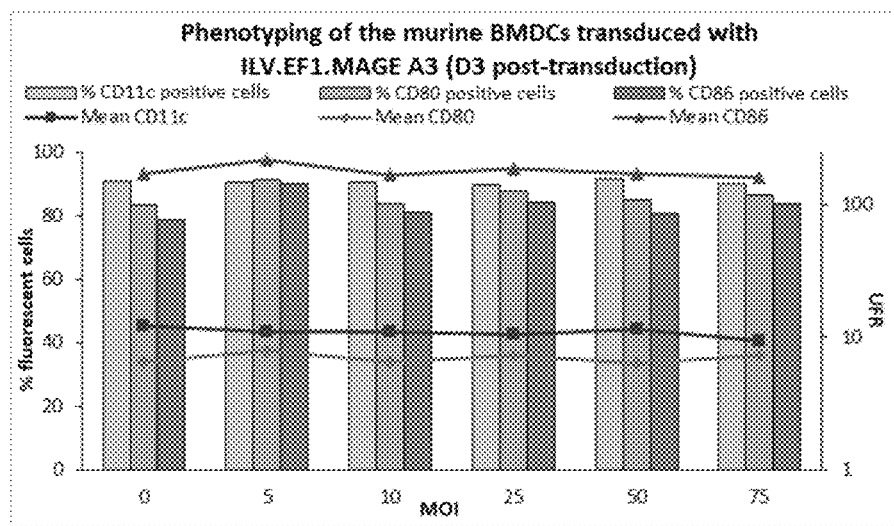
FIG. 13B is a diagram illustrating the phenotyping of BMDC cells transduced with an integrating lentiviral vector (ILV) comprising an RNA coding the MAGE A3 antigen.

IV. Results: Comparison of the Effectiveness of Expression of an Antigen by RLP and ILV A first experiment was carried out to test the effectiveness of antigen presentation of a tumoral antigen (MAGE A3) by murine dendritic cells (BMDCs). BMDCs were transduced by RLP.MAGE A3.IRES.GFP particles or an ILV.EF1. MAGE A3.IRES.GFP vector under the optimum conditions determined by tests with ZsGreen1 fluorescence. A range of MOI was done in both cases and the cells were phenotyped on the third day for expression of the specific markers of the dendritic cells (FIG. 13A and FIG. 13B). As before, these analyses show that the phenotype is not altered by the transduction, whatever the MOI applied.

Figure 14:
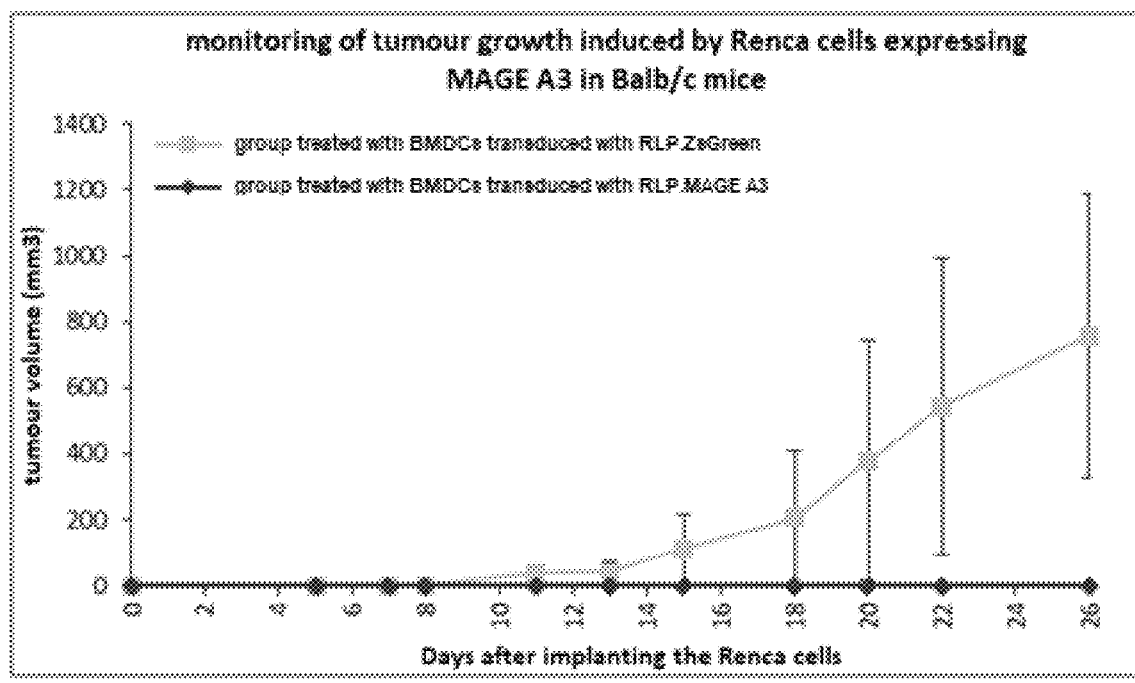
FIG. 14 is a diagram illustrating the monitoring of tumour growth induced by Renca cells expressing MAGE A3 In the mouse.

BMDCs transduced by RLP.ZsGreen1 or RLP.MAGE A3 particles were also used for testing the development of tumours expressing MAGE A3 In vivo, in the Balb/c mouse. Two groups of mice received syngeneic tumour cells of the Renca type ($0.75 \times 10^6$ cells), themselves modified beforehand to express the MAGE A3 tumoral antigen of human origin. On the same day, these animals received intradermally, near the corresponding inguinal lymph node, a suspension of BMDCs ($1 \times 10^5$ cells) modified by RLP-ZsGreen1 for the control group or by RLP.MAGE A3 for the test group. Monitoring of tumour development then showed that the animals that received the BMDC.MAGE A3's did not develop a tumour, in contrast to the animals in the control group (FIG. 14).

EXAMPLE 3

Figure 15:
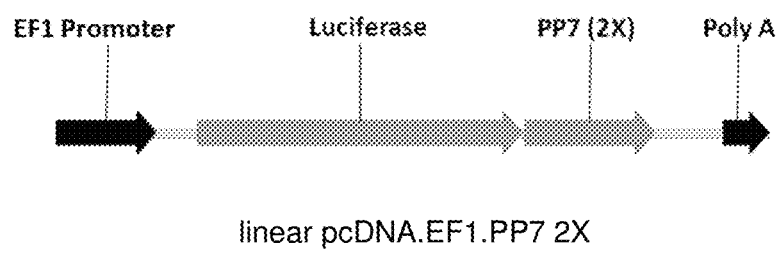
FIG. 15 shows the schematic diagram of the expression cassette derived from the expression plasmid bearing luciferase as the RNA sequence of interest, used for the production of PP7RLP lentiviral particles, comprising the PP7 stem-loop motif repeated 2 times, according to the invention.

Effectiveness of a PP7 (IN)-RLP 2× Lentiviral Particle by Modification of the Integrase I. Preparation of the Viral Particle According to the Invention and of the Comparative Systems 1. Plasmid Construction Expression plasmid for a sequence of interest: The expression plasmid bears a promoter-sequence of interest-polyA expression cassette (FIG. 15 or FIG. 23) with or without an intron sequence or RNA-stabilizing sequence. In order to transport the mRNAs into the lentiviral particles, 2 repetitions of the stem-loop motif of the PP7 RNA (ctagaaaggagcagacgatatggcgtcgct-ccctgcag SEQ ID No.2 and ctagaaaccagcagag-catatgggctcgctggctgcag SEQ ID No.3) were inserted within an expression cassette downstream of the reporter gene (FIG. 15 or FIG. 23).

The promoter used may be the CMV or EF1 promoter (FIG. 15 or FIG. 23) but other promoters may be used. The sequence of interest may be a DNA coding a reporter protein such as native firefly luciferase (FIG. 15), a green (ZsGreen1) (FIG. 13), red (mCherry) or blue (mtBFP) fluorescent protein, or a cDNA coding a protein, for example the protein CRE. Preferably, the cDNA codes an immunogenic protein or an immunomodulating protein. The sequence of interest may also be that of an shRNA, miRNA, sgRNA, LncRNA or circRNA.

Figure 16:
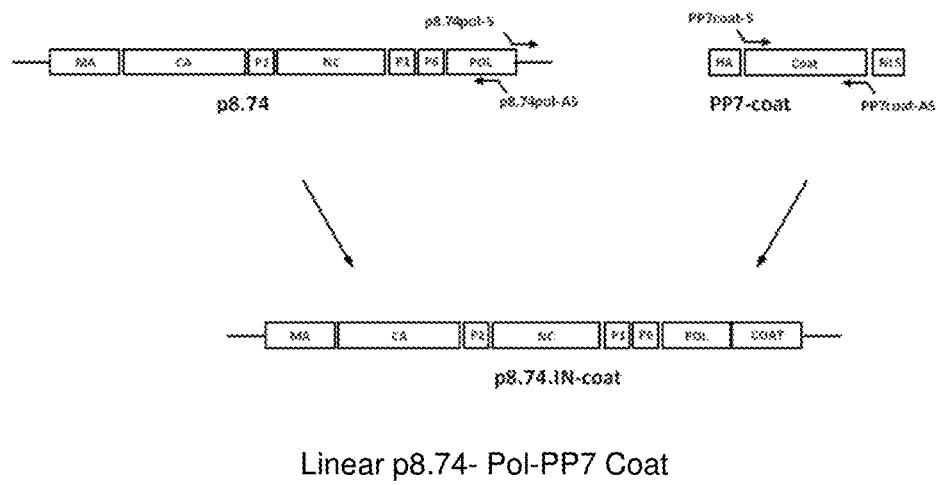
FIG. 16 shows a schematic diagram of the modification of the p8.74 lentiviral encapsidation plasmid in order to insert a binding domain in the sequence of the integrase.

Encapsidation plasmid: The lentiviral particle was modified to contain, within the integrase, the "Coat" protein sequence of the PP7 bacteriophage. The p8.74 encapsidation plasmid bearing the genes coding the structural and functional proteins (Gag, Pol) used for producing the PP7 (IN)-RLP 2× particles is modified in accordance with the strategy illustrated in FIG. 16: this p8.74 plasmid is used for generating, by assembly PCR, a plasmid on which the Coat protein of the PP7 phage is fused to the C-terminal domain of the integrase. This fusion, obtained by HpaI cloning, makes it possible to generate the P8.74-POL-PP7 Coat plasmid.

Figure 17:
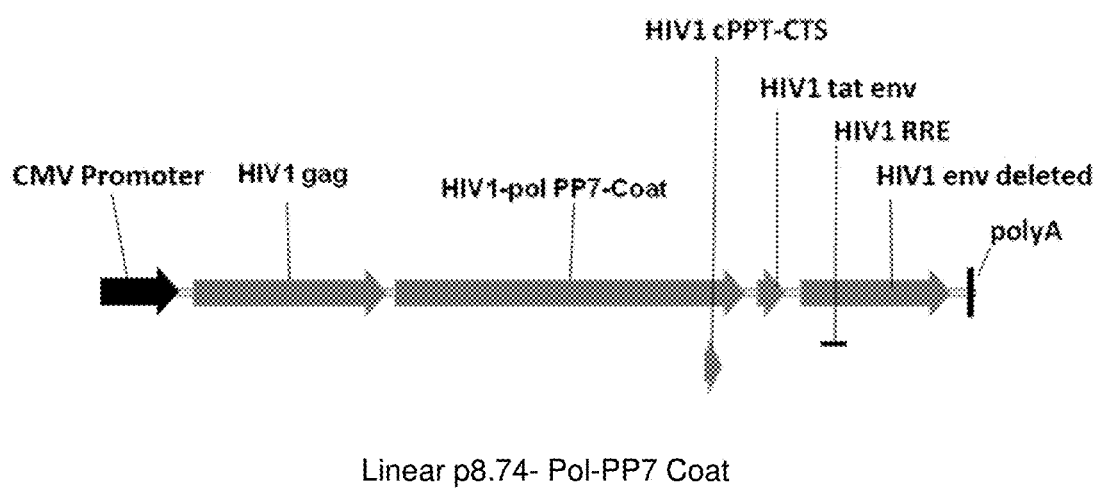
FIG. 17 shows a schematic diagram of the expression cassette derived from the encapsidation plasmid used for the production of PP7 (IN)-RLP lentiviral particles according to the invention, obtained by modifying the p8.74 lentiviral encapsidation plasmid shown in FIG. 16.

This gives the construct the expression cassette of which is illustrated in FIG. 17. The Pol coding sequence may be deleted or mutated in certain functional elements, for example such as the sequence coding reverse transcriptase (RT).

Envelope plasmid (pENV): This plasmid bears the gene coding an envelope protein, which may be VSV-G coding the envelope protein of the vesicular stomatitis virus (the expression cassette of which is as described in FIG. 3).

2. Production, Concentration/Purification and Titration of the Lentiviral Particles The lentiviral particles are produced as described in Example 1, and concentrated and purified according to method P2. The particles are titrated as described in Example 1.

II. Transduction of Murine Dendritic Cells (BMDCs)

The murine dendritic cells are prepared by a method identical to that described in Example 1.

1. Transduction of Murine Dendritic Cells with PP7 (IN)-RLP 2×

The dendritic cells are transduced by the PP7 (IN)-RLP.ZsGreen1 vector as described in Example 1 (paragraph 2.4), at MOI of 1 pg p24 per cell and analysed for their viability and expression of the ZsGreen1 fluorescence by flow cytometry at different analysis times (1, 2 and 3 days post-transduction). A negative control of transduction is prepared with only the medium containing the transduction agent Polybrene® at 4 µg/mL (Sigma).

The viability of the dendritic cells is determined by specific immunolabeling with "Viobility™ 485/520" (Miltenyl Biotec) and analysed by flow cytometry.

2. Phenotyping and Characterization of the Cells 2.1 Immunolabeling of Murine Dendritic Cells At each analysis time, the cells are transferred to the wells of a conical-bottom 96-well culture plate. The cells are washed with a solution of PBS 1× pH 7.4 and centrifuged at 300 g for 5 minutes. The supernatant is removed by inversion.

The viability of the dendritic cells is determined by specific immunolabeling with "Viobility™ 485/520" (Miltenyl Biotec) by a method identical to that described in Example 1.

2.2 Flow Cytometry

The immunolabelled dendritic cells are analysed by flow cytometry (Miltenyl Biotec) and analysed. The samples were calibrated according to their size (SSC) and their granularity (FSC). The cells labelled with Viobility™ are dead, therefore the viable cells are the negative cells (labelling by exclusion). The cells are characterized on the MacsQuantVYB (Miltenyi Biotec) and analysed with the MacsQuant software (Miltenyi Biotec).

III. Results

FIG. 24 shows measurement of cellular viability and the expression kinetics of ZsGreen1, of BMDCs (APCs) transduced with the PP7 (IN)-RLP.ZsGreen1 particles at a dose of 1 pg p24 per cell. The proportion of murine BMDCs transduced with the PP7 (IN)-RLP particles that express ZsGreen1 is 70%, starting from 24 h post-transduction and stably up to 3 days. The cells stay at the same level of viability over the 3 days of analysis; only the intensity of expression decreases over time. It is therefore possible to transport RNAs into the lentiviral particles with PP7-Coat in the integrase. Preferably, the PP7 (IN)-RLP particles are used for transporting RNAs bearing antigen sequences into APCs, such as BMDCs.

EXAMPLE 4

Demonstration of the Transfer of RNA Coding Several Antigens by an RLP Particle into Immune Cells I. Preparation of the Viral Particle According to the Invention and of the Comparative Systems 1. Plasmid Construction Expression plasmids for a sequence of interest: The expression plasmids bear a promoter-sequence of interest-polyA expression cassette with or without an intron sequence or RNA-stabilizing sequence. In order to transport the mRNAs into the lentiviral particles, 12 repetitions of the stem-loop motif of the MS2 RNA (ctagaaaacatgaggatcacccatgtctgcag, SEQ ID No.1) were inserted within an expression cassette downstream of the reporter gene. The promoter used may be the CMV or EF1 promoter but other promoters may be used. The sequence of interest may code an antigen or an epitope. Many biomarkers were identified on the tumour cells and their complete sequence and/or partial sequences are used in immunotherapy. For example, the sequence used for expressing the MAGEA3 antigen may be complete (FIG. 11A) or partial (FIG. 11B). Other partial sequences of biomarkers may be used, such as those of gp100 (FIG. 11C) or of tyrosinase (FIG. 11D). Many other examples of complete or partial sequences of tumour biomarkers may be used.

Figure 2:
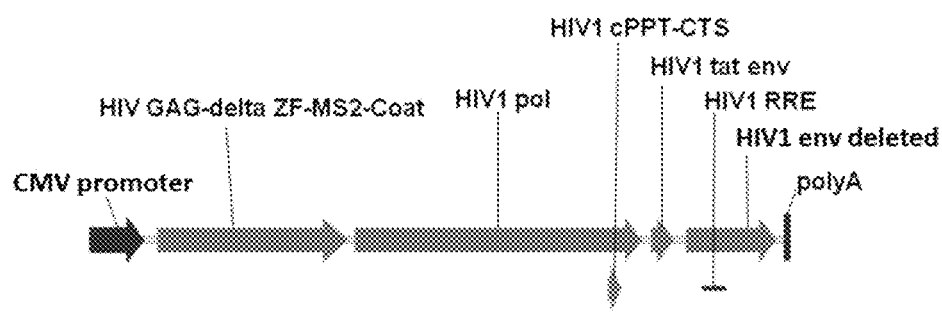
FIG. 2 shows a schematic diagram of the construction of the expression cassette derived from the p8.74 lentiviral encapsidation plasmid in which a binding domain MS2 Coat has been introduced into the nucleocapsid sequence, this encapsidation plasmid being used for producing MS2RLP lentiviral particles according to the invention.

Encapsidation plasmid: This plasmid is identical to that described in Example 1 (FIG. 2).

Figure 3:
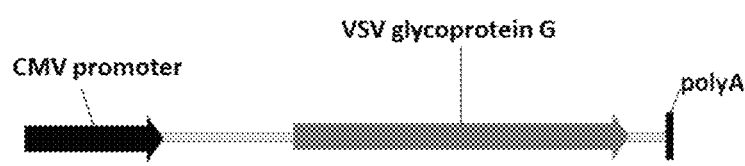
FIG. 3 is a schematic diagram of the construction of the expression cassette derived from the envelope plasmid.

Envelope plasmid (pENV): This plasmid is identical to that described in Example 1 (FIG. 3).

2. Production of the Batches and Titration

Production of the batches and titration are carried out according to method P2 described in Example 1, using one or more of the following expression plasmids:

Batch RLP MAGEA3: pcDNA.EF1.PPRV.MAGEA3. IRES.GFP.WPRE.MS2 12× (FIG. 11A).

Batch RLP TAAs: pcDNA.EF1long.PPRV.PS-AgMageA3. WPRE.MS2 12× (FIG. 11B)+pcDNA. EF1long. PPRV.PS-Aggp100.WPRE.MS2 12× (FIG. 11C)+ pcDNA.EF1long.PPRV.PS-AgTyrosinase.WPRE.MS2 12× (FIG. 11D).

Figure 1:
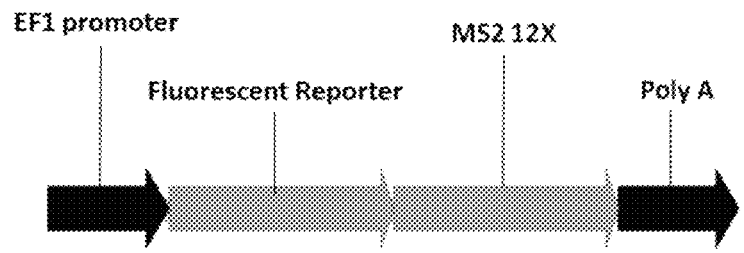
FIG. 1 is a schematic diagram of the construction of the expression cassette derived from the expression plasmid bearing, as RNA sequence of interest, a fluorescent reporter, this expression plasmid being used for the production of MS2RLP lentiviral particles according to the invention.

Batch RLP.ZsGreen1: pcDNA. EF1.Fluorescent Gene. MS2 12× (FIG. 1).

The respective proportions of the plasmids are as follows: 40% of the expression plasmid or expression plasmids (in the case of the RLP-TAAs), 30% of the p8.74 (or p8.74ΔZF) plasmid, 30% of the pENV plasmid.

II. Transduction of APCs

1. U937 line (ATCC® CRL-1593.2™)

The U937 cell line is a cell line established starting from the histiocytic lymphoma of a 37-year-old man that has numerous characteristics of monocytes. This model is much used for in vitro studies of differentiation of monocytes and macrophages. The U937 cells are cultured in Ultra Low Attachment (ULA) culture flasks at 100 000 cells per ml of RPMI 1640 medium in the presence of 10% of fetal calf serum (FCS), 1% penicillin/streptomycin, 2 mM L-glutamine (RPMI complete medium).

1.1 Transduction of the U937 Cells with RLP.MAGE A3.IRES.GFP Particles or Particles Containing a Mixture of 3 Tumoral Antigens (RLP-TAAs)

On the day of transduction, the cells are recovered and counted. They are resuspended to obtain a cellular suspension at 500 000 cells/ml in 500 µl of medium. Seeding ready for transduction is carried out in a 24-well ULA plate, at a rate of 500 µl per well and in triplicate.

The cells are transduced in RPMI complete culture medium supplemented with the following transfection agents: Polybrene® at 16 µg/mL and BX795 12 µM and incubated at +37° C./5% $CO_2$ for 4 hours. 500 µl of the transduction medium is added to each corresponding well, for which the transfection agents are present at a final concentration of 8 µg/mL of Polybrene® and 0.6 µM of BX795.

5 hours after transduction, 800 µl of the transduction medium (80%) is withdrawn and replaced with 800 µl of RPMI complete culture medium.

1.2 Recovery of the Cells

At 5 hours and 20 hours post-transduction, the cells are resuspended and a sample is put in a 15-ml tube, and then centrifuged at 200 g for 5 minutes to obtain pellets. The supernatant is discarded and the cells are washed in 1 ml of PBS 1× before being centrifuged again at 200 g for 5 minutes. The supernatant is discarded and the cellular pellet is resuspended in 1 ml of Trypsin 0.05%-0.53 mM EDTA (Corning). The cells are incubated for 5 minutes at 37° C. At the end of incubation, 2 ml of RPMI complete culture medium is added to the cellular suspension. The cells are centrifuged at 200 g for 5 minutes, then the supernatant is discarded and the cells are washed with 1 ml of PBS 1× before being centrifuged for one last time at 200 g for 5 minutes. The supernatant is discarded and the cells are frozen immediately at −80° C. in the form of dry pellets.

1.3 Extraction of the Total RNAs

Each dry pellet is placed on ice, to thaw slowly. 1 ml of TRIzol solution is added to each dry pellet at room temperature and the cells are incubated for 5 minutes before adding 200 µl of chloroform. The samples are homogenized by inverting 10 times and incubated for 2-3 minutes at room temperature. The samples are centrifuged at 12000 g for 15 minutes, at +4° C. At the end of centrifugation, the samples are placed on ice. The upper phase is transferred to a new tube (500-600 µl). An equivalent volume of 70° ethanol is added and then the samples are homogenized using a Vortex.

The total RNAs are purified according to the protocol of the "RNA purification mini kit" (Ambion). Elution is carried out in 30 µl of pure water solution per sample. The RNAs of the samples are assayed using the Nanodrop and then the samples are stored at −80° C.

1.4 Reverse Transcription of the RNAs

Reverse transcription of the RNAs to complementary DNA is carried out on 500 ng of RNA of each sample using the "Maxima First Strand" enzyme (ThermoFisher), following the suppliers recommendations.

1.5 Amplification of the cDNAs by RT-qPCR

The amplifications are carried out on 5 µl of cDNA at 1/10th dilution in ultrapure water, with the real-time PCR mix, SYBR® Premix Ex Taq (Takara—cat RR420L), in the presence of 200 nM of sense and antisense oligonucleotides in a final volume of 20 µl.

5 µl of cDNA at 1/10th dilution is added to each well.

Real-time PCR is carried out with a StepOnePlus thermocycler (Applied Biosystems) with the SYBR®Green chemistry according to the following protocol: 1 cycle of 30 seconds at 95.0° C. then 40 cycles comprising 5 seconds at 95.0° C. and 30 seconds at 60.0° C.

The sense oligonucleotides used are:

```
                                            (SEQ ID No. 4)
Q-hGAPDH-S (GACAAGCTTCCCGTTCTCAG)

(SEQ ID No. 5)
Q-MAGEA3-F (CTGCCGACCACCATGAACTA)

(SEQ ID No. 6)
Q-PSMAGEDC-F (TCAGCACTCTTTGAGGATCTAATGA)

(SEQ ID No. 7)
Q-PSTyrDC-F (ATGAGCCAGGTGCTTAACAACA)

(SEQ ID No. 8)
Q-PSGP100DC-F (TGGCGCCTCAGCACTCTT)
```

The antisense oligonucleotides used are:

```
                                            (SEQ ID No. 9)
Q-hGAPDH-AS (GAGTCAACGGATTTGGTCGT)

(SEQ ID No. 10)
Q-MAGEA3-R (GGTTGCTGGAGTCCTCATAGGA)

(SEQ ID No. 11)
Q-PSMAGETyrDC-R (GGTAGGCAATGAGGACGATGA)

(SEQ ID No. 12)
Q-PSGP100DC-R (ACCTGGTCCATGATGGTGAAG)
```

The combinations of the pairs of oligonucleotides to be used are as follows, depending on the targets:
Target hGAPDH with Q-hGAPDH-S and Q-hGAPDH-AS
Target MAGEA3 with Q-MAGEA3-F and Q-MAGEA3-R
Target PS-MAGEDC with Q-PSMAGEDC-F and Q-PSMAGETyrDC-R
Target PS-TyrDC with Q-PSTyrDC-F and Q-PSMAGETyrDC-R
Target PS-Gp100DC with Q-PSGP100DC-F and Q-PSGP100DC-R Experiments for validation of the specificity of the oligonucleotides had been conducted beforehand.

2. Preparation of the Immature Human Dendritic Cells (IDCs, Also Called hDCs)

The immature human dendritic cells (hDCs) are prepared by a method identical to that described in Example 1 (part II, 2.1).

2.1 Transduction of Human Dendritic Cells with RLP.Zs-Green1 Particles. RLP.MAGE A3 Particles or Particles Containing a Mixture of 3 Tumoral Antigens (RLP-TAAs)

Transduction of the hDCs is carried out by a method identical to that described in Example 1 (part II, paragraph 2.3). The cells are transduced with 4 pg of p24/cell and are analysed at different times (5 h, 20 h post-transduction).

A negative control of transduction is prepared with the medium containing only the transduction agent Polybrene® at 4 µg/mL (Sigma).

The dendritic cells are analysed on the day of transduction and at the different analysis times, by RT-qPCR on the RNAs obtained from pellets of transduced cells.

2.2 Recovery of the Cells

At 5 hours and 20 hours post-transduction, the culture supernatants are withdrawn from the wells containing the hDCs that have adhered to the plastic culture plate. They are washed with 0.5 ml of PBS 1×, which is then removed. The cells then receive 0.25 ml of Trypsin 0.05%-0.53 mM EDTA (Corning) and are incubated for 2 minutes at 37° C. At the end of incubation, 0.25 ml of RPMI complete culture medium is added and the hDCs are recovered by scraping the well. The cells are centrifuged at 200 g for 5 minutes. The wells are washed with 0.5 ml of PBS 1×, which is used for resuspending the pellets of hDCs after centrifugation. All of the hDCs thus harvested are centrifuged again for 5 minutes at 200 g. The supernatant is discarded and the cells are washed one last time with 0.5 ml of PBS 1× before being centrifuged at 200 g for 5 minutes. The supernatant is discarded and the cells are frozen immediately at −80° C. in the form of dry pellets.

2.3 Extraction of the Total RNAs

The RNAs are prepared by a method identical to that described in this same example at II.1.3 with the RNA purification mini kit from Ambion. Elution is carried out in 30 µl of solution of pure water per sample. Assay of the RNAs of the samples is carried out using the Nanodrop and then the samples are stored at −80° C.

2.4 Reverse Transcription of the RNAs

Reverse transcription of the RNAs to complementary DNA is carried out on 500 ng of RNA by the method described in this same example at II.1.4.

2.5 Amplification of the cDNAs by RT-qPCR

Amplification of the cDNAs by RT-qPCR is carried out by the method described in this same example in paragraph II.1.5.

III. Results

Specific analysis by RT-qPCR makes it possible to demonstrate the transfer of RNA coding the 3 antigens (PS-MAGEA3, PS-GP100 and PS-TYR) by RLP particles into APCs, in particular into U937 cells and into human dendritic cells, at 5 h and 20 h post-transduction (FIG. 26 and FIG. 27 and FIG. 29 and FIG. 30, respectively). The results obtained are analysed and interpreted according to the presence or absence of significant specific amplification during real-time quantitative PCR (RT-qPCR).

The results show that the different RNAs contained in the particles, whether they are of a single type as is the case for the RLP-MAGE A3 particles (FIG. 25 and FIG. 28) or of three different types, as for the RLP-TAAs particles (FIG. 26 and FIG. 27 and FIG. 29 and FIG. 30), are therefore properly transferred into the APCs by the RLP particles. In the case of the U937 cell line, the relative quantities of the different RNAs are significant starting from 5 h post-transduction (FIG. 26) and they increase at 20 h post-transduction (FIG. 27). In the case of the hDC primary cells, the relative levels of specific RNAs are significant at 20 h (FIG. 30) even if they are less pronounced at 5 h (FIG. 29). The RLP particles are therefore effective for transferring molecules of RNAs coding different antigenic peptides into APCs (lines and primary cells). This constitutes a therapeutic advantage in the efficacy of the treatment with modified immune cells, and APCs in particular. The RLP particles are therefore included in an immunotherapy strategy, based on modulating the specificity of the immune response.

EXAMPLE 5

Evaluation of the Effectiveness of an RLP Particle for Expression of Multiple Antigens I. Preparation of the Viral Particle According to the Invention and of the Comparative Systems 1. Plasmid Construction 1.1 Plasmids for Producing MS2RLP Lentiviral Particles According to the Invention Expression plasmids for a sequence of interest: The expression plasmids bear a promoter-sequence of interest-polyA expression cassette with or without an intron sequence or RNA stabilizing sequence, as described in FIG. 12B, FIG. 12C and FIG. 12D. In order to transport the mRNAs into the lentiviral particles, 12 repetitions of the stem-loop motif of the MS2 RNA (ctagaaaacatgaggatcacccatgtctgcag, SEQ ID No.1) were inserted within an expression cassette downstream of the reporter gene. The promoter used may be the CMV or EF1 promoter but other promoters may be used. The sequence of interest may code an antigen or an epitope. Many biomarkers were identified on the tumour cells and their complete sequence and/or partial sequences are used in immunotherapy. Many other examples of complete or partial sequences of tumour biomarkers may be used.

Encapsidation plasmid: This plasmid is identical to that described in Example 1 (the expression cassette of which is as described in FIG. 2).

Envelope plasmid (pENV): This plasmid is identical to that described in Example 1 (the expression cassette of which is as described in FIG. 3).

1.2 Plasmids for Producing Integrative Lentiviral Vectors ILV

Expression plasmids for a sequence of interest: The expression plasmid bears a promoter-sequence of interest expression cassette. The sequence of the gene of interest may be for example that of a fluorescent reporter (FIG. 4B), or that of an antigen or an epitope. Many biomarkers were identified on the tumour cells and their complete sequence and/or partial sequences are used in immunotherapy. For example, the sequences used for expressing MAGEA3 may be complete (FIG. 12A) or partial (FIG. 12B). Other partial sequences of tumour biomarkers may be used, such as those of gp100 (FIG. 12C) or of tyrosinase (FIG. 12D). Many other examples of complete or partial sequences of tumour biomarkers may be used. This plasmid may contain other elements such as the native sequence WPRE (Woodchuck Hepatitis Virus Post-transcriptional Regulatory Element) or the cPPT/CTS sequence. Viral pathogenicity is eliminated by substitution of regions of the viral genome required for retroviral replication by the transgene.

Encapsidation plasmid: The p8.74 encapsidation plasmid bearing the genes coding the structural and functional proteins (Gag, Pol) is used for producing the integrative lentiviral vectors (the expression cassette of which is as described in FIG. 5).

Envelope plasmid (pENV): This plasmid bears the gene coding an envelope protein, which may be for example the sequence of the VSV-G gene coding the envelope protein of the vesicular stomatitis virus (the expression cassette of which is as described in FIG. 3). 2. Production of the Batches and Titration Production of the batches is carried out according to method P2, as described in Example 1, using one of the following expression plasmids:

Batch RLP-PS-MAGEA3/Gp100/Tyr, also called RLP-TAAs: pcDNA.EF1long.PPRV.PS-AgMAGEA3.WPRE.MS2 12× (the expression cassette of which is as described in FIG. 11B)+pcDNA.EF1long.PPRV.PS-Aggp100.WPRE.MS2 12× (the expression cassette of which is as described in FIG. 11C)+pcDNA.EF1long.PPRV.PS-AgTyrosinase.WPRE.MS2 12× (the expression cassette of which is as described in FIG. 11D).

Batch RLP. MAGEA3.IRES.GFP, also called RLP-MAGEA3:

pcDNA.EF1.PPRV.MAGEA3.IRES.GFP.WPRE.MS2 12× (the expression cassette of which is as described in FIG. 11A).

Batch ILV.EF1.PS-MAGEA3/Gp100/Tyr, also called ILV-TAAs: pILV.EF1.PS-AgMAGEA3.WPRE (FIG. 12B)+pILV.EF1.PS-Aggp100.WPRE (the expression cassette of which is as described in Figure XIIc)+ pILV.EF1.PS-AgTyrosinase.WPRE (the expression cassette of which is as described in FIG. 12D).

The respective proportions of the plasmids are as follows: 40% of the expression plasmid or expression plasmids (in the case of the RLP-TAAs or ILV-TAAs), 30% of the p8.74 (or p8.74ΔZF) plasmid, 30% of the pENV plasmid.

Titration of the batches is carried out according to the method identical to that described in Example 1.

II. Description of the Models Used

1. Cellular Models 1.1 Renca Tumour Model

Figure 12C:
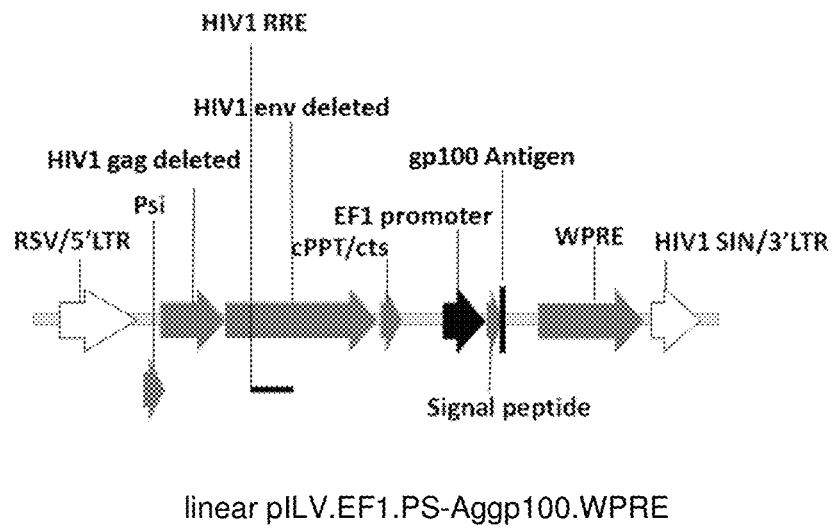
FIG. 12C is a schematic diagram of the construction of the expression cassette derived from the expression plasmid bearing, as RNA sequence of interest, a partial antigen sequence coding the gp100 antigen (PS-gp100 or PS-GP100), this expression plasmid being used for the production of integrative lentiviral vectors (ILV)
Figure 12D:
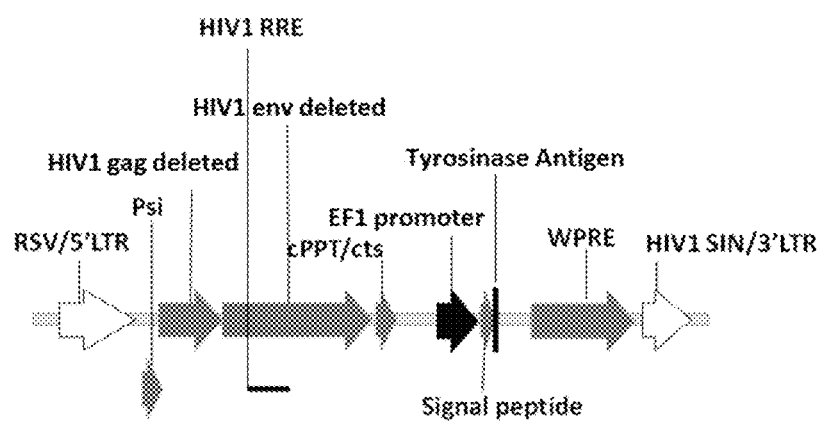
FIG. 12D is a schematic diagram of the construction of the expression cassette derived from the expression plasmid bearing, as RNA sequence of interest, a partial antigen sequence coding tyrosinase (PS-Tyr or PS-TYR), this expression plasmid being used for the production of integrative lentiviral vectors (ILV)

This model is that described in Example 2, for which Renca tumour cells are used, which will have been transduced beforehand at MOI 100 with the ILV.EF1.PS-MAGEA3/Gp100/Tyr vector containing a mixture of the 3 expression cassettes the expression cassettes of which are those described in FIG. 12B, FIG. 12C and FIG. 12D so as to express stably the antigenic peptides MAGE A3, gp100 and tyrosinase, all three of human origin. The model then consists of reimplanting $0.75 \cdot 10^6$ of these cells subcutaneously in the flank of adult syngeneic BALB/c mice. The animals are obtained from a registered breeder (Janvier Europe) and the protocol elaborated for all of these experiments was submitted to and approved by a local ethics committee (CEEA-122 ethics committee).

All the animals are checked daily for their general condition. Twice weekly, they are weighed and tumour development is measured manually using a caliper. The tumour volume is given in $mm^3$ according to the following formula: $V=a*(b^2/2)$ where a=the largest diameter and b=the smallest diameter.

1.2 Preparation of the Murine Lymphocytes

The murine lymphocytes are prepared from spleen of wild-type BALB/c mice or of mice that have developed a tumour of the Renca type >1 $mm^3$. The spleen is recovered after euthanasia of the animal by cervical dislocation. It is dissociated mechanically by crushing on a 70 μm cellular sieve. The cellular suspension is centrifuged for 5 minutes at 300 g, at +4° C. The cellular pellet is then taken up in 10 ml of cold MACS buffer, the suspension is filtered on a 40-μm cellular sieve placed on a 50-ml tube, and then a cell count is carried out. The cellular suspension is centrifuged for 10 minutes at 300 g at +4° C. before proceeding to positive sorting for expression of the CD8 marker by a method identical to that described in Example 1. The positive fraction is recovered by washing the sorting column, not using the magnet, with 1 ml of MACS buffer. This fraction is made up to 5 ml with cold MACS buffer and then a cell count is carried out. The cellular suspension is centrifuged for 10 minutes at 300 g at +4° C., and the cells are resuspended at a concentration of $1.10^6$ cells per ml in PBS 1×.

1.3 CFSE Labeling of the Sorted Murine CD8+ Splenocytes

Figure 18:
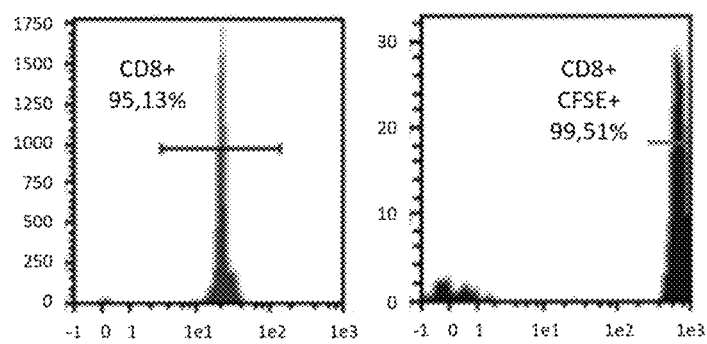
FIG. 18 shows the expression profiles of the murine CD8 marker and of CFSE on the cells derived from spleens of BABL/c mice, wild-type or that have developed a tumour, after magnetic sorting for CD8 expression and then CFSE labelling.
Figure 18:
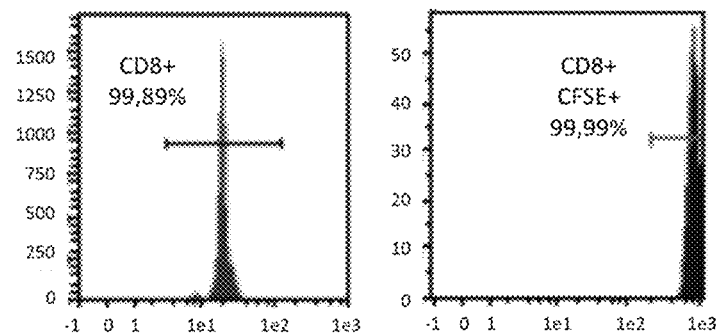

The CD8+T lymphocytes obtained from sorting of the murine splenocytes are labelled with carboxyfluorescein succinimidyl ester (CellTrace™ CFSE dye, Invitrogen/thermoFisher Scientific) by the following method: a cellular suspension at $1.10^8$ cells per ml is prepared in PBS 1×. The stock solution of CFSE is at 1 mM in DMSO, and 2 μl of this solution per ml of cellular suspension is added so as to obtain lymphocytes labelled at 2 μM. The cells are then incubated for 20 min at 37° C., protected from light. The reaction is stopped by diluting the cells 5 times in RPMI supplemented with 1% of fetal calf serum and incubating the suspension again for 5 min. The cellular suspension is then centrifuged for 5 minutes at 300 g at room temperature, and the cells are resuspended at a concentration of $1.6 \times 10^6$ cells per ml in RPMI 1640 medium supplemented with 10% of fetal calf serum, 1% penicillin/streptomycin, 2 mM L-glutamine to be co-cultured at different ratios with murine BMDCs, in a flat-bottom 96-well plate of the ULA type (Corning). After labelling, the CD8+T lymphocytes thus obtained are analysed by flow cytometry (Miltenyi Biotec) in the presence of an anti-CD8 antibody for monitoring the purity of the sorted population and the CFSE labelling (FIG. 18).

1.4 Preparation of the Murine Dendritic Cells

The murine dendritic cells are prepared by a method identical to that described in Example 1.

2. Transduction of the Immune Cells and Analysis of the Proliferative Response 2.1 Transduction of the Murine Dendritic Cells (BMDCs) with RLP.MAGE A3.IRES.GFP Particles or RLP.TAAs Particles Containing a Mixture of 3 Tumoral Antigens (RLP-PS-MAGEA3/Gp100/Tyr)

On the 7th day of culture the BMDC dendritic cells are transduced by the RLP.MAGE A3.IRES.GFP particles or by the RLP-PS-MAGEA3/Gp100/Tyr particles (mixture of the 3 expression plasmids the expression cassettes of which are those described in FIG. 11B, FIG. 11C and FIG. 11D) at a rate of 3 pg p24 per cell. A negative control of transduction is prepared with the medium containing only the transduction agent Polybrene® at 4 μg/mL (Sigma).

The dendritic cells are phenotyped on the day of transduction and 24 h later by immunolabeling with anti-CD11c, anti-CD86, anti-CD80 specific antibodies (Miltenyi Biotec) and characterized by flow cytometry.

2.2 Co-Culture of the CFSE-Labelled CD8+T Lymphocytes with the Syngeneic BMDCs

The CFSE-labelled CD8+T lymphocytes, derived from the BALB/c mice, wild-type or that have developed a Renca tumour, are cultured in the presence of syngeneic murine BMDCs transduced either with the RLP.MAGE A3.IRES.GFP particles, or with the RLP-PS-MAGEA3/Gp100/Tyr particles, or with non-transduced BMDCs. Two ratios were tested in the case of the co-cultures with the BMDCs transduced with the RLP-PS-MAGEA3/Gp100/Tyr particles: 1 BMDC to every 2 CD8+T lymphocytes (1DC: 2T) or 1 BMDC to every 4 CD8+T lymphocytes (1DC:4T). The ratio of the CD8+T lymphocytes to the BMDCs transduced with the RLP.MAGE A3.IRES.GFP particles is 1 BMDC to every 2 CD8+T lymphocytes (1DC:2T). These co-cultures are carried out in a final volume of 200 μl of RPMI 1640 medium supplemented with 10% of fetal calf serum, 1% penicillin/streptomycin, 2 mM L-glutamine, in a flat-bottom 96-well plate of the ULA type (Corning). The BMDCs are incubated at a rate of 40 000 cells per well and the number of CD8+T lymphocytes therefore varies from 80 000 to 160 000 cells per well.

2.3 Analysis of the Proliferative Response of the CD8+T Lymphocytes

Five days after starting co-culture, the mixtures of cells are recovered from the culture plates and are transferred to the wells of a conical-bottom 96-well culture plate in order to be labelled for the analyses by flow cytometry. The cells are washed with a solution of PBS 1× pH 7.4, 5% FCS and centrifuged at 300 g for 5 minutes. The supernatant is removed by inversion. The lymphocytes are analysed by immunolabeling with a fluorochrome-conjugated anti-CD8 antibody (Miltenyl Biotec) by the method described above in Example 1. The cells are taken up in 100 μl of PBS 1× pH 7.4, 5% FCS and analysed by flow cytometry, both according to their expression for the CD8 marker (which makes it possible to discriminate them from the BMDCs still present in the suspensions) and the expression of CFSE, the relative fluorescence level of which is halved at each cell division, which therefore makes it possible to quantify the proliferative response of the cells.

FIG. 19 shows the expression profiles of the CFSE obtained with CD8+T lymphocytes cultured alone as well as those obtained after the 5 days of co-culture with the BMDCs, non-transduced or transduced with the RLP-PS-MAGEA3/Gp100/Tyr particles.

2.4 Flow Cytometry

The immunolabelled lymphocyte cells are analysed by flow cytometry (Miltenyi Biotec). The samples were calibrated according to their size (SSC) and their granularity (FSC). The cells are characterized on the MacsQuantVYB (Miltenyi Biotec) and analysed with the MacsQuant software (Miltenyi Biotec).

II. Results

In these experiments, BMDCs, non-transduced, transduced by the RLP.MAGE A3.IRES.GFP particles or transduced by the RLP-PS-MAGEA3/Gp100/Tyr particles were co-cultured at different ratios with T lymphocytes sorted as a function of their expression of the CD8 marker specific to the suppressor T lymphocytes—Involved in development of the tumoral response—and labelled beforehand with CFSE. FIG. 18 validates the purity of the cells obtained from the spleens of the wild-type and tumoral mice (expression of the CD8 marker in the whole population), as well as the labelling with CFSE on D0. FIG. 19 shows that the CFSE-labelled CD8+T lymphocytes co-cultured for 5 days with BMDCs (ratio DC:2T) respond by proliferating. This is reflected in cytometry by a decrease in fluorescence intensity of the CFSE labelling towards the left, on one or more peaks. The analysis relates to the percentage of cells in these peaks. The profiles shown are representative of 3 experiments. The response of the CD8+T lymphocytes from a wild-type mouse is similar whether they are in contact with transduced or non-transduced BMDCs. This phenomenon is explained by the fact that naive lymphocytes brought into contact with dendritic cells are capable of proliferating, even in the absence of antigen (Q. Ge et al. PNAS. 2002 99(5): 2983-2988). On the contrary, the CD8+T lymphocytes from a mouse that has developed a Renca tumour expressing the 3 tumoral antigens (MAGE A3/gp100/Tyr) show little response to the non-transduced BMDCs. They respond specifically when they are exposed again to the antigens expressed by the tumour, during co-culture with the BMDCs transduced by the RLP-PS-MAGEA3/Gp100 Tyr particles (31.42% of the cells proliferate in this case, versus 14.94% only in the presence of the non-transduced BMDCs). It was shown that certain factors produced by the tumour (IL-10, PGE2) may lead to development of a phenomenon of anergy of the T lymphocytes in vivo (M. Ahmadi et al. Cancer Res. 2008 Sep. 15; 68(18): 7520-7529). This explains why these CD8+T lymphocytes proliferate much less than the naive CD8+T lymphocytes when they are exposed to non-transduced BMDCs.

As a control, the CFSE-labelled CD8+T lymphocytes cultured alone for 5 days, without being exposed to dendritic cells, do not proliferate and their CFSE expression profile is then similar to that observed on D0 (FIG. 18). The profiles are identical regardless of the origin of the CD8 T lymphocytes (wild-type or tumoral mouse).

FIG. 20 shows the analysis of the proliferative response of the CD8+T lymphocytes co-cultured with BMDCs transduced with the RLP-PS-MAGEA3/Gp100/Tyr particles, with respect to the response of these same CD8+T lymphocytes co-cultured with non-transduced BMDCs. The analyses were carried out on 3 different co-cultures with CD8+T lymphocytes obtained from three wild-type mice or from three mice that have developed a Renca tumour, the BMDCs also being derived from 3 different cultures. The responses of the CD8+T lymphocytes were analysed from co-cultures at a ratio of 1DC:2T or at a ratio of 1DC:4T. The relative proliferative response is given by the ratio of the percentage of cells proliferating in response to the BMDCs transduced with the RLP-PS-MAGEA3/Gp100/Tyr particles with respect to the percentage of the cells responding non-specifically to the non-transduced BMDCs. The results show that the CD8+T lymphocytes from the mice that have developed a Renca tumour expressing the 3 antigens associated with human tumours (TAAs) respond specifically to new stimulation by these TAAs (2.67 for the 1DC:2T co-cultures and 3.90 for the 1DC:4T co-cultures) whereas the CD8+T lymphocytes from naive mice respond similarly to the BMDCs transduced with the RLP-PS-MAGEA3/Gp100/Tyr particles (1.59 for the 1DC:2T co-cultures and 1.78 for the 1DC:4T co-cultures).

Finally, FIG. 21 compares the relative proliferative responses of the CD8+T lymphocytes co-cultured under condition 1DC:2T with BMDCs transduced by RLP.MAGEA3.IRES.GFP particles or transduced by the RLP-PS-MAGEA3/Gp100/Tyr particles. As presented in FIG. 20, these analyses show that the CD8+T lymphocytes obtained from mice that have developed a Renca tumour bearing the 3 TAAs respond more markedly than the CD8+T lymphocytes obtained from wild-type mice to the BMDCs transduced with the RLP-PS-MAGEA3/Gp100/Tyr particles. Moreover, they respond specifically to BMDCs transduced with particles bearing just one of these antigens (MAGE A3).

Taken together, these results show that the BMDCs transduced with the RLP-PS-MAGEA3/Gp100/Tyr particles are therefore certainly capable of presenting the antigenic peptides corresponding to the 3 TAAs (MAGE A3, gp100 and tyrosinase). The RNA molecules corresponding to the 3 peptides are therefore taken charge of by the cellular machinery specific to the antigen-presenting cells that present these peptides on the surface for a sufficiently long time and effectively so that the CD8+T lymphocytes that encounter them can be activated.

Vaccination approaches with the dendritic cells transduced with RNA particles prove particularly advantageous, and constant expression of the antigen or antigens is not necessary for inducing and maintaining a population of memory T cells (M. J. Bevan and A. W. Goidrath. Current Biology. 2000, 10: R338-R340).

EXAMPLE 6

Demonstration of the Transfer of RNA Coding an Antigen and an Immunomodulating Protein by an RLP Particle into Immune Cells and Effectiveness of the RLP Particle I. Preparation of the Viral Particle According to the Invention and of the Comparative Systems 1. Plasmid Construction Expression plasmids for a sequence of interest: The expression plasmid bears a promoter-sequence of interest-polyA expression cassette with or without an intron sequence or RNA-stabilizing sequence. In order to transport the mRNAs into the lentiviral particles, 12 repetitions of the stem-loop motif of the MS2 RNA (ctagaaaacatgaggatcacc-catgtctgcag, SEQ ID No.1) were inserted within an expression cassette downstream of the reporter gene. The promoter used may be the CMV or EF1 promoter but other promoters may be used. The sequence of interest may code an antigen or an epitope. Many biomarkers were identified on the tumour cells and their complete sequence and/or partial sequences are used in immunotherapy. For example, the sequence used for expressing the MAGEA3 antigen may be complete (FIG. 11A) or partial (FIG. 11B). The sequence of interest may also code an immunomodulating protein, such as a cytokine or an interleukin such as IL-12 for example.

Encapsidation plasmid: This plasmid is identical to that described in Example 1 (the expression cassette of which is as described in FIG. 2).

Envelope plasmid (pENV): This plasmid is identical to that described in Example 1 (the expression cassette of which is as described in FIG. 3).

2. Production of the Batches and Titration

Production of the batches and titration are carried out according to method P2, as described in Example 1, using the following expression plasmids:

Batch RLP-PS-MAGEA3/IL-12: linear pcDNA.EF1long.PPRV.PS-AgMAGEA3.WPRE.MS2 12× (the expression cassette of which is as described in FIG. 11B) and pcDNA.EF1.IL12b-linker-DeltaIL12a.MS2 12× (the expression cassette of which is as described in FIG. 31).

The respective proportions of the plasmids are as follows: 40% of the expression plasmids, 30% of the p8.74 (or p8.74ΔZF) plasmid, 30% of the pENV plasmid.

II. Transduction of Cells of the Immune System

1. U937 Line (ATCC® CRL-1593.2™)

The U937 cell line was cultured under the conditions described in Example 4 (II. paragraph 1).

1.1. Transduction of the U937 Cells with Particles Containing a Mixture of a Tumoral Antigen and an Immunomodulating Protein (RLP-PS-MAGEA3/IL-12)

The transductions of the U937 cells are carried out by the method described in Example 4 (II. paragraph 1.1).

1.2. Recovery of the Cells

At 5 hours and 20 hours post-transduction, the cells are recovered and treated by the method described in Example 4 (II. paragraph 1.2).

1.3. Extraction of the Total RNAs

Each dry pellet is treated by the method described in Example 4 (II. paragraph 1.3) to extract and purify the total RNAs.

1.4. Reverse Transcription of the RNAs

Reverse transcription of the RNAs to complementary DNA is carried out by the method described in Example 4 (II. paragraph 1.4).

1.5. Amplification of the cDNAs by RT-qPCR

Amplification is carried out on 5 μl of cDNA at ¹/₁₀th dilution in ultrapure water, with the real-time PCR mix, SYBR® Premix Ex Taq (Takara—cat RR420L), in the presence of 200 nM of sense and antisense oligonucleotide in a final volume of 20 μl. 5 μl of cDNA at ¹/₁₀th dilution is added to each well.

Real-time PCR is carried out with a StepOnePlus thermocycler (AppliedBiosystems) with the SYBR®Green chemistry according to the following protocol: 1 cycle of 30 seconds at 95.0° C. and then 40 cycles comprising 5 seconds at 95.0° C. and 30 seconds at 60.0° C.

The sense oligonucleotides used are:

```
                                            (SEQ ID No. 4)
Q-hGAPDH-S  (GACAAGCTTCCCGTTCTCAG)

(SEQ ID No. 6)
Q-PSMAGEDC-F  (TCAGCACTCTTTGAGGATCTAATGA)

(SEQ ID No. 13)
Q-IL12ap35-F  (CGGATCTAGGGTCATTCCAGTCT)
```

The antisense oligonucleotides used are:

```
                                            (SEQ ID No. 9)
Q-hGAPDH-AS  (GAGTCAACGGATTTGGTCGT)

(SEQ ID No. 11)
Q-PSMAGETyrDC-R  (GGTAGGCAATGAGGACGATGA)

(SEQ ID No. 14)
Q-IL12ap35-R  (GTTTTTCTCTGGCCGTCTTCA)
```

The combinations of the pairs of oligonucleotides to be used are as follows, depending on the targets:

Target hGAPDH with Q-hGAPDH-S and Q-hGAPDH-AS

Target PS-MAGEDC with Q-PSMageDC-F and Q-PS-MAGETyrDC-R

Target IL12ap35 with Q-IL12ap35-F and Q-IL12ap35-R

Experiments for validation of the specificity of the oligonucleotides had been conducted beforehand.

2. Preparation of the Immature Human Dendritic Cells (hDCs)

The immature human dendritic cells are prepared by a method identical to that described in Example 1 (part II, paragraph 2.1).

2.1 Transduction of the Human Dendritic Cells with Particles Containing a Mixture of a Tumoral Antigen and an Immunomodulating Protein (RLP-PS-MAGEA3/IL-12)

Transduction of the human dendritic cells is carried out by a method identical to that described in Example 1 (part II, paragraph 2.3). The cells are transduced with 4 pg of p24/cell and are analysed at different times (5 h, 20 h post-transduction).

A negative control of transduction is prepared with the medium containing only the transduction agent Polybrene® at 4 μg/mL (Sigma). The dendritic cells are analysed on the day of transduction and at the different analysis times, by RT-qPCR on the RNAs obtained from pellets of transduced cells.

2.2. Recovery of the Cells

For analysis of RNA expression, the human dendritic cells are recovered at the different times after transduction according to the protocol described in Example 4 (II. paragraph 2.2). The cells are frozen at −80° C. in the form of dry pellets. For analysis of the secretion of IL12, samples of the cell culture supernatants are taken at times of 20 h and 48 h post-transduction.

The supernatants are stored at −20° C.

2.3. Extraction of the Total RNAs

The RNAs are prepared by a method identical to that described in Example 4 (II. paragraph 2.3).

2.4. Reverse Transcription of the RNAs

Reverse transcription of the RNAs to complementary DNA is carried out on 500 ng of RNA by the method described in Example 4 (II. paragraph 2.4).

2.5. Amplification of the cDNAs by RT-qPCR

Amplification of the cDNAs by RT-qPCR is carried out by the method described in Example 4 (II. paragraph 2.5).

2.6. ELISA Assay for Secretion of IL12

ELISA assay for quantifying the secretion of IL12 in the cell culture supernatants is carried out according to the protocol supplied with the "Human IL-12 Standard ABTS ELISA Development Kit" (Peprotech).

III. Results:

Specific analysis by RT-qPCR makes it possible to demonstrate the transfer of RNA coding an antigen and an immunomodulating protein, by RLP particles into APCs, in particular into U937 cells and into immature human dendritic cells (hDCs), at 5 h and 20 h post-transduction (FIG. 32 and FIG. 33, FIG. 34 and FIG. 35, respectively). The results obtained are analysed and interpreted according to the presence or absence of significant specific amplification during real-time quantitative PCR (RT-qPCR). The results are normalized with respect to the values obtained for the non-transduced control cells (U937 NT and hDC NT). These controls express endogenous RNA coding IL12 (results not shown). It is known that the dendritic cells produce IL12, which plays a role in the response of the T lymphocytes in vivo.

In the case of the U937 cell line, the relative quantities of the different RNAs are significant at 5 h post-transduction (FIG. 32) and at 20 h post-transduction (FIG. 33).

In the case of the hDC primary cells, the relative specific RNA levels are significant at 20 h (FIG. 35) even if they are less pronounced at 5 h (FIG. 34). Finally, analysis of the culture supernatants by ELISA (FIG. 36) demonstrates a large increase in the levels of IL12 secreted by the hDCs, 48 h after transduction by the RLP-PS-MAGEA3/IL-12 particles.

The RLP particles are therefore effective for transferring different RNA molecules coding an antigenic peptide and for an immunomodulating protein such as IL-12 into APCs (lines and primary cells). The RLP particles are therefore included in an immunotherapy strategy, based on modulating the specificity of the immune response by transferring RNAs coding antigens and for immunomodulating proteins into APCs.

Fine modulation of the immune response is therefore possible, on the one hand at the level of its specificity, by using RLP particles containing RNAs coding different antigens as shown in Example 4, and on the other hand by combining this strategy with induction of stimulating responses by an immunomodulating protein. Simultaneously delivering both antigens and immunomodulators into the target cells ex vivo or in vivo in a single intervention therefore provides an appreciable clinical advantage.

EXAMPLE 7

Effectiveness of a PP7 (NC)-RLP Lentiviral Particle in Immune Cells

I. Preparation of the Viral Particle According to the Invention and of the Comparative Systems 1. Plasmid Construction Expression plasmid for a sequence of interest: The expression plasmid bears an expression cassette as described in FIG. 23 with or without an intron sequence or RNA-stabilizing sequence. In order to transport the mRNAs into the lentiviral particles, 2 repetitions of the stem-loop motif of the PP7 RNA: sequence ctagaaaggagcagacgatatggcgtcgdctccctgcag (SEQ ID No. 2) followed by the sequence ctagaaaccagcagag-catatgggctcgctggctgcag (SEQ ID No. 3) were inserted within an expression cassette downstream of the reporter gene (FIG. 23).

The promoter used may be the CMV or EF1 promoter (FIG. 23). The sequence of interest may be a DNA coding a reporter protein such as native firefly luciferase (FIG. 15), a green (ZsGreen1), red (mCherry) or blue (mtBFP) fluorescent protein, or a cDNA coding a protein, for example protein CRE. Preferably, the cDNA codes an immunogenic protein or an immunomodulating protein. The sequence of interest may also be that of an shRNA, miRNA, sgRNA, LncRNA or circRNA.

Encapsidation plasmid: The lentiviral particle was modified to contain the "Coat" protein sequence of the PP7 bacteriophage (FIG. 37) in the nucleocapsid protein, in place of the second Zn finger domain. The p8.74 encapsidation plasmid bearing the genes coding the structural and functional proteins (Gag, Pol) used for producing the PP7RLP particles is modified in accordance with the following strategy: this p8.74 plasmid is used for generating, by assembly PCR, a plasmid lacking the second zinc finger of the p8.74ΔZF nucleocapsid protein. The second zinc finger is substituted with the Coat protein of the MS2 phage by HpaI cloning, to generate the plasmid p8.74ΔZF-PP7-Coat. The Pol coding sequence may be deleted or mutated in certain functional elements, for example such as the sequence coding reverse transcriptase (RT) or integrase (IN) without altering the function of the PP7RLPs.

Envelope plasmid (pENV): This plasmid bears the gene coding an envelope protein, which may be VSV-G coding the envelope protein of the vesicular stomatitis virus (the expression cassette of which is as described in FIG. 3).

2. Production, Concentration/Purification and Titration of the Lentiviral Particles The lentiviral particles are produced as described in Example 1, according to method P2, using the pcDNA-EF1.ReporterFluorescentPP7 2× expression plasmid described in FIG. 23.

II. Transduction of Murine Dendritic Cells (BMDCs)

The murine dendritic cells are prepared by a method identical to that described in Example 1.

1. Transduction of the Murine Dendritic Cells with PP7 (NC)-RLP.ZsGreen1

The dendritic cells are transduced by the PP7 (NC)-RLP.ZsGreen1 vector as described in Example 1 (II, paragraph 2.4), at a dose of 1 pg p24 per cell and analysed for their viability and expression of the ZsGreen1 fluorescence by flow cytometry at different analysis times (1, 2 and 3 days post-transduction). A negative control of transduction is prepared with only the medium containing the transduction agent Polybrene® at 4 μg/mL (Sigma).

The viability of the dendritic cells is determined by specific immunolabeling with "Viobility™ 485/520" (Miltenyi Biotec) and analysed by flow cytometry.

2. Phenotyping and Characterization of the Cells 2.1 Immunolabeling of the Murine Dendritic Cells At each analysis time, the cells are transferred to the wells of a conical-bottom 96-well culture plate. The cells are washed with a solution of PBS 1× pH 7.4 and centrifuged at 300 g for 5 minutes. The supernatant is removed by inversion.

The viability of the dendritic cells is determined by specific immunolabeling with "Viobility™ 485/520" (Miltenyi Biotec) by a method identical to that described in Example 1 in paragraph II.3.3.

2.2 Flow Cytometry

The immunolabelled dendritic cells are analysed by flow cytometry (Miltenyi Biotec) and analysed. The samples were calibrated according to their size (SSC) and their granularity (FSC). The cells labelled with Viobility™ are dead, therefore the viable cells are the negative cells (labelling by exclusion). The cells are characterized on the MacsQuantVYB (Miltenyi Biotec) and analysed with the MacsQuant software (Miltenyi Biotec).

III. Results: Expression Kinetics of ZsGreen1 and Viability of the BMDCs

FIG. 38 shows that the murine BMDCs transduced with 1 pg p24/cell of PP7 (NC)-RLP particles express ZsGreen1 for 50% of them starting from 24 h post-transduction. Three days post-transduction, the BMDCs are less viable, only 20% of them express ZsGreen1, at a lower fluorescence intensity. The explanation for this is that the PP7(NC)-RLP particles are produced at lower concentrations compared to the MS2RLP or PP7 (IN)-RLP particles and the transduction of the BMDCs at equivalent doses therefore requires the use of larger volumes of lentiviral suspension, which further dilute the culture medium containing the nutrients that are vital for the cells. This is even more notable for culturing sensitive primary cells like the murine BMDCs. It is nevertheless still possible to transport RNAs into the lentiviral particles modified with PP7-Coat in the nucleocapsid.

EXAMPLE 8

Effect of the Wild-Type GAG-POL Precursor for Production of the MS2RLP-ZsGreen1 12× Particles with a View to Optimization of the MS2RLP. PP7RLP and/or PP7 (IN)-RLP Particles I. Preparation of the Viral Particle According to the Invention and of the Comparative Systems 1. Plasmid Construction 1.1 Plasmids for Producing an MS2RLP Lentiviral Particle According to the Invention Expression plasmid for a sequence of interest: This plasmid is identical to that described in Example 1 (the expression cassette of which is as described in FIG. 1).

Figure 5:
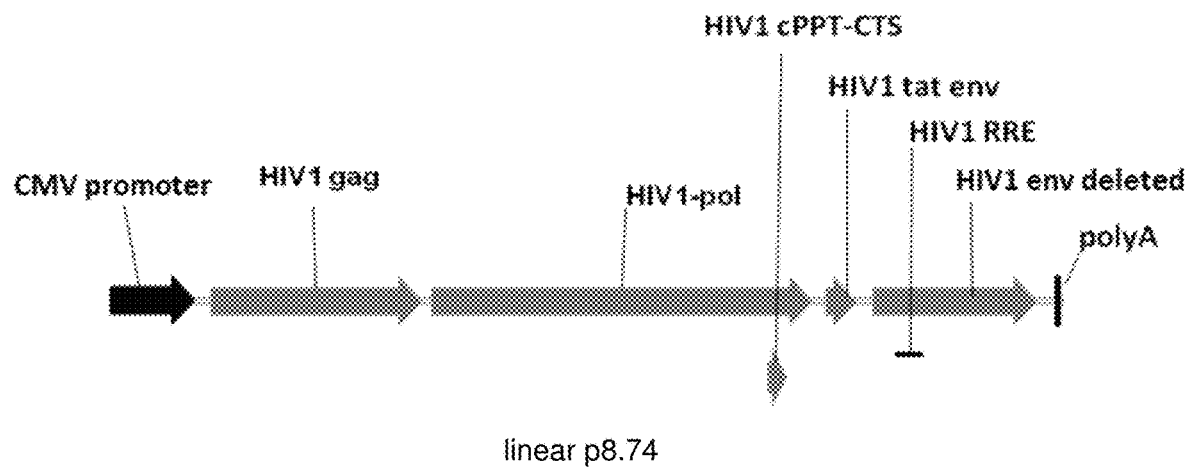
FIG. 5 is a schematic diagram of the construction of the expression cassette derived from the p8.74 encapsidation plasmid used for producing integrative lentiviral vectors (ILV)

Encapsidation plasmids: These plasmids are identical to those described in Example 1: p8.74ΔZF-MS2-Coat (the expression cassette of which is illustrated in FIG. 2) and the p8.74 plasmid (the expression cassette of which is illustrated in FIG. 5)

Envelope plasmid (pENV): This plasmid is identical to that described in Example 1 (the expression cassette of which is as described in FIG. 3).

1.2 Plasmids for Producing Integrative Lentiviral Vectors ILV

Expression plasmid for a sequence of interest: This plasmid is identical to that described in Example 1 (the expression cassette of which is as described in FIG. 4B).

Encapsidation plasmid: This plasmid is identical to that described in Example 1 (the expression cassette of which is as described in FIG. 5).

Envelope plasmid (pENV): This plasmid is identical to that described in Example 1 (the expression cassette of which is as described in FIG. 3).

2. Production of the Batches 2.1 Production of the Lentiviral Particles and Lentiviral Vectors Production is carried out in a 10-stack CellSTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in humid atmosphere at 5% $CO_2$.

The MS2RLP particles are produced by transfection of the following four plasmids:

The expression plasmid described above, the expression cassette of which is illustrated in FIG. 1;

p8.74ΔZF-MS2-Coat (the expression cassette of which is illustrated in FIG. 2) and the p8.74 plasmid (the expression cassette of which is illustrated in FIG. 5), using four different ratios of the two encapsidation plasmids, [100%-0%]; [90%-10%]; [80%-20%] and [50%-50%], respectively;

pENV bearing the envelope VSV-G (the expression cassette of which is illustrated in FIG. 3).

The MS2RLP-ZsGreen1 12× lentiviral particles are produced as described in Example 1, i.e. with the following respective proportions of the plasmids: 40% of the expression plasmid, 30% of the p8.74 (or p8.74ΔZF) plasmid, 30% of the pENV plasmid (ratio [100%-0%]).

More particularly, the respective proportions of the plasmids are as follows:

ratio [90%-10%]: 40% of the expression plasmid, 27% of the p8.74ΔZF plasmid, 3% of the p8.74 plasmid, 30% of the pENV plasmid;

ratio [80%-20%]: 40% of the expression plasmid, 24% of the p8.74ΔZF plasmid, 6% of the p8.74 plasmid, 30% of the pENV plasmid ratio [50%-50%]: 40% of the expression plasmid, 15% of the p8.74ΔZF plasmid, 15% of the p8.74 plasmid, 30% of the pENV plasmid.

In the case of production of RLP-TAAs lentiviral particles, the proportions of plasmids described above remain unchanged.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

The ILV-ZsGreen1 integrative lentiviral vectors containing the EF1-ZsGreen1 expression cassette are produced as a control, as described in Example 1.

2.2 Concentration and Purification of the Lentiviral Particles

The lentiviral particles and the lentiviral vectors are concentrated and purified according to method P1 described in Example 1.

3. Titration

The lentiviral particles and the lentiviral vectors are titrated as described in Example 1.

II. Transduction

1. Preparation of the Jurkat Target Cells and Transduction by MS2RLP 12× Lentiviral Particles According to the Invention Jurkat target cells (ATCC TIB-152) are seeded at 200000 cells/mL in a 96-well plate, transduced by the MS2RLP particles at two doses (2 and 10 pg p24/cell), or by ILV-ZsGreen1 control lentiviral vectors at MOI40, in the presence of 4 μg/mL Polybrene® and then incubated at 37° C./5% $CO_2$. A cell defence mechanism inhibitor, BX795 (Invivogen), is used at a concentration of 6 μM In the case of the MS2RLP particles. The transduction supernatant is removed 5 hours later and replaced with fresh supplemented culture medium. 24 h post-transduction, the target cells are recovered and the percentage of cells expressing ZsGreen1 is quantified by cytometry (Macs Quant VYB, Miltenyl Biotec).

2. Analysis of Maturation of the MS2RLP Viral Particles by Anti-p24 Western Blot 48 h after transfection of the producer cells (HEK293T) with the plasmids for producing the MS2RLP particles, the culture supernatants are recovered and then concentrated according to method P1, as described in Example 1, and titrated by quantification of the p24 protein, as described in Example 1. The equivalent of 15 ng of p24 is loaded for each condition of ratio of the p8.74ΔZF-MS2-Coat/p8.74 plasmids on a denaturing gel SDS-PAGE 4/12% and then migrated for 1 h at 200V In MOPS1xbuffer. After transfer onto a nylon membrane, the proteins are hybridized to an anti-p24 antibody (clone 39/5.4A, Abcam). The Western blot is developed using the Pierce™ Fast Western Blot Kit, ECL Substrate (Pierce). The bands are visualized by chemiluminescence on autoradiography film.

III. Results

This example alms to show that it is possible to improve the functionality of the MS2RLP and PP7RLP particles for transferring RNAs coding different antigens or for transferring RNAs coding antigens and for an immunomodulating protein. This proceeds via improvement of maturation of the GAG precursor during production of the particles, demonstrated by the proof of concept on the production of MS2RLP particles. The p8.74ΔZF-MS2 plasmid allows expression of a GAG precursor comprising the Coat protein of the bacteriophage in place of the second zinc finger of the Nucleocapsid protein. This Coat protein is likely to disturb the maturation of the GAG precursor, when it is cleaved into three proteins: the matrix protein, the capsid protein and the nucleocapsid protein. These three proteins are indispensable to the structure of the viral particles.

Supply of the wild-type GAG precursor, by the p8.74 plasmid in addition to the p8.74ΔZF-MS2-Coat encapsidation plasmid during production of the MS2RLP-ZsGreen1 12× particles might make it possible to increase the maturation of the GAG precursor when it is expressed owing to the p8.74ΔZF-MS2 plasmid, and thus increase the functionality of the MS2RLP and PP7RLP particles.

The purpose of this experiment is to evaluate the effect of the p8.74 plasmid when it is co-transfected, in the producer cells of the MS2RLP and PP7RLP particles, at the same time as the p8.74ΔZF-MS2-Coat encapsidation plasmid, making it possible to improve the maturation of the GAG precursor, and thus make the final particles more functional for the transduction of target cells.

In this example, four ratios of p8.74ΔZF-MS2-Coat/p8.74 encapsidation plasmids are tested: 100/0; 90/10; 80/20 and 50/50. An integrating vector ILV expressing ZsGreen1 is used as a control. The cells are transduced at two quantities of p24/ml: 2 pg p24/cell (FIG. 39) and 10 pg p24/cell (FIG. 40).

Firstly, the results presented in FIG. 39 show that for the non-transduced cells, the percentage of fluorescent cells is very close to 0, whereas the cells transduced by the MS2RLP-ZsGreen1 12× particles are fluorescent to more than 99% whatever the ratio of encapsidation plasmids used. It is important to note that the fluorescence intensity of ZsGreen1 increases as a function of the increase in the quantity of p8.74 plasmid. The cells transduced by the MS2RLP-ZsGreen1 12× particles produced with 50% of the p8.74ΔZF-MS2-Coat encapsidation plasmid and 50% of the p8.74 plasmid have a fluorescence intensity of 7.76 whereas that of the cells transduced by the MS2RLP-ZsGreen1 12× particles produced only with the p8.74ΔZF-MS2-Coat encapsidation plasmid is 3.5.

FIG. 40 shows the same result in terms of percentage of cells transduced. Regarding the fluorescence intensity, the more the quantity of p8.74 plasmid increases, the more the fluorescence intensity increases, as shown in FIG. 39. The cells transduced by the MS2RLP-ZsGreen1 12× particles produced with 50% of the p8.74ΔZF-MS2-Coat encapsidation plasmid and 50% of the p8.74 plasmid have a fluorescence intensity of 60.67 whereas that of the cells transduced by the MS2RLP-ZsGreen1 12× particles produced only with the p8.74ΔZF-MS2-Coat encapsidation plasmid is 11.48.

This means that at doses of 2 pg and 10 pg p24/cell, the fluorescence obtained is two and five times greater respectively when the particles are produced with 50% of the p8.74ΔZF-MS2-Coat encapsidation plasmid and 50% of the p8.74 plasmid than when they are produced only with the p8.74ΔZF-MS2-Coat plasmid.

The use of the p8.74 plasmid in the production of MS2RLP particles, in co-transfection with the p8.74ΔZF-MS2-Coat plasmid, has therefore supplied a gain on the improvement of the functionality of the MS2RLP-ZsGreen1 12× particles, with a view to optimization of the MS2RLP particles for transferring RNAs coding different antigens or for transferring RNAs coding antigens and for an immunomodulating protein.

FIG. 41 shows the maturation of the MS2RLP-ZsGreen1 12× particles at the biochemical level, by detecting the p24 protein in the production supernatant containing the particles. It corresponds to analysis of the viral supernatants by anti-p24 Western blot, at two exposure times of the autoradiography film, one minute (FIG. 41A) and fifteen seconds (FIG. 41B).

In the case of an integrating lentiviral particle derived from HIV, produced only with the p8.74 plasmid as encapsidation plasmid, the p24 protein is detectable at four levels:
  in the p160 protein precursor (GAG-POL)
  in the p55 protein precursor (GAG),
  in the state of mature protein (p24),
  in other intermediate protein precursors in the course of maturation (between p160 and p55, and between p55 and p24).

If maturation takes place normally, the p24 protein should be detected in larger quantities in the mature state (p24) than in the state of protein precursors (p160, p55) or of intermediate protein precursors. In fact, maturation of the viral particles takes place after release of the particle by the producer cell. In other words, during their production, the particles bud at the surface of the producer cell, and are then released from the cell in the state of immature particles. It is only after release of the particles in the supernatant that the GAG-POL and GAG protein precursors mature into definitive proteins.

In the case of an MS2RLP or PP7RLP particle derived from HIV, produced only with the p8.74ΔZF-MS2-Coat plasmid as encapsidation plasmid, the p24 protein is detectable at four levels:
  in the p172 protein precursor (GAGΔZF-MS2-Coat-POL)
  in the p67 protein precursor (GAGΔZF-MS2-Coat),
  in the state of mature protein (p24),
  In other intermediate protein precursors in the course of maturation (between p172 and p67, and between p67 and p24).

In this MS2RLP-ZsGreen1 12x particle, each precursor is heavier by 12 kDa, which corresponds to the size of the Coat protein of the MS2 bacteriophage inserted in the second zinc finger of the nucleocapsid protein.

FIG. 41 shows, on the ILV track, the different forms of protein precursors, p160 (GAG-POL), p55 (GAG) as well as the perfectly mature p24 protein. There is a preponderance of mature p24 protein, compared to the protein precursor forms. On track 100/0, corresponding to MS2RLP-ZsGreen1 12x particles produced only with the p8.74ΔZF-MS2-Coat plasmid as encapsidation plasmid, the proportion of precursors/mature p24 protein increases with respect to the ILV, showing that insertion of the Coat protein of the MS2 bacteriophage reduces the maturation of the viral particles. On tracks 90/10, 80/20 and 50/50, the proportion of p172 and p67 protein precursors decreases to the benefit of the p160 and p55 protein precursors respectively, reaching one and the same expression level for track 50/50. Addition of the p8.74 plasmid to the p8.74ΔZF-MS2-Coat plasmid, as encapsidation plasmid for producing particles, leads to an increase in the proportion of the mature p24 protein (FIG. 41B, 15 seconds exposure). This result shows that to promote maturation of the protein precursors in the MS2RLP particles, it is possible to add at least 10% of p8.74 plasmid in addition to the p8.74ΔZF-MS2-Coat plasmid as encapsidation plasmid for producing particles. Production of the MS2RLP particles using at least 10% of p8.74 plasmid in addition to the p8.74ΔZF-MS2-Coat plasmid as encapsidation plasmid not only makes it possible to increase the maturation of the precursors into mature proteins, but in addition makes it possible to increase the functionality of the particles after transduction of target cells.

In conclusion, use of the p8.74 plasmid during production of particles according to the invention, in co-transfection with the p8.74ΔZF-MS2-Coat plasmid, makes it possible to optimize the particles according to the invention for transferring RNAs coding different antigens or for transferring RNAs coding antigens and for an immunomodulating protein.

EXAMPLE 9

Recruitment of Non-Viral RNAs Directed by Two Different Encapsidation Sequences (MS2 and PP7) with a View to Optimization of the Effective Transfer of RNA Coding Different Antigens or for Transferring RNAs Coding Antigens and an Immunomodulating Protein, by an RLP Particle (Modulation of the Types of RNA Encapsidated)

I. Preparation of the Viral Particle According to the Invention and of the Comparative Systems 1. Plasmid Construction 1.1 Plasmids for Producing MS2/PP7-(NC) RLP 12x 2x Lentiviral Particles According to the Invention Expression plasmids for a sequence of interest: These plasmids are identical to that described in Example 1 (the expression cassette of which is as described in FIG. 1) and in Example 7 (the expression cassette of which is as described in FIG. 23).

Encapsidation plasmids: These plasmids are identical to that described in Example 1 (the expression cassette of which is as described in FIG. 2) and in Example 7 (the expression cassette of which is as described in FIG. 37).

Envelope plasmid (pENV): This plasmid bears the gene coding an envelope protein, which may be VSV-G coding the envelope protein of the vesicular stomatitis virus (FIG. 3).

Preferably, these plasmids are used for producing MS2/PP7-RLP-mCherry 12x-ZsGreen1 2x lentiviral particles.

1.2 Plasmids for Producing Control MS2-(NC) RLP 12x Lentiviral Particles According to the Invention Expression plasmid for a sequence of interest: This plasmid is identical to that described in Example 1 (the expression cassette of which is as described in FIG. 1).

Encapsidation plasmid: This plasmid is identical to that described in Example 1 (the expression cassette of which is as described in FIG. 2).

Envelope plasmid (pENV): This plasmid is identical to that described in Example 1 (the expression cassette of which is as described in FIG. 3).

Preferably, these plasmids are used for producing MS2RLP-mCherry 12x lentiviral particles.

1.3 Plasmids for Producing Control PP7-(NC) RLP 2x Lentiviral Particles According to the Invention Expression plasmid for a sequence of interest: This plasmid is identical to that described in Example 7 (the expression cassette of which is as described in FIG. 23).

Encapsidation plasmid: This plasmid is identical to that described in Example 7 (the expression cassette of which is as described in FIG. 37).

Envelope plasmid (pENV): This plasmid bears the gene coding an envelope protein, which may be VSV-G coding the envelope protein of the vesicular stomatitis virus (FIG. 3).

Preferably, these plasmids are used for producing PP7RLP-ZsGreen1 2x lentiviral particles.

2. Production of the Batches

After transfection of the plasmids on producer cells, the supernatants are harvested and used crude or concentrated/purified according to one of the aforementioned methods P1 or P2 described in application WO 2013/014537.

2.1 Production of the Lentiviral Particles

Production is carried out in a 10-stack CellSTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. In humid atmosphere at 5% $CO_2$.

The production of the lentiviral particles MS2/PP7-(NC) RLP 12x 2x, preferably MS2/PP7-RLP-mCherry 12x-ZsGreen1 2x, is carried out by transfection of the following five plasmids:

The two expression plasmids described above, of which the pcDNA.EF1.mCherry.MS2 12x plasmid (the expression cassette of which is illustrated in FIG. 1) and the pcDNA.EF1.ZsGreen1.PP7 2x plasmid (the expression cassette of which is illustrated in FIG. 23) are used in single or double quantity;

p8.74ΔZF-PP7-Coat (50%) the expression cassette of which is illustrated in FIG. 37 and p8.74ΔZF-MS2-Coat (50%) the expression cassette of which is illustrated in FIG. 2;

pENV bearing the envelope VSV-G the expression cassette of which is illustrated in FIG. 3.

The control lentiviral particles MS2-(NC) RLP 12x, preferably MS2-RLP-mCherry 12x, are produced by transfection of the following three plasmids:

The pcDNA.EF1.mCherry.MS2 12× expression plasmid described above (the expression cassette of which is illustrated in FIG. 1);
p8.74ΔZF-MS2-Coat the expression cassette of which is illustrated in FIG. 2;
pENV bearing the envelope VSV-G the expression cassette of which is illustrated in FIG. 3.

The control lentiviral particles PP7-(NC) RLP 2×, preferably PP7-RLP-ZsGreen1 2×, are produced by transfection of the following three plasmids:
The pcDNA.EF1.ZsGreen1.PP7 2× expression plasmid described above (the expression cassette of which Is illustrated in FIG. 23);
p8.74ΔZF-PP7-Coat the expression cassette of which is illustrated in FIG. 37;
pENV bearing the envelope VSV-G the expression cassette of which is illustrated in FIG. 3.

24 hours after standard transfection with calcium phosphate, the culture supernatant is replaced with fresh unsupplemented DMEM medium. The producer cells are Incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

2.2 Concentration and Purification of the Lentiviral Particles

The lentiviral particles are concentrated and purified according to method P1 described in Example 1.

3. Titration of the Batches of Lentiviral Particles

The lentiviral particles are titrated as described in Example 1.

4. Transduction by MS2/PP7-(NC) RLP 12× 2× Lentiviral Particles According to the Invention This example is carried out using MS2/PP7-(NC) RLP 12× 2× particles allowing transfer of several types of RNAs and therefore expression of several different proteins (ZsGreen1+mCherry).

HCT116 target cells (ATCC, CCL-247) were seeded in a 24-well plate and incubated for 24 h at 37° C./5% $CO_2$ and were transduced by the MS2/PP7-(NC) RLP 12× 2× particles at a dose of 10 pg p24/cell.

The following checks are carried out:
transduction with the MS2RLP-mCherry 12× and PP7RLP-ZsGreen1 2× lentiviral particles, at a dose of 10 pg p24/cell each;
transduction with the MS2RLP-mCherry 12× lentiviral particles alone, at a dose of 10 pg p24/cell;
transduction with the PP7RLP-ZsGreen1 2× lentiviral particles alone, at a dose of 10 pg p24/cell.

Transduction by the lentiviral particles is carried out in the presence of 8 μg/mL of Polybrene®. A cell defence mechanism Inhibitor, BX795 (Invivogen), is used at a concentration of 6 μM In the case of the MS2/PP7-(NC) RLP 12× 2×, MS2RLP-mCherry 12× and PP7RLP-ZsGreen1 2× particles. The target cells are recovered at 48 h post-transduction and the percentage of cells expressing ZsGreen1 and mCherry is quantified by cytometry (Macs Quant VYB, Miltenyl Biotec).

II. Results

FIG. 42 illustrates the effectiveness of the MS2/PP7-(NC) RLP 12× 2× particles for transferring RNAs encapsidated by the encapsidation sequences derived from the MS2 and PP7 bacteriophages in HCT116 target cells. The figure shows that the proportion of bi-fluorescent cells is 97% after transduction of the MS2/PP7-(NC) RLP 12× 2× particles and 98% after transduction of the MS2RLP-mCherry 12× and PP7RLP-ZsGreen1 2× particles at 20 pg p24/cell. The same order of transduction effectiveness is therefore observed with the MS2/PP7-(NC) RLP 12× 2× particles, for half the dose of MS2/PP7-(NC) RLP 12× 2×.

The target cells transduced by the MS2RLP-mCherry 12× particles alone or PP7RLP-ZsGreen1 2× particles alone have a percentage transduction effectiveness similar to the percentage obtained after transduction of the target cells by the MS2/PP7-(NC) RLP 12× 2× particles for a single fluorescent protein. The results therefore show that the RLP particles are capable of transporting and transferring at least 2 types of RNAs encapsidated by two different systems (PP7 and MS2) In a single transduction of the target cells.

Demonstration of the ability to transfer different types of RNAs directed by two different encapsidation sequences, MS2 and PP7, in a single transduction of one and the same batch of RLP represents a significant gain on the modulation of the types of RNA encapsidated, in particular for efficient transfer of RNAs coding different antigens or for transferring RNAs coding antigens and for an Immunomodulating protein.

The invention claimed is:

1. A retroviral particle comprising:
a protein derived from the Gag polyprotein;
an envelope protein;
at least two encapsidated non-viral RNAs; and
optionally an integrase, the encapsidated non-viral RNAs each comprising an RNA sequence of interest bound to an encapsidation sequence, each encapsidation sequence being recognized by a heterologous binding domain inserted into the protein derived from the Gag polyprotein and/or into the integrase, and at least one of said sequences of interest of the encapsidated non-viral RNAs comprises a part coding at least one epitope deriving from a pathogen and/or at least one molecular structure specifically recognizing an epitope deriving from a pathogen, said molecular structure being an immunoreceptor constituted by the variable part of an antibody or of a membrane receptor of lymphocytes.

2. The retroviral particle according to claim 1, comprising a nucleocapsid protein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a heterologous binding domain inserted into the nucleocapsid protein and/or into the integrase.

3. The retroviral particle according to claim 2, in which the sequences of interest of the at least two encapsidated non-viral RNAs are identical.

4. The retroviral particle according to claim 2, in which the at least two encapsidated non-viral RNAs differ in their RNA sequence.

5. The retroviral particle according to claim 4, in which the sequence of interest of the other encapsidated non-viral RNA codes an immunomodulating protein.

6. The retroviral particle according to claim 3, further comprising a third encapsidated non-viral RNA.

7. The retroviral particle according to claim 2, in which the heterologous binding domain is inserted into the nucleocapsid protein, and a second heterologous binding domain may be introduced into the nucleocapsid and/or into the integrase.

8. The retroviral particle according to claim 1, in which the heterologous binding domain is inserted into the integrase, and a second heterologous binding domain may be introduced into the nucleocapsid and/or into the integrase.

9. The retroviral particle according to claim 2, which is a lentiviral particle.

10. A lentiviral particle according to claim 9, in which:
the binding domain is the "Coat" protein sequence of the MS2 bacteriophage,
the encapsidation sequence of the non-viral RNAs is a stem-loop sequence of MS2,
the nucleocapsid protein is the nucleocapsid protein (NC) of HIV belonging to the Gag polyprotein, said NC being mutated at the second zinc finger in order to insert the "Coat" protein sequence of the MS2 bacteriophage.

11. The lentiviral particle according to claim 9, in which:
the binding domain is the "Coat" protein sequence of the PP7 phage,
the encapsidation sequence of the non-viral RNAs is a PP7 stem-loop sequence,
the nucleocapsid protein is the nucleocapsid protein (NC) of HIV belonging to the Gag polyprotein, said NC being mutated at the second zinc finger in order to insert the "Coat" protein sequence of the PP7 bacteriophage.

12. A composition comprising a plurality of the particle according to claim 1.

13. Kit for producing particles according to claim 1, comprising:
(i) an expression plasmid comprising at least one sequence of interest, for which an encapsidation sequence is inserted upstream or downstream of said sequence, the at least one sequence of interest comprising a part encoding at least one epitope deriving from a pathogen and/or at least one molecular structure specifically recognizing an epitope deriving from a pathogen,
(ii) an encapsidation plasmid coding a protein originating from the Gag polyprotein and/or a chimeric integrase, comprising a heterologous binding domain enabling an encapsidation sequence to be recognized, and,
(iii) an envelope plasmid coding an envelope protein.

14. Production kit according to claim 13, further comprising a second encapsidation plasmid coding:
a protein derived from the wild-type Gag polyprotein, when the first encapsidation plasmid codes a protein derived from the chimeric Gag polyprotein, and/or
a wild-type integrase, when the first encapsidation plasmid codes a chimeric integrase.

15. Method for manufacturing a kit according to claim 13, comprising:
(i) preparing an expression plasmid comprising at least one sequence of interest, for which an encapsidation sequence is inserted upstream or downstream of said sequence, the at least one sequence of interest comprising a part encoding at least one epitope deriving from a pathogen and/or at least one molecular structure specifically recognizing an epitope deriving from a pathogen,
(ii) preparing an encapsidation plasmid coding a protein derived from the Gag polyprotein and/or a chimeric integrase comprising a heterologous binding domain enabling an encapsidation sequence to be recognized, and
(iii) preparing an envelope plasmid coding an envelope protein.

16. Method for manufacturing the particles according to claim 1, comprising a step of co-transfecting cells with:
(i) an expression plasmid comprising at least one sequence of interest, for which an encapsidation sequence is inserted upstream or downstream of this sequence, the at least one sequence of interest comprising a part encoding at least one epitope deriving from a pathogen and/or at least one molecular structure specifically recognizing an epitope deriving from a pathogen,
(ii) an encapsidation plasmid encoding a protein derived from the Gag polyprotein and/or a chimeric integrase comprising a heterologous binding domain enabling an encapsidation sequence to be recognized, and
(iii) an envelope plasmid encoding an envelope protein, and harvesting the supernatant of the transfected cells comprising the particles.

17. Method for manufacturing the particles according to claim 4, comprising a step of co-transfecting cells with:
(i) an expression plasmid comprising at least two different non-viral RNA sequences, each RNA sequence comprising a sequence of interest for which an encapsidation sequence is inserted upstream or downstream of said sequence of interest, or alternatively a first and a second expression plasmid each comprising a sequence of interest, upstream or downstream of which an encapsidation sequence is inserted, at least one of said sequences of interest comprising a part encoding at least one epitope deriving from a pathogen and/or at least one molecular structure specifically recognizing an epitope deriving from a pathogen,
(ii) an encapsidation plasmid coding a chimeric nucleocapsid protein comprising a heterologous binding domain making it possible to recognize the encapsidation sequence, and,
(iii) an envelope plasmid coding an envelope protein, and harvesting the supernatant of the transfected cells comprising the particles.

18. Method of manufacture according to claim 16, in which the supernatant is clarified, and then optionally concentrated and/or purified.

19. Method of manufacture according to claim 16, in which the co-transfecting step is additionally carried out with a second encapsidation plasmid coding:
a protein derived from the wild-type Gag polyprotein, when the first encapsidation plasmid codes a protein derived from the chimeric Gag polyprotein, and/or
a wild-type integrase, when the first encapsidation plasmid codes a chimeric integrase.

20. Composition obtainable by the method according to claim 16.

21. Method for transiently modifying cells involved in the immune response by transducing said cells with a particle according to claim 1.

* * * * *